US011823799B2

United States Patent
Bagnard et al.

(10) Patent No.: US 11,823,799 B2
(45) Date of Patent: Nov. 21, 2023

(54) METHOD FOR IDENTIFYING PERSONALIZED THERAPEUTIC STRATEGIES FOR PATIENTS AFFECTED WITH A CANCER

(71) Applicants: UNIVERSITE DE STRASBOURG, Strasbourg (FR); INSERM (INSTITUT NATIONAL DE LA SANTE ET DE LA RECHERCHE MEDICALE), Paris (FR)

(72) Inventors: Dominique Bagnard, Ammerschwihr (FR); Aurore Fernandez, Strasbourg (FR); Laurent Jacob, Strasbourg (FR); Justine Fritz, Strasbourg (FR)

(73) Assignees: UNIVERSITE DE STRASBOURG, Strasbourg (FR); INSERM (INSTITUT NATIONAL DE LA SANTE ET DE LA RECHERCHE MEDICALE), Paris (FR)

( * ) Notice: Subject to any disclaimer, the term of this patent is extended or adjusted under 35 U.S.C. 154(b) by 1317 days.

(21) Appl. No.: 15/777,234

(22) PCT Filed: Nov. 21, 2016

(86) PCT No.: PCT/EP2016/078353
§ 371 (c)(1),
(2) Date: May 18, 2018

(87) PCT Pub. No.: WO2017/085326
PCT Pub. Date: May 26, 2017

(65) Prior Publication Data
US 2018/0357364 A1 Dec. 13, 2018

Related U.S. Application Data
(60) Provisional application No. 62/257,938, filed on Nov. 20, 2015.

(30) Foreign Application Priority Data

Nov. 20, 2015 (EP) .................................... 15306845

(51) Int. Cl.
C12Q 1/6886 (2018.01)
G16H 50/20 (2018.01)
G16H 50/50 (2018.01)
G16H 20/10 (2018.01)

(52) U.S. Cl.
CPC .......... *G16H 50/20* (2018.01); *C12Q 1/6886* (2013.01); *G16H 20/10* (2018.01); *G16H 50/50* (2018.01); *C12Q 2600/106* (2013.01); *C12Q 2600/112* (2013.01); *C12Q 2600/118* (2013.01); *C12Q 2600/158* (2013.01)

(58) Field of Classification Search
None
See application file for complete search history.

(56) References Cited

U.S. PATENT DOCUMENTS

| 8,889,354 | B2 * | 11/2014 | Bryant ............. G01N 33/57434 435/6.1 |
| 11,174,517 | B2 * | 11/2021 | Stone .................... C12Q 1/6886 |
| 2015/0322530 | A1 * | 11/2015 | Orsulic .................. A61P 35/00 435/6.12 |
| 2017/0107577 | A1 * | 4/2017 | Al-Ejeh ............... C12Q 1/6886 |

FOREIGN PATENT DOCUMENTS

WO WO 2006/124836 11/2006

OTHER PUBLICATIONS

Huang, Min, et al. "Molecularly targeted cancer therapy: some lessons from the past decade." Trends in pharmacological sciences 35.1 (2014): 41-50 (Year: 2014).*
Parikh JR, Klinger B, Xia Y, Marto JA, Blüthgen N. Discovering causal signaling pathways through gene-expression patterns. Nucleic Acids Res. 2010;38(Web Server issue):W109-W117 (Year: 2010).*
Blaskovich, Michelle A., et al. "Discovery of JSI-124 (cucurbitacin I), a selective Janus kinase/signal transducer and activator of transcription 3 signaling pathway inhibitor with potent antitumor activity against human and murine cancer cells in mice." Cancer research 63.6 (2003): 1270-1279 (Year: 2003).*
Brambilla, E., and A. Gazdar. "Pathogenesis of lung cancer signalling pathways: roadmap for therapies." European Respiratory Journal 33.6 (2009): 1485-1497 (Year: 2009).*
Artemov, A. et al. "A method for predicting target drug efficiency in cancer based on the analysis of signaling pathway activation" *Oncotarget*, Aug. 7, 2015, pp. 29347-29356, vol. 6, No. 30.
Zhu, Q. et al. "Pathway activation strength is a novel independent prognostic biomarker for cetuximab sensitivity in colorectal cancer patients" *Human Genome Variation*, Apr. 2, 2015, pp. 1-9, vol. 2.
Written Opinion in International Application No. PCT/EP2016/078353, dated Jan. 25, 2017, pp. 1-6.

* cited by examiner

*Primary Examiner* — Soren Harward
*Assistant Examiner* — Mary C Leverett
(74) *Attorney, Agent, or Firm* — SALIWANCHIK, LLOYD & EISENSCHENK

(57) ABSTRACT

The present invention provides a powerful tool to identify personalized therapeutic strategies. In particular, the invention provides methods for determining therapeutically targetable dominant signaling pathways in a cancer sample from a subject affected with a solid cancer, determining a treatment protocol for the subject, selecting a subject for a therapy, determining whether the subject is susceptible to benefit from a therapy, predicting clinical outcome of the subject, treating the subject and/or predicting the sensitivity of a solid cancer to a therapy.

13 Claims, 40 Drawing Sheets

A

| Targets | $2^{-\Delta\Delta ct}$ (brain) | $2^{-\Delta\Delta ct}$ (astrocyte) | $2^{-\Delta\Delta ct}$ (oligodendrocyte) | $2^{-\Delta\Delta ct}$ (astrocytoma) | Score |
|---|---|---|---|---|---|
| BCL2 | 0,37 | 14,19 | 1,01 | 0,31 | 15,89 |
| CD133 | 2,09 | 1,79 | 14,37 | 108,05 | 126,29 |
| CMET | 0,07 | 1,23 | 1,26 | 6,44 | 9,00 |
| EGFR | 12,01 | 51,72 | 21,27 | 1,61 | 86,60 |
| FGF2 | 2,07 | 1,72 | 5,84 | 2,06 | 11,69 |
| HER2 | 14,20 | 11,39 | 39,46 | 20,06 | 85,11 |
| HIFA | 2,87 | 9,19 | 8,73 | 1,92 | 22,71 |
| INTB1 | 1,01 | 0,84 | 1,37 | 1,53 | 4,75 |
| JAG1 | 3,29 | 6,57 | 16,25 | 10,00 | 36,12 |
| MMP2 | 7,66 | 1,19 | 13,61 | 5,28 | 27,74 |
| MMP9 | 3,33 | 361,15 | 93,69 | 9,46 | 467,63 |
| NRP1 | 10,95 | 36,06 | 11,26 | 15,40 | 73,68 |
| NRP2 | 2,71 | 2,56 | 7,76 | 1,62 | 14,66 |
| PARG | 0,99 | 3,91 | 3,27 | 3,20 | 11,36 |
| PDGFRA | 0,30 | 2,27 | 0,57 | 3,43 | 6,57 |
| PLEXA1 | 0,64 | 9,70 | 3,37 | 8,42 | 22,13 |
| SDF1 | 1,01 | 0,81 | 2,76 | 2,50 | 7,07 |
| SEMA3A | 0,15 | 0,33 | 0,37 | 2,41 | 3,26 |
| TNC | 8,39 | 1,31 | 15,77 | 16,89 | 42,36 |
| VEGFA | 102,58 | 822,07 | 406,88 | 217,95 | 1549,48 |
| VEGFR1 | 0,02 | 0,25 | 0,09 | 0,04 | 0,39 |
| VEGFR2 | 0,08 | 130,75 | 0,23 | 0,45 | 131,51 |

B

| Targets | Rank | Score | Normalized Score |
|---|---|---|---|
| VEGFA | 1 | 1549,48 | 1000 |
| MMP9 | 2 | 467,63 | 301,80 |
| VEGFR2 | 3 | 131,51 | 84,87 |
| CD133 | 4 | 126,29 | 81,51 |
| EGFR | 5 | 86,60 | 55,89 |
| HER2 | 6 | 85,11 | 54,93 |
| NRP1 | 7 | 73,68 | 47,55 |
| TNC | 8 | 42,36 | 27,34 |
| JAG1 | 9 | 36,12 | 23,31 |
| MMP2 | 10 | 27,74 | 17,90 |
| HIFA | 11 | 22,71 | 14,66 |
| PLEXA1 | 12 | 22,13 | 14,28 |
| BCL2 | 13 | 15,89 | 10,25 |
| NRP2 | 14 | 14,66 | 9,46 |
| FGF2 | 15 | 11,69 | 7,55 |
| PARG | 16 | 11,36 | 7,33 |
| CMET | 17 | 9,00 | 5,81 |
| SDF1 | 18 | 7,07 | 4,56 |
| PDGFRA | 19 | 6,57 | 4,24 |
| INTB1 | 20 | 4,75 | 3,07 |
| SEMA3A | 21 | 3,26 | 2,10 |
| VEGFR1 | 22 | 0,39 | 0,25 |

C

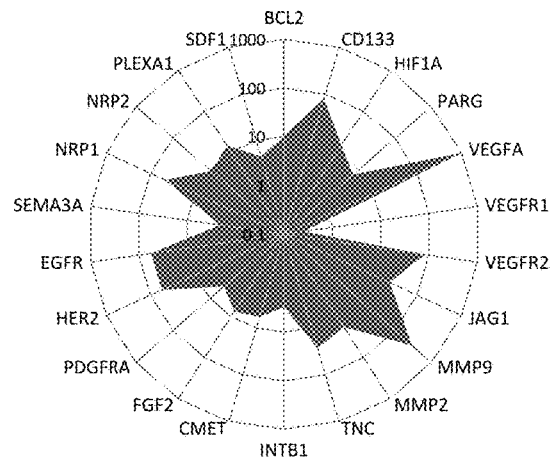

| Targets | Rank | Score | Normalized Score | Normalized score of restricted signature |
|---------|------|-------|------------------|------------------------------------------|
| MMP9 | 2 | 467,63 | 301,80 | 1000 |
| VEGFR2 | 3 | 131,51 | 84,87 | 281,2265876 |
| EGFR | 5 | 86,60 | 55,89 | 185,186129 |
| HER2 | 6 | 85,11 | 54,93 | 181,9990745 |
| MMP2 | 10 | 27,74 | 17,90 | 59,32769751 |
| PARG | 16 | 11,36 | 7,33 | 24,29683989 |
| CMET | 17 | 9,00 | 5,81 | 19,25025767 |
| PDGFRA | 19 | 6,57 | 4,24 | 14,0500211 |
| VEGFR1 | 22 | 0,39 | 0,25 | 0,84103243 |

B

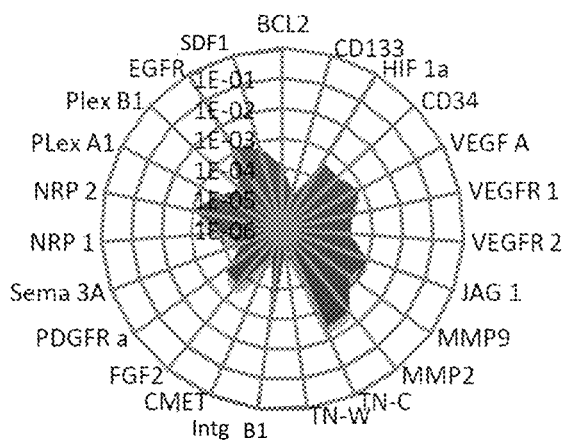
Figure 7A
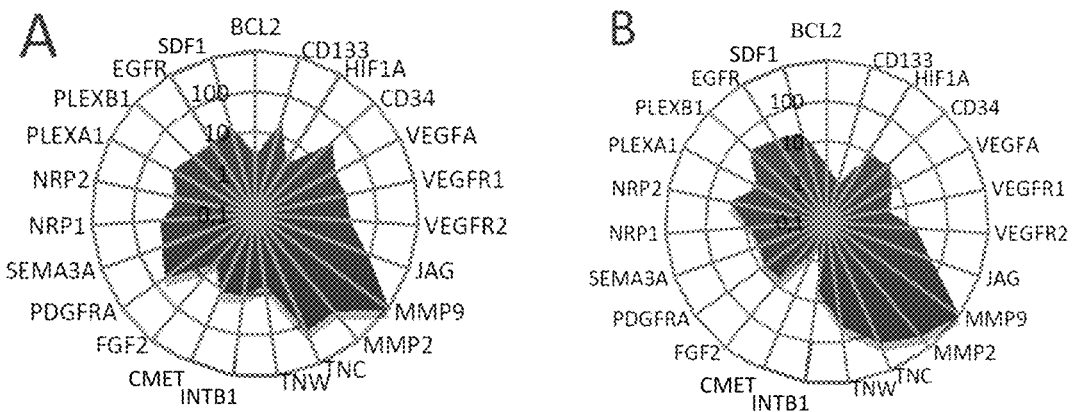
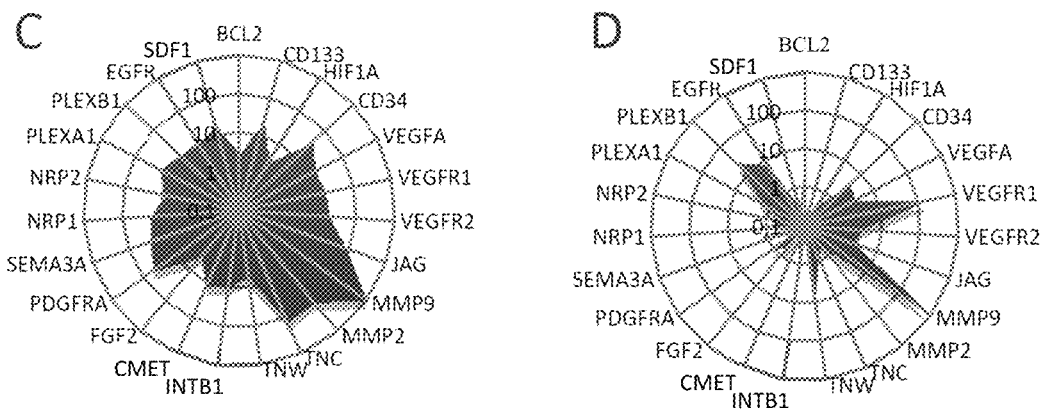
Figure 7B

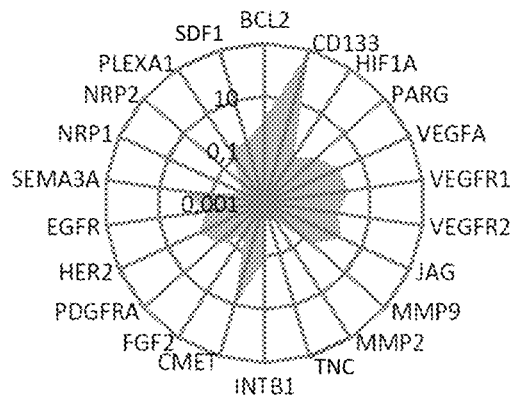
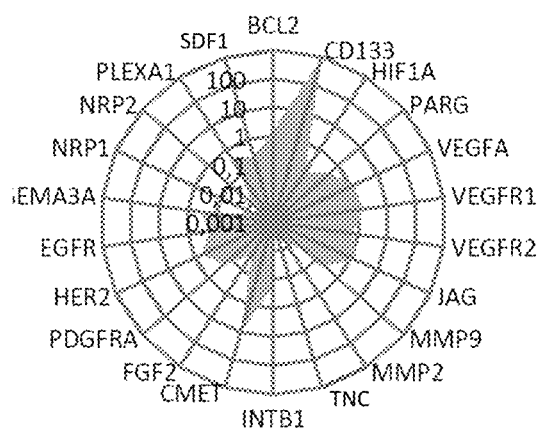
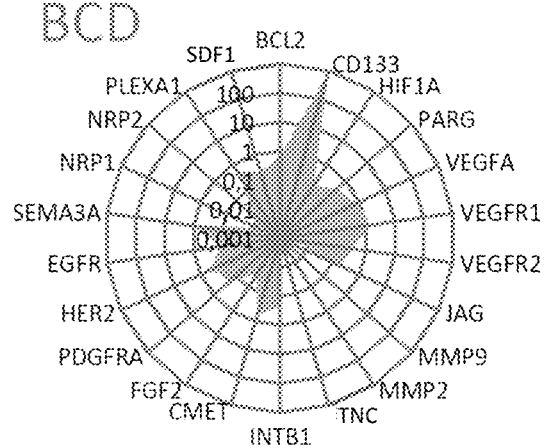
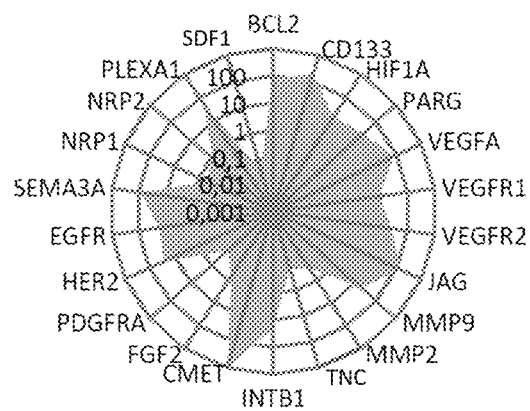
Figure 9D
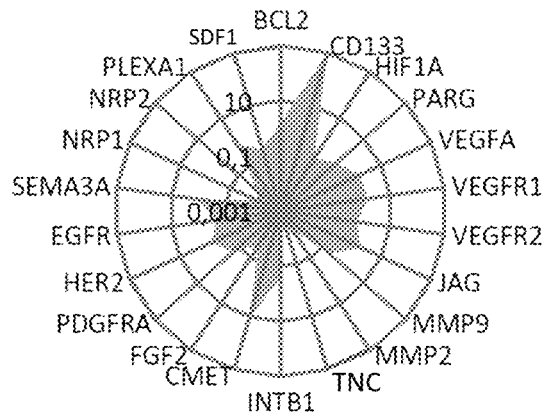
Figure 9E

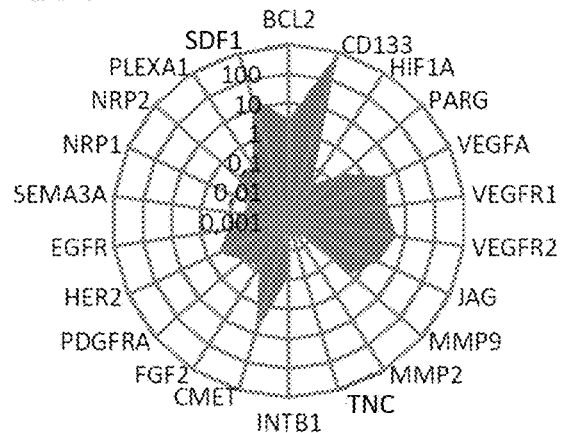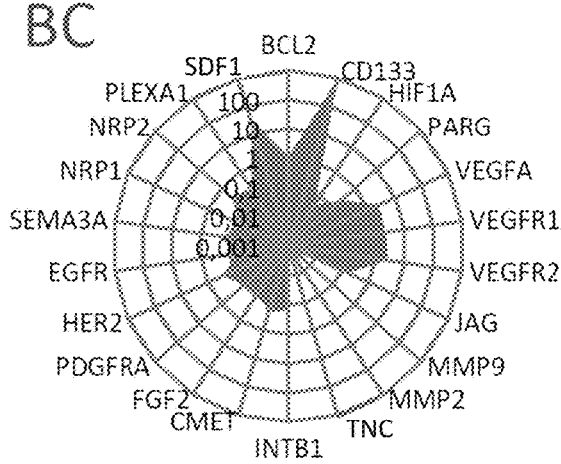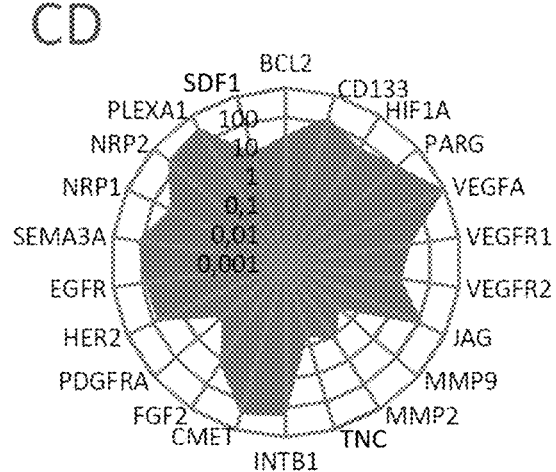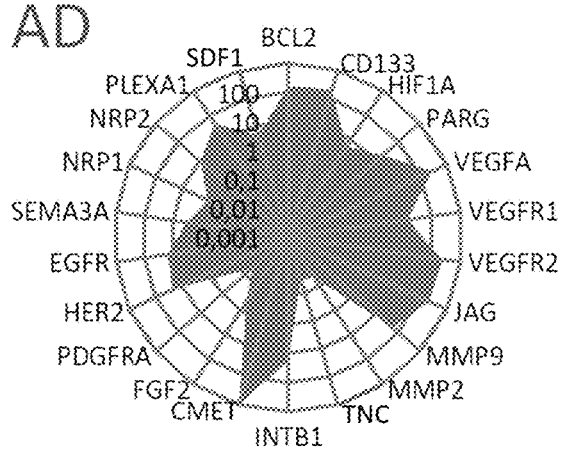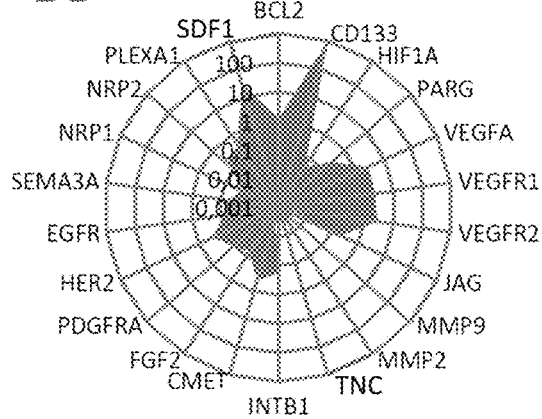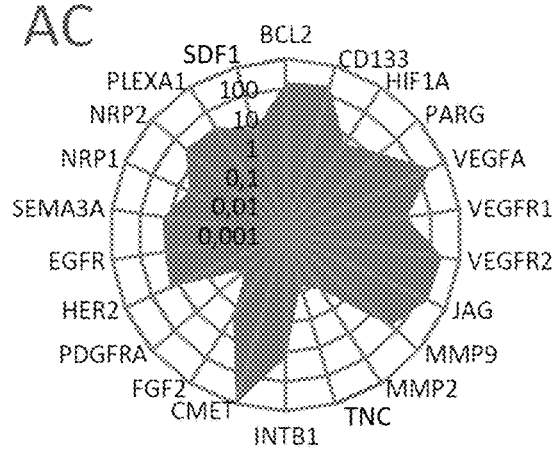
Figure 10C

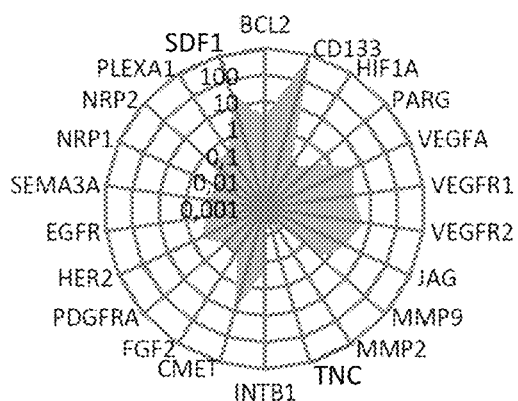
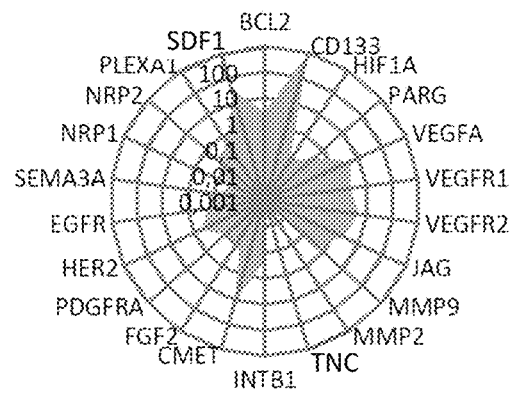
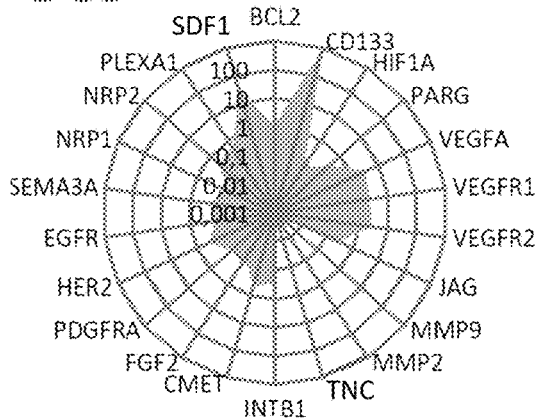
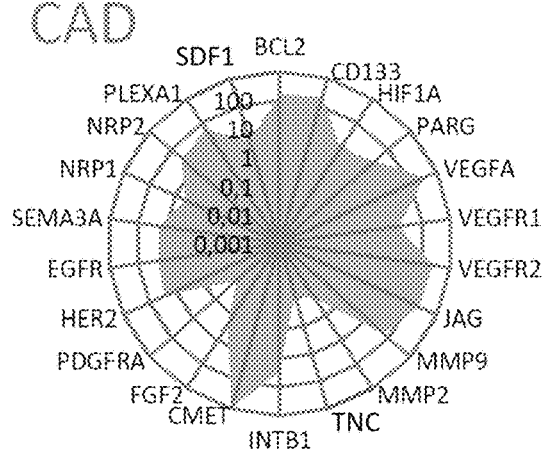
Figure 10D
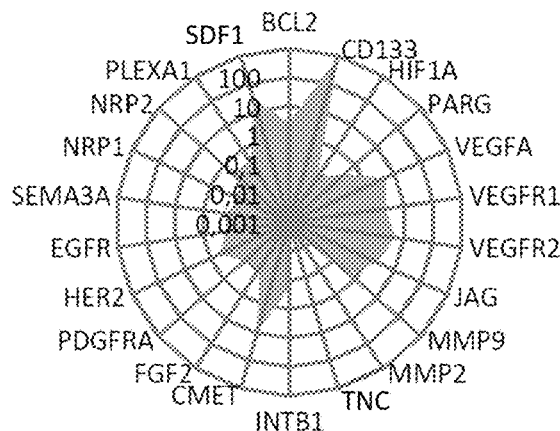
Figure 10E

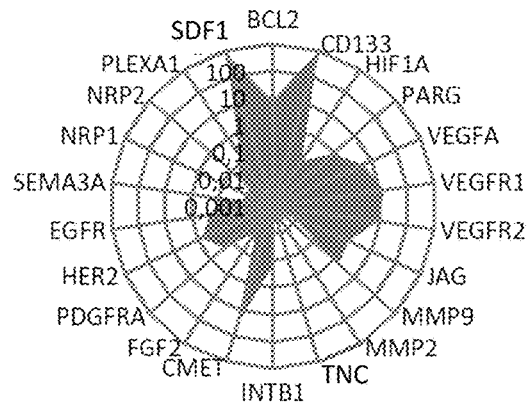
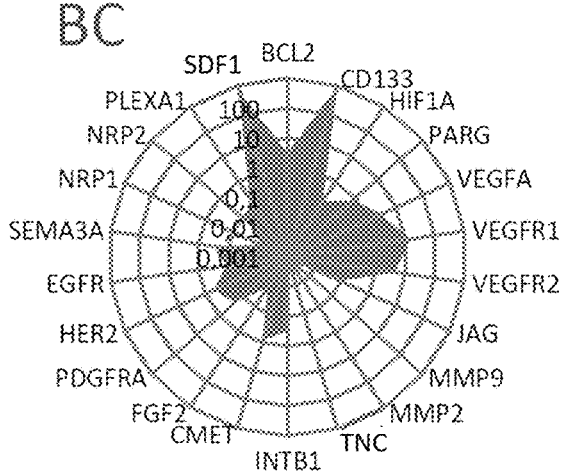
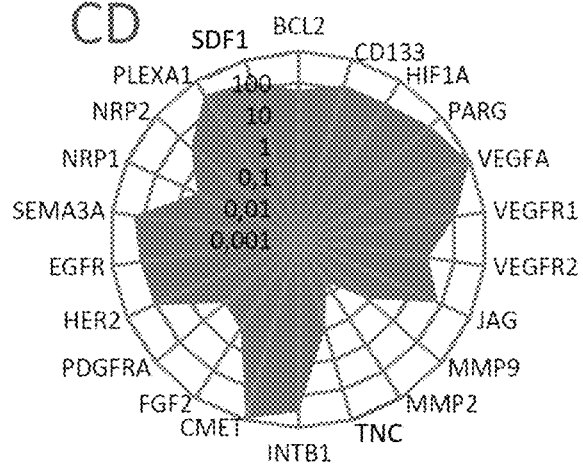
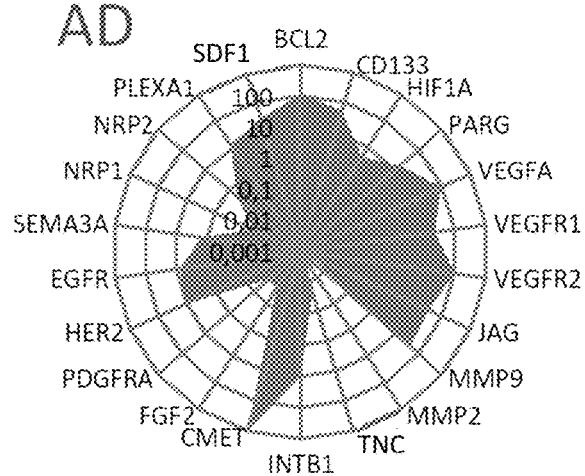
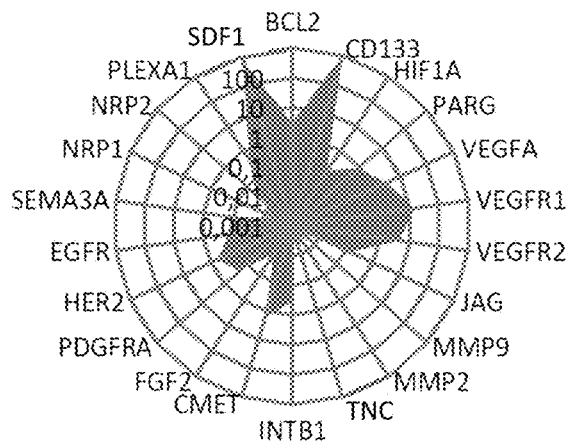
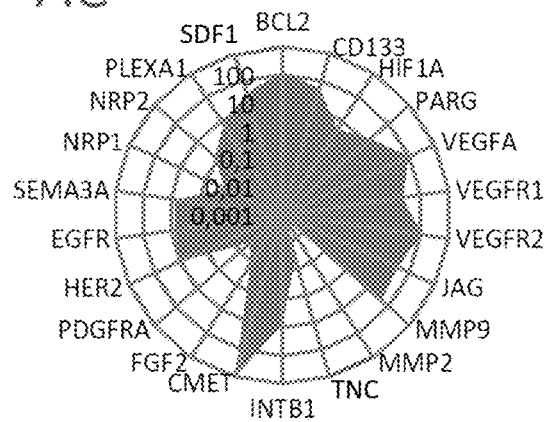
Figure 11C

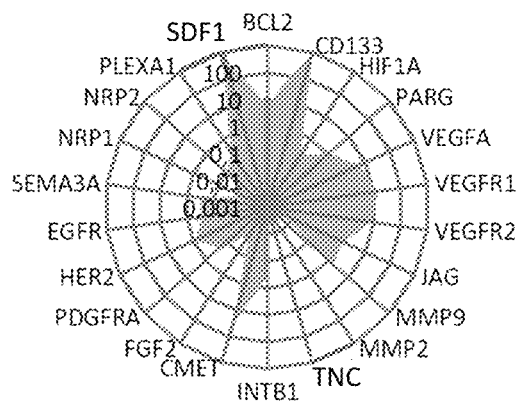
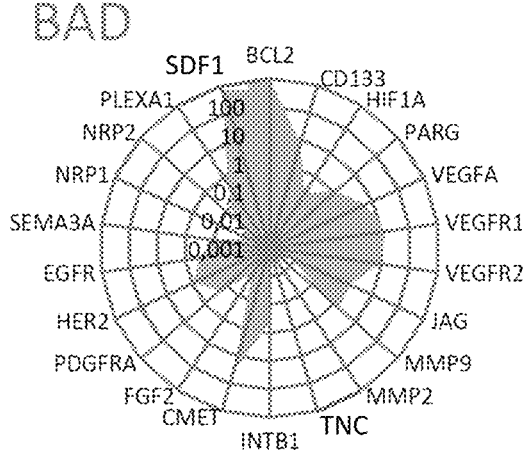
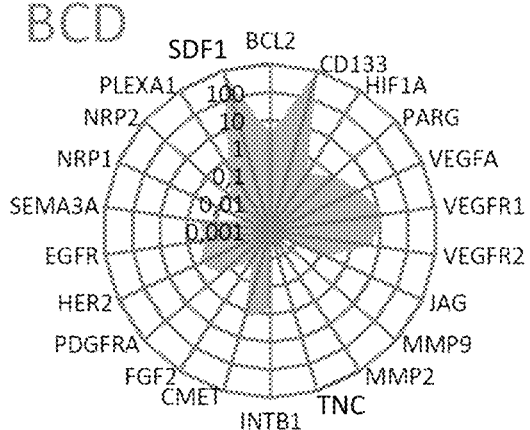
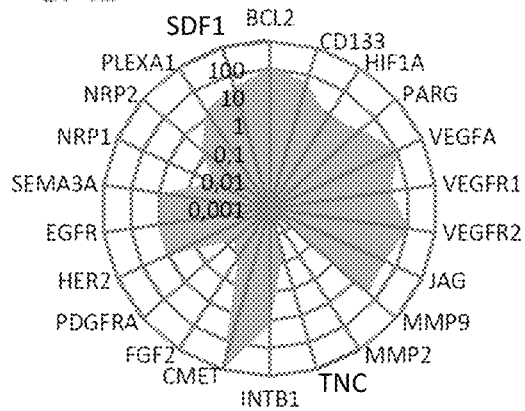
Figure 11D
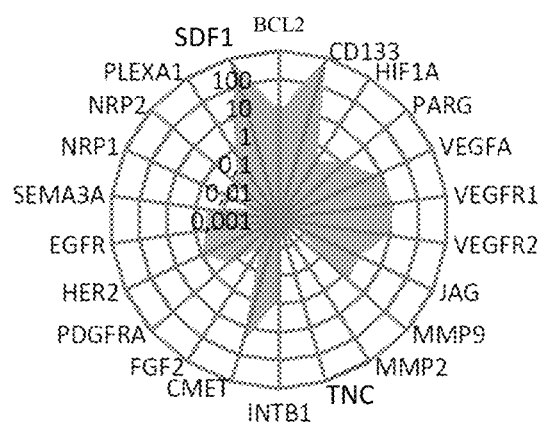
Figure 11E

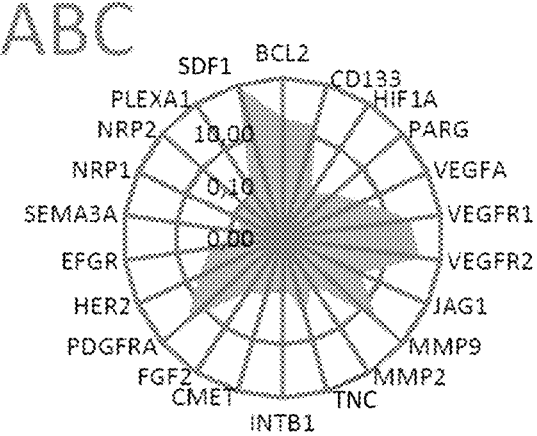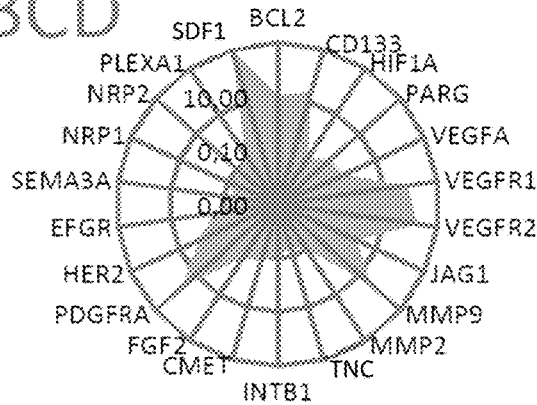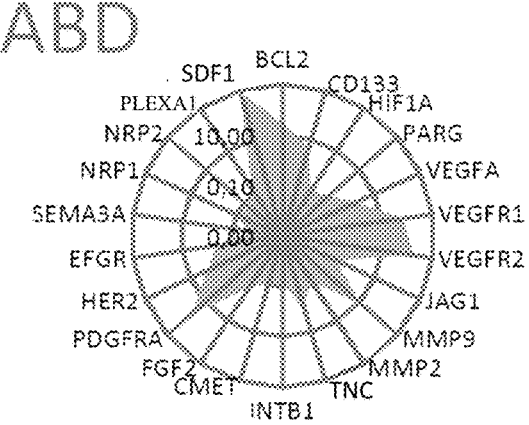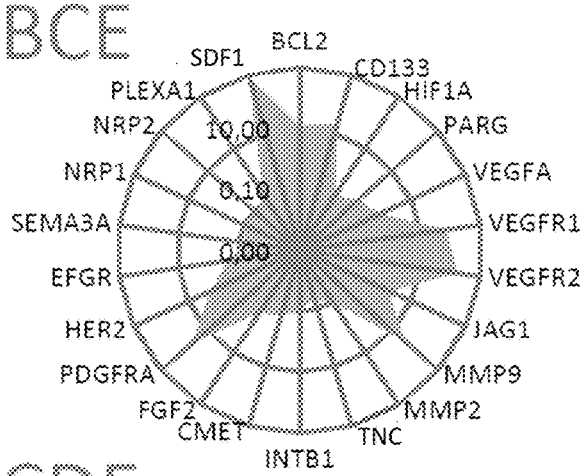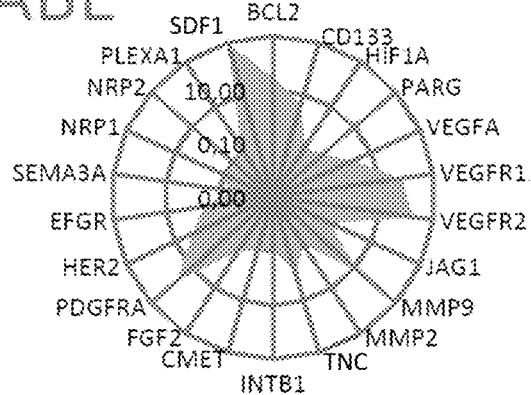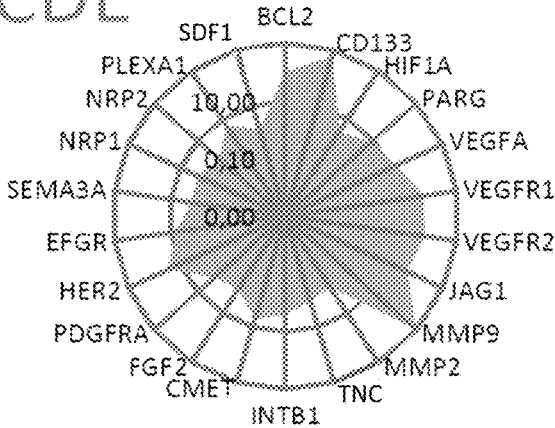
Figure 12D

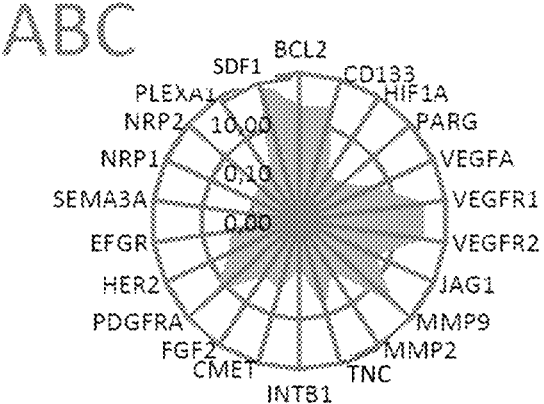
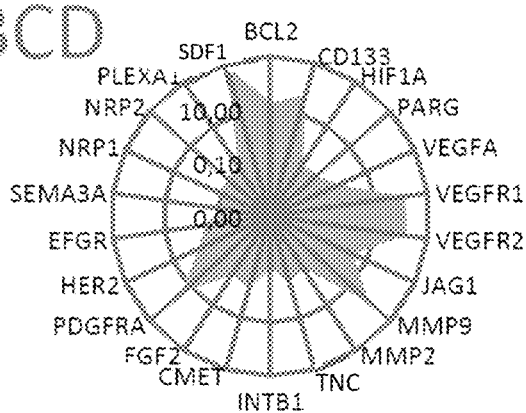
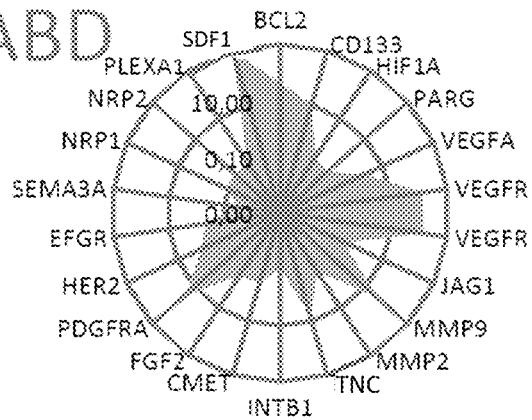
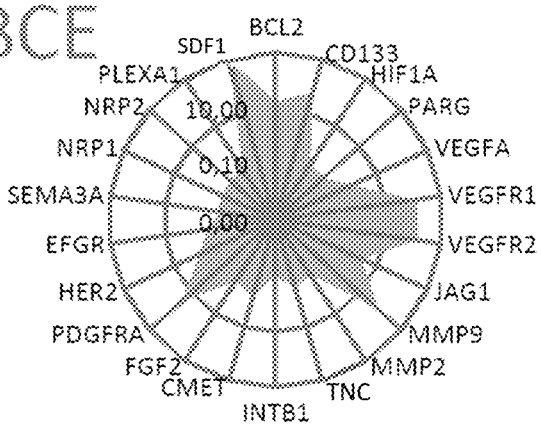
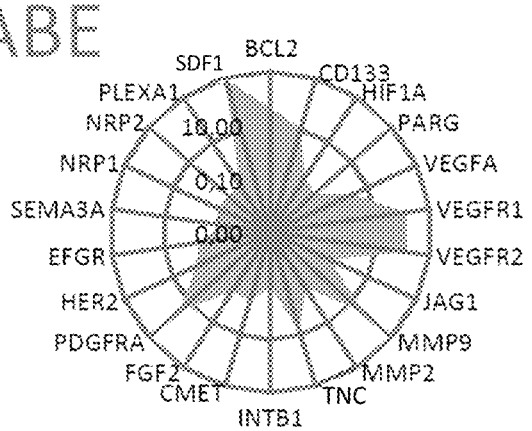
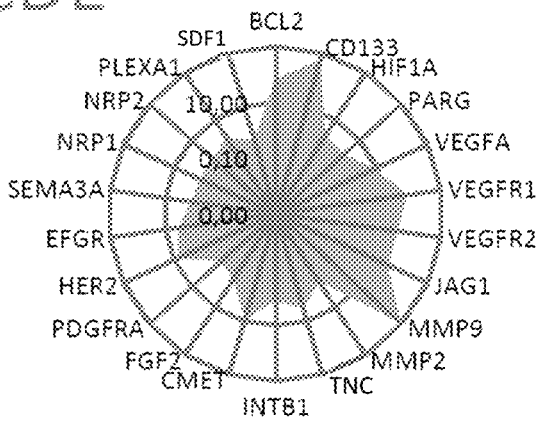
Figure 13D

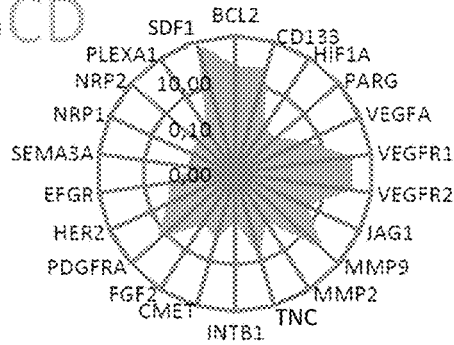
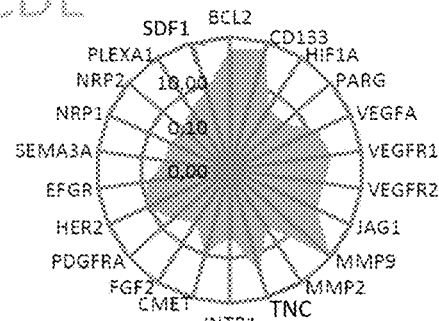
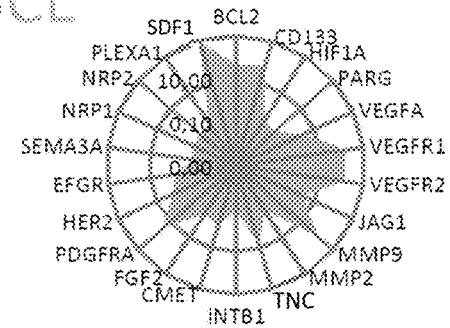
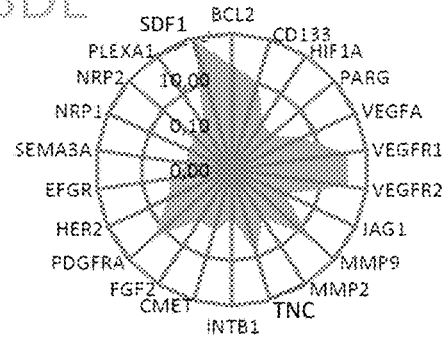
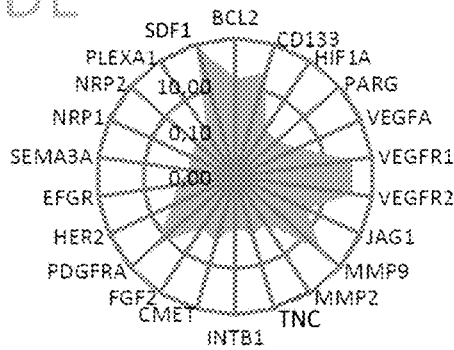
Figure 13E
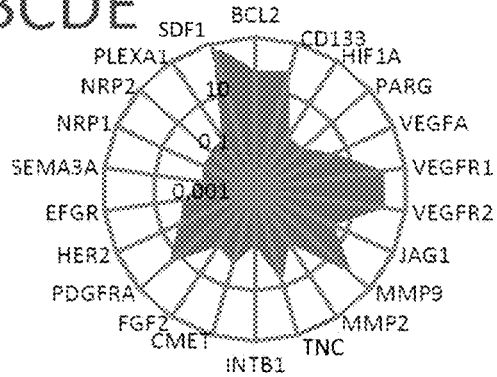
Figure 13F A
| Target | Rank | Score | Normalized score of restricted signature |
|---|---|---|---|
| CMET | 3 | 38,93 | 1000 |
| VEGFR1 | 4 | 14,82 | 380,80 |
| VEGFR2 | 5 | 8,529 | 219,10 |
| MMP9 | 8 | 1,743 | 44,78 |
| PARG | 9 | 1,45 | 37,27 |
| HER2 | 11 | 0,923 | 23,72 |
| EGFR | 14 | 0,421 | 10,82 |
| PDGFRA | 17 | 0,223 | 5,74 |
| MMP2 | 22 | 1E-04 | 3,74E-03 |
B
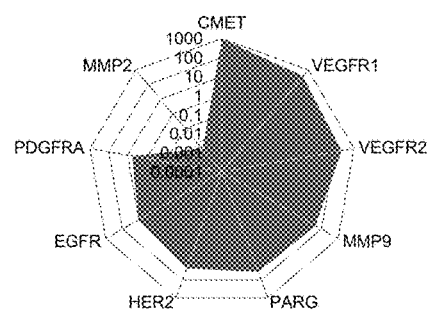
C
| Selected targets | VEGFR2 / VEGFR1 | HER2 | EGFR |
|---|---|---|---|
| Inhibitors | Cediranib 6 mg/kg; 5x/week (2x); P.O | Trastuzumab 1 mg/kg; 2x/week (3x) I.P | Cetuximab (Standard of care) 12,5 mg/kg; 1x/week (3x) I.P |
| Control | Vehicle of Cetuximab and Cediranib | | |
D
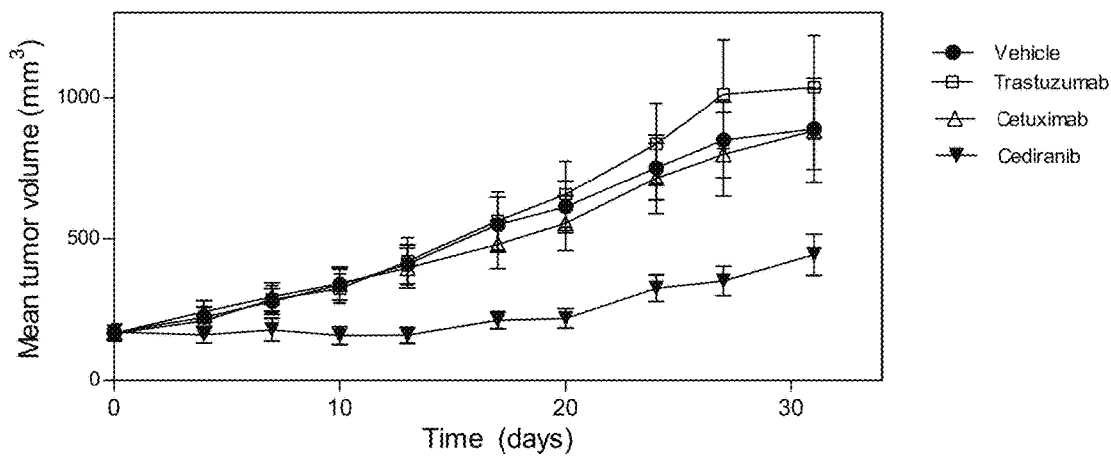
Figure 15

A
| Target | Rank | Score | Normalized score of restricted signature |
|---|---|---|---|
| MMP9 | 2 | 301,80 | 1000,00 |
| VEGFR2 | 3 | 84,87 | 281,23 |
| EGFR | 5 | 55,89 | 185,19 |
| HER2 | 6 | 54,93 | 182,00 |
| MMP2 | 10 | 17,90 | 59,33 |
| PARG | 16 | 7,33 | 24,30 |
| CMET | 17 | 5,81 | 19,25 |
| PDGFRA | 19 | 4,24 | 14,05 |
| VEGFR1 | 22 | 0,25 | 0,84 |
B
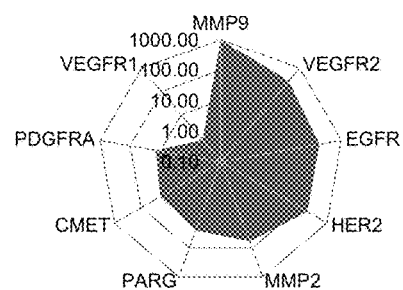
C
| Selected targets | MMP-9 | VEGFR2 / VEGFR1 | EGFR |
|---|---|---|---|
| Inhibitors | SB-3CT 25 mg/kg; 5x/week (2x) I.P | Cediranib 6 mg/kg; 5x/week (2x); P.O | Erlotinib 50 mg/kg; 1x/week (3x) P.O |
| Control | Temozolomide (Standard of care) 40 mg/kg; 5x/week I.V | | |
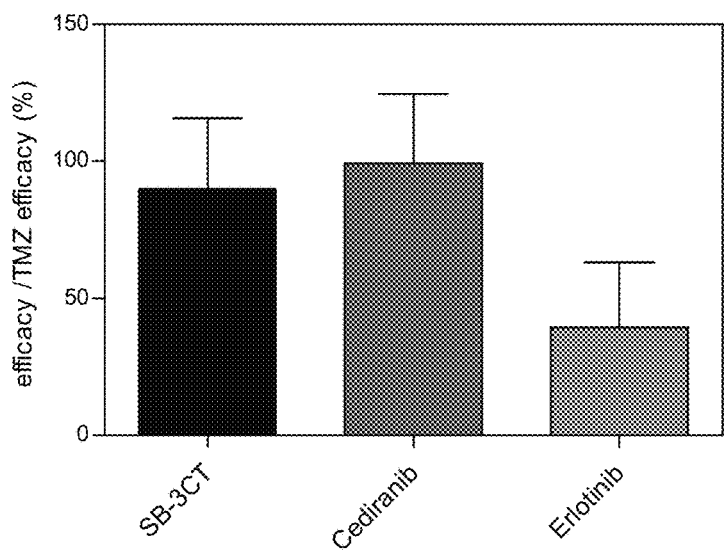
Figure 16

A
| Target | Rank | Score |
|---|---|---|
| VEGFR2 | 1 | 1000 |
| HER2 | 4 | 139,35 |
| PARG | 5 | 78,19 |
| EGFR | 6 | 55,90 |
| PDGFRA | 7 | 32,91 |
| VEGFR1 | 9 | 24,76 |
| MMP9 | 16 | 4,13 |
| CMET | 17 | 3,65 |
| MMP2 | 22 | 0,03 |
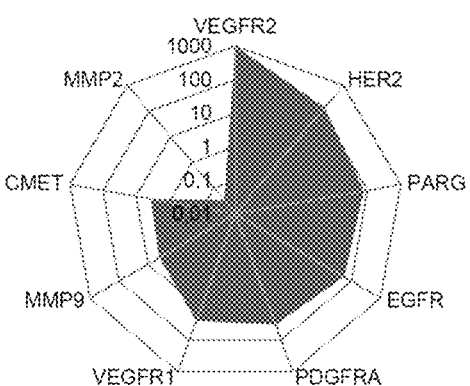
C
| Selected targets | VEGFR2 / VEGFR1 | EGFR |
|---|---|---|
| Inhibitors | Cediranib 6 mg/kg; 5x/week (3x); P.O | Erlotinib 50 mg/kg; 1x/week (3x) P.O |
| Control | Docetaxel (Standard of care) 20 mg/kg; 2 cycles of 1 injection every 3 weeks I.P | |
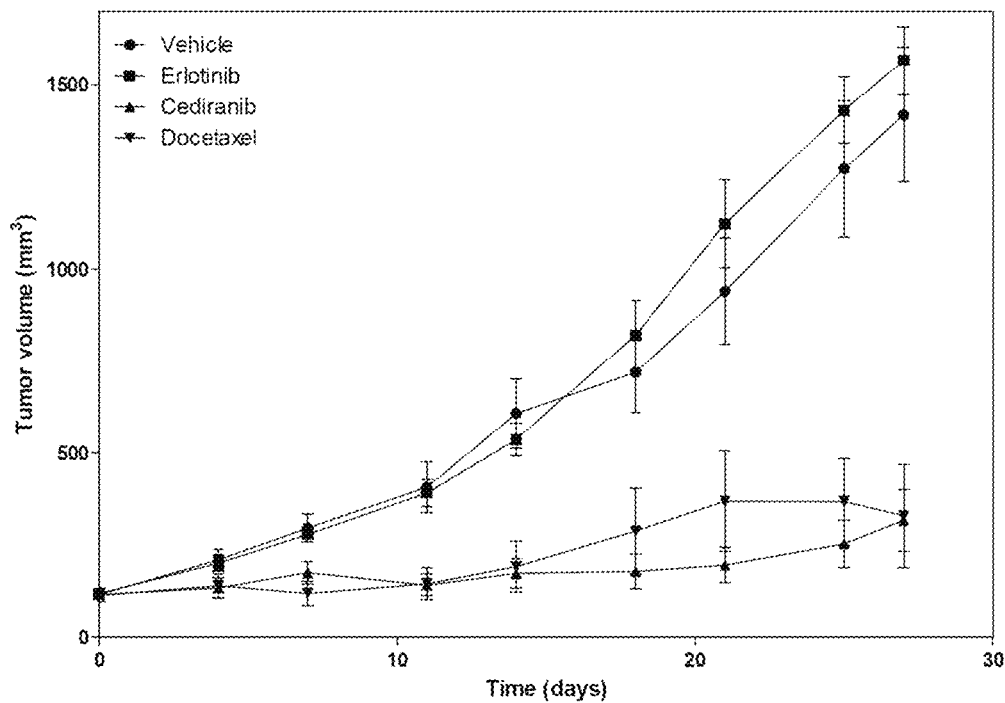
Figure 17

| 22 Targets | | |
|---|---|---|
| Target | Score | Rank |
| MMP9 | 1000 | 1 |
| VEGFA | 33.934575 | 2 |
| INTAV | 8.79008337 | 10 |
| FGFR1 | 7.98150592 | 11 |
| RET | 5.47143905 | 14 |
| PARG | 5.45599635 | 15 |
| INTB1 | 5.33842699 | 16 |
| ANGPT1 | 5.15516875 | 17 |
| EGFR | 4.88706882 | 18 |
| JAG1 | 3.18048228 | 22 |
| ERBB3 | 2.52997879 | 23 |
| HIF1A | 2.37921416 | 25 |
| HER2 | 2.23760593 | 26 |
| BCL2 | 1.94925591 | 28 |
| CMET | 1.60688689 | 31 |
| PDGFRB | 1.08122237 | 34 |
| FGFR2 | 0.79877917 | 38 |
| MMP2 | 0.61717748 | 39 |
| PDGFRA | 0.60489787 | 40 |
| SDF1 | 0.22804552 | 42 |
| VEGFR2 | 0.22254427 | 43 |
| CD133 | 0.18096127 | 44 |

+8 genes →

| 30 Targets | | |
|---|---|---|
| Target | Score | Rank |
| MMP9 | 1000 | 1 |
| VEGFA | 33.934575 | 2 |
| PD1 | 19.9165795 | 6 |
| INTAV | 8.79008337 | 10 |
| FGFR1 | 7.98150592 | 11 |
| RET | 5.47143905 | 14 |
| PARG | 5.45599635 | 15 |
| INTB1 | 5.33842699 | 16 |
| ANGPT1 | 5.15516875 | 17 |
| EGFR | 4.88706882 | 18 |
| ALK | 4.5933928 | 19 |
| AR | 3.95326692 | 20 |
| MEK1 | 3.26106383 | 21 |
| JAG1 | 3.18048228 | 22 |
| ERBB3 | 2.52997879 | 23 |
| HIF1A | 2.37921416 | 25 |
| HER2 | 2.23760593 | 26 |
| BCL2 | 1.94925591 | 28 |
| CRAF | 1.79790912 | 29 |
| ABL1 | 1.69602365 | 30 |
| CMET | 1.60688689 | 31 |
| MEK2 | 1.5986182 | 32 |
| FGFR3 | 1.20104596 | 33 |
| PDGFRB | 1.08122237 | 34 |
| FGFR2 | 0.79877917 | 38 |
| MMP2 | 0.61717748 | 39 |
| PDGFRA | 0.60489787 | 40 |
| SDF1 | 0.22804552 | 42 |
| VEGFR2 | 0.22254427 | 43 |
| CD133 | 0.18096127 | 44 |

+14 genes →

| 44 Targets | | |
|---|---|---|
| Target | Score | Rank |
| MMP9 | 1000 | 1 |
| VEGFA | 33.934575 | 2 |
| CEACAM-1 | 24.1055625 | 3 |
| CTLA4 | 19.9165795 | 4 |
| KIR | 19.9165795 | 5 |
| PD1 | 19.9165795 | 6 |
| PDL1 | 16.9944288 | 7 |
| CEACAM-5 | 16.2351216 | 8 |
| IDO1 | 13.538465 | 9 |
| INTAV | 8.79008337 | 10 |
| FGFR1 | 7.98150592 | 11 |
| B7-H3 | 6.19143757 | 12 |
| AKT1 | 5.9521477 | 13 |
| RET | 5.47143905 | 14 |
| FLT4 | 5.45599635 | 15 |
| CDK4 | 5.33842699 | 16 |
| CDK6 | 5.15516875 | 17 |
| EGFR | 4.88706882 | 18 |
| ALK | 4.5933928 | 19 |
| AR | 3.95326692 | 20 |
| MEK1 | 3.26106383 | 21 |
| JAG1 | 3.18048228 | 22 |
| ERBB3 | 2.52997879 | 23 |
| BRAF | 2.51492141 | 24 |
| HIF1A | 2.37921416 | 25 |
| HER2 | 2.23760593 | 26 |
| HDAC1 | 1.96267832 | 27 |
| BCL2 | 1.94925591 | 28 |
| CRAF | 1.79790912 | 29 |
| ABL1 | 1.69602365 | 30 |
| CMET | 1.60688689 | 31 |
| MEK2 | 1.5986182 | 32 |
| FGFR3 | 1.20104596 | 33 |
| PDGFRB | 1.08122237 | 34 |
| HDAC2 | 0.88956783 | 35 |
| IGF1R | 0.88719923 | 36 |
| MDM2 | 0.81676294 | 37 |
| FGFR2 | 0.79877917 | 38 |
| PI3KA | 0.61717748 | 39 |
| PDGFRA | 0.60489787 | 40 |
| KIT | 0.42025119 | 41 |
| SDF1 | 0.22804552 | 42 |
| VEGFR2 | 0.22254427 | 43 |
| CD133 | 0.18096127 | 44 |

Figure 18

METHOD FOR IDENTIFYING PERSONALIZED THERAPEUTIC STRATEGIES FOR PATIENTS AFFECTED WITH A CANCER

CROSS-REFERENCE TO RELATED APPLICATIONS

This application is the U.S. national stage application of International Patent Application No. PCT/EP2016/078353, filed Nov. 21, 2016, which claims the benefit of U.S. Provisional Patent Application No. 62/257,938, filed Nov. 20, 2015.

FIELD OF THE INVENTION

The present invention relates to the field of medicine, in particular of oncology. Especially, it provides new tools to select the best therapeutic option and thus provides new strategies for personalized therapy.

BACKGROUND OF THE INVENTION

Complexity is obviously the landmark of cell biology. Cells are constantly exposed to a multitude of environmental cues inducing proliferation, migration, differentiation or eventually cell death. In order to respond appropriately to this myriad of information cells build incredibly sophisticated signaling platforms composed of membrane proteins performing dynamic interactions. Such interactions ultimately trigger signal transduction pathways, the cellular communication highways responsible for linking external cues to changes in cell behavior, themselves being organized as hubs cross-linking pathways and thereby forming interacting intracellular networks. Inherent to this process is the ability of individual elements to interact not only with components of the same pathway but also with those from different ones.

Signaling pathways undergo constant remodeling as a direct consequence of adaptation of cells to environmental changes. Strikingly, this molecular plasticity is not restricted to normal cells but is instead also found in pathological contexts. Indeed, this adaptive property is one of the mechanisms used by tumor cells to survive and develop despite selective inhibition of important pathways regulating tumor growth. Consistently, the identification of these signaling pathways profoundly modified anti-cancer drug design over the last twenty years. The so called targeted therapies led to the identification and validation of efficient compounds such as small molecules, peptides or humanized antibodies. However, most of these powerful drugs failed to provide definitive curative effects, leading to tumor relapse.

One example is the case of patient with glioma, the most frequent and most severe primary brain tumors. The incidence of gliomas has increased over the past 20 years and is now reaching 5/100 000. The classification of these tumors remains difficult. The WHO classification provides a tumor grading (from I to IV) correlated with the aggressiveness of the tumor. The most severe glioma, which is also the most common, is glioblastoma (WHO grade IV) with a median of overall survival not exceeding 15 months. These tumors exhibit massive cell infiltration in the brain parenchyma and are highly vascularized. The standard first-line treatment is currently based on a maximum surgical resection, a concomitant chemoradiotherapy (60 Gray in 30 fractions, Temozolomide 75 mg/m$^2$/d for 6 weeks) followed by adjuvant chemotherapy with Temozolomide.

Consistently with the success obtained with anti-angiogenic drugs in several cancer indications, the humanized recombinant antibody Bevacizumab that prevents vascular endothelial growth factor (VEGF) receptor binding is used as second line treatment for patients with recurrent glioblastoma. Anti-angiogenic treatments have proven their efficacy in 30 to 60% of relapsing glioblastomas. However, the efficacy remains modest with time, since progression-free survival reaches 6 months while survival do not exceed 9 months (Omuro et al, Curr Opin Neurol. 2008 21(6):717-9). Various studies evaluated Bevacizumab in combination with temolozomide, irinotecan (including two different studies with opposing results), carboplatin, etoposide, cetuximab or erlotinib but none of the combinations have demonstrated superiority over Bevacizumab alone. Bevacizumab is therefore appearing as the best therapeutic option exhibiting impressive effect when compared to the results obtained over the past two decades with other drugs. This result is therefore leading to modify clinical practice by placing Bevacizumab as first line treatment. However, the compilation of Bevacizumab efficacy data shows that at best, response rates range from 11% to 79%, median progression-free survival (PFS) from 4.2 to 7.6 months and median overall survival (OS) from 4.6 to 12.6 months (Koukourakis G V, Recent Pat Inflamm Allergy Drug Discov. 2012 6(1): 70-7). In the recently published phase III trials, Avastin (bevacizumab) in Glioblastoma (AVAglio) and Radiation Therapy Oncology Group (RTOG) demonstrated a significant advantage for Bevacizumab treated patients in term of PFS but not of OS (Soffietti et al., Expert Rev Neurother. 2014 January; 14(1):1-3). Overall less than 50% of patients seem to benefit from Bevacizumab treatment.

Patient stratification is therefore a fundamental issue to improve therapeutic schemes. This issue is not restricted to glioma and glioblastoma patients. Indeed, management of colorectal cancer (CRC), which is the third most common cancer in males and females, is also experiencing a profound mutation thanks to the expansion of the therapeutic arsenal. Management is typically following a decision tree depending on tumor grading (Stinzing S., F1000Prime reports, 2014). While the first line treatment is obvious (5-fluorouracil combined with oxaliplatin (FOLFOX)/irinotecan (FOLFIRI) schemes), second line treatments are less clear and addition of anti-angiogenic is puzzling. A similar question arises for the use of anti-angiogenic compounds in prostate cancer (Bilusic & Wong, A S; J. Andrology, 2014).

Hence, while exemplifying the need of guided therapeutic approaches, these results illustrate how important is the possibility to develop tools helping the clinicians to select the best therapeutic option for a given patient.

SUMMARY OF THE INVENTION

The inventors developed a powerful tool which helps to identify the best therapeutic strategies for a patient affected with a cancer, in particular among available therapeutic arsenal. From a patient biopsy, the method of the invention allows to determine therapeutically targetable dominant signaling pathways in the cancer sample and thus to stratify patients or select the best therapeutic option.

Accordingly, in a first aspect, the present invention relates to a method for determining therapeutically targetable dominant signaling pathway(s) in a cancer sample from a subject affected with a solid cancer comprising
 a) providing the expression levels in said cancer sample of a set of genes representative of several therapeutically targetable signaling pathways;

b) determining the variations of each expression level provided in step a) compared to the expression level of the same gene
   in the organ from which said cancer originates,
   in at least one low grade or benign tumor tissue corresponding to said cancer and
   in at least one normal cellular subtype of the organ from which said cancer originates;
c) calculating a score for each of said genes that represents the global variation amplitude of the expression of said gene in the cancer sample compared to the expression of said gene in the organ from which said cancer originates, in low grade or benign tumor tissue(s) corresponding to said cancer and in normal cellular subtype(s) of the organ from which said cancer originates; and
d) ranking said genes according to said calculated scores, wherein the therapeutically targetable dominant signaling pathway(s) correspond to genes having the highest rank(s).

The method may further comprise, before step a), determining in said cancer sample the expression levels of said set of genes.

The method may further comprise, before step b), determining the expression levels of said set of genes
   in a sample of the organ from which said cancer originates,
   in a sample of at least one low grade or benign tumor tissue corresponding to said cancer, and/or
   in a sample of at least one normal cellular subtype of the organ from which said cancer originates.

The expression levels may be determined by measuring the quantity of the mRNA transcripts of the gene or their protein translation products, preferably by measuring the quantity of the mRNA transcripts. Preferably, the expression levels are determined by quantitative RT-PCR.

In step c), the score may be calculated using the following formula $$\text{score} = 2^{-\Delta\Delta Ct}(\text{organ}) + \sum_{k=1}^{n} [2^{-\Delta\Delta Ct}(\text{low grade or benign tumor tissue})_k] + \sum_{i=1}^{m} [2^{-\Delta\Delta Ct}(\text{cellular subtype})_i]$$

wherein
m and n are positive integers and are identical or different, and $\Delta\Delta Ct$(organ, low grade or benign tumor tissue or cellular subtype)=$\Delta Ct$(cancer sample)−$\Delta Ct$(organ, low grade or benign tumor tissue or cellular subtype)

where $\Delta Ct$ (cancer sample)=Ct (gene of interest in cancer sample)−Ct (housekeeping gene in cancer sample), and $\Delta Ct$ (organ, low grade or benign tumor tissue or cellular subtype) =Ct (gene of interest in organ, low grade or benign tumor tissue or cellular subtype)−Ct (housekeeping gene in organ, low grade or benign tumor tissue or cellular subtype).

The present invention also relates to a method for determining a treatment protocol for a subject affected with a solid cancer, the method comprising determining therapeutically targetable dominant signaling pathway(s) in a cancer sample from said subject according to the method of the invention and determining a treatment protocol that targets at least one dominant signaling pathway.

The present invention further relates to a method for selecting a subject affected with a solid cancer for therapy or determining whether a subject affected with a solid cancer is susceptible to benefit from a therapy, comprising determining therapeutically targetable dominant signaling pathway(s) in a cancer sample from said subject according to the method of the invention, wherein the subject is selected for the therapy or is susceptible to benefit from the therapy if the therapy targets at least one dominant signaling pathway.

The present invention further relates to a method for predicting clinical outcome of a subject affected with a solid cancer, comprising determining therapeutically targetable dominant signaling pathway(s) in a cancer sample from said subject according to the method of the invention, wherein the prognosis is good if the subject is treated with a therapy targeted at least one dominant pathway.

The present invention also relates to a method of predicting the sensitivity of a solid cancer to a therapy comprising determining therapeutically targetable dominant signaling pathways in a cancer sample from said subject according to the method of the invention, wherein said cancer is sensitive to the therapy if said therapy targets at least one of dominant signaling pathway.

In preferred embodiments, the cancer is selected from the group consisting of glioma, colon cancer, prostate cancer, skin cancer, lung cancer, pancreas cancer, liver cancer, kidney cancer, head and neck cancer and breast cancer, preferably from glioma, colon cancer and prostate cancer.

In an embodiment, the solid cancer is glioma and in step b) the variations of the expression levels of each of said genes provided in step a) are determined compared to the expression levels of said genes in normal brain, in astrocytoma grade II, and in normal brain astrocytes and/or normal brain oligodendrocytes.

In another embodiment, the solid cancer is colon cancer and in step b) the variations of the expression levels of each of said genes provided in step a) are determined compared to the expression levels of said genes in normal colon and/or in colonic smooth muscle cells, in non-cancerous polyps or low grade colon tumor, and in normal colonic epithelial cells.

In a further embodiment, the solid cancer is prostate cancer and in step b) the variations of the expression levels of each of said genes provided in step a) are determined compared to the expression levels of said genes in normal prostate, in glandular hyperplasia of prostate, and in normal prostate epithelial cells, prostate microvascular endothelial cells and/or prostate fibroblasts.

The present invention also relates to a kit comprising a pair of primers, a probe or an antibody specific to each of the genes representative of therapeutically targetable signaling pathways, and the use of such a kit for (i) determining the therapeutically targetable dominant signaling pathway(s) in a cancer sample from a subject affected with a solid cancer, (ii) determining a treatment protocol for a subject affected with a solid cancer, (iii) selecting a subject affected with a solid cancer for a therapy, (iv) determining whether a subject affected with a solid cancer is susceptible to benefit from a therapy, (v) predicting clinical outcome of a subject affected with a solid cancer, (vi) treating a patient affected with a solid cancer and/or (vii) predicting the sensitivity of a solid cancer to a therapy.

BRIEF DESCRIPTION OF THE DRAWINGS

FIG. 1: Determination of therapeutically targetable dominant signaling pathways in a glioblastoma biopsy. (A) The score for each gene is obtained when normalizing data to the brain, to astrocytes, to oligodendrocytes and to low grade astrocytoma. (B) The obtained values are then ranked and converted into arbitrary units. (C) Radar mode showing the log of the Normalized scores.

FIGS. 6A, B, C and D refer to normalization by comparison to the expression in the brain, astrocytes, oligodendrocytes and low grade astrocytoma, respectively.

FIGS. 7A-7E: Personal signature obtained from a GBM biopsy (HB6). Radar mode of raw data (FIG. 7A), with one step of normalization (FIG. 7B), with two steps of normalization (FIG. 7C), with three steps of normalization (FIG. 7D), and with four steps of normalization (FIG. 7E). FIGS. 7A, B, C and D refer to normalization by comparison to the expression in the brain, astrocytes, oligodendrocytes and low grade astrocytoma, respectively.

FIGS. 8A, B, C and D refer to normalization by comparison to the expression in the brain, astrocytes, oligodendrocytes and low grade astrocytoma, respectively.

FIGS. 9A-9E: Personal signature obtained from a CC biopsy (Colon 1). Radar mode of raw data (FIG. 9A), with one step of normalization (FIG. 9B), with two steps of normalization (FIG. 9C), with three steps of normalization (FIG. 9D), and with four steps of normalization (FIG. 9E). FIGS. 9A, B, C and D refer to normalization by comparison to the expression in normal colon, human epithelial colonic cells, microvascular colonic cells and low grade colon tumors, respectively.

FIGS. 10A-10E: Personal signature obtained from a CC biopsy (Colon 4). Radar mode of raw data (FIG. 10A), with one step of normalization (FIG. 10B), with two steps of normalization (FIG. 10C), with three steps of normalization (FIG. 10D), and with four steps of normalization (FIG. 10E). FIGS. 10A, B, C and D refer to normalization by comparison to the expression in normal colon, human epithelial colonic cells, microvascular colonic cells and low grade colon tumors, respectively.

FIGS. 11A-11E: Personal signature obtained from a CC biopsy (Colon 8). Radar mode of raw data (FIG. 11A), with one step of normalization (FIG. 11B), with two steps of normalization (FIG. 11C), with three steps of normalization (FIG. 11D), and with four steps of normalization (FIG. 11E). FIGS. 11A, B, C and D refer to normalization by comparison to the expression in normal colon, human epithelial colonic cells, microvascular colonic cells and low grade colon tumors, respectively.

FIGS. 12A-12F: Personal signature obtained from a prostate adenocarcinoma biopsy (1). Radar mode of raw data (FIG. 12A), with one step of normalization (FIG. 12B), with two steps of normalization (FIG. 12C), with three steps of normalization (FIG. 12D), with four steps of normalization (FIG. 12E) and with five steps of normalization (FIG. 12F). FIGS. 12A, B, C, D and E refer to normalization by comparison to the expression in normal prostate, epithelial cells, prostate microvascular endothelial cells, prostate fibroblasts and low grade prostate cancer, respectively.

FIGS. 13A-13F: Personal signature obtained from a prostate adenocarcinoma biopsy (2). Radar mode of raw data (FIG. 13A), with one step of normalization (FIG. 13B), with two steps of normalization (FIG. 13C), with three steps of normalization (FIG. 13D), with four steps of normalization (FIG. 13E) and with five steps of normalization (FIG. 13F). FIGS. 13A, B, C, D and E refer to normalization by comparison to the expression in normal prostate, epithelial cells, prostate microvascular endothelial cells, prostate fibroblasts and low grade prostate cancer, respectively.

FIGS. 14A, B, C, D and E refer to normalization by comparison to the expression in normal prostate, epithelial cells, prostate microvascular endothelial cells, prostate fibroblasts and low grade prostate cancer, respectively.

FIG. 15: Scores (A) and radar mode (B) of the personal restricted signature obtained from a CC model (CR-IC-028M). Inhibitors and therapeutic protocols used in in vivo CC models (C). Evolution of the tumor growth in mice treated with trastuzumab, cetuximab, cediranib or the vehicle (D).

FIG. 16: Scores (A) and radar mode (B) of the personal restricted signature obtained from a GBM model (HIB21). Inhibitors and therapeutic protocols used in in vivo GBM models (C). Efficacy of SB-3CT, cediranib and erlotinib compared to TMZ (%) (D).

FIG. 17: Scores (A) and radar mode (B) of the personal restricted signature obtained from a PC model (HID-28). Inhibitors and therapeutic protocols used in in vivo PC models (C). Evolution of the tumor growth in mice treated with Cediranib, Erlotinib, Docetaxel or the vehicle (D).

FIG. 18: Signatures comprising 22 genes and 8 (30 genes) or 22 (44 genes) additional genes obtained from a sample of brain tumor.

DETAILED DESCRIPTION OF THE INVENTION

Definition

Figure 2:
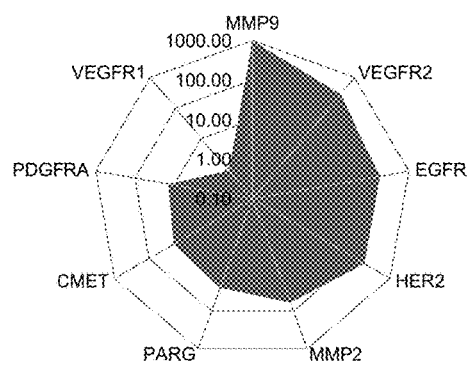
FIG. 2: Scores (A) and radar mode (B) of the restricted signature comprising only target genes for which a drug is available during this study.

The term "sample", as used herein, means any sample containing cells derived from a subject, preferably a sample which contains nucleic acids. Examples of such samples include fluids such as blood, plasma, saliva, urine, cerebrospinal fluid and seminal fluid samples as well as biopsies, organs, tissues or cell samples. The sample may be treated prior to its use. It may be fresh, frozen or fixed (e.g. formaldehyde or paraffin fixed) sample.

The term "cancer sample" or "tumor sample" refers to any sample containing tumoral cells derived from a patient. Preferably, the sample contains only tumoral cells. In preferred embodiments, the cancer sample is a biopsy or is derived from a biopsy obtained from the patient during surgery.

As used herein, the term "subject" or "patient" refers to an animal, preferably to a mammal, even more preferably to a human, including adult, child and human at the prenatal stage.

The term "cancer" or "tumor", as used herein, refers to the presence of cells possessing characteristics typical of cancer-causing cells, such as uncontrolled proliferation, immortality, metastatic potential, rapid growth and proliferation rate, and certain characteristic morphological features. This term includes early stage, localized, cancer; later stage, locally advanced cancer; and metastatic stage cancer. Preferably, this term refers to a solid cancer. More preferably, the cancer is selected from the group consisting of glioma, colon, prostate, breast, kidney, lung cancer, gastro-intestinal cancer, melanoma, head and neck tumors. Even more preferably, the cancer is selected from glioma, prostate cancer and colon cancer.

The term "glioma" refers to a tumor that arises from glial cells or their precursors of the brain or spinal cord. Gliomas are histologically defined based on whether they exhibit primarily astrocytic or oligodendroglial morphology, and are graded by cellularity, nuclear atypia, necrosis, mitotic figures, and microvascular proliferation. Astrocytomas are of two main types: high-grade and low-grade. High-grade tumors grow rapidly, are well-vascularized, and can easily spread through the brain. Low-grade astrocytomas are usually localized and grow slowly over a long period of time. High-grade tumors are much more aggressive, require very intensive therapy, and are associated with shorter survival lengths of time than low grade tumors. These tumors can occur anywhere in the brain and spinal cord. Some of the more common low-grade astrocytomas are: juvenile pilocytic astrocytoma, fibrillary astrocytoma, pleomorphic xantroastrocytoma and desembryoplastic neuroepithelial tumor. The two most common high-grade astrocytomas are anaplastic astrocytoma and glioblastoma multiform (or glioblastoma) (GBM). In preferred embodiments, the cancer is glioma and in particular glioblastoma.

The term "prostate cancer" refers to any cancer of the prostate gland. The prostate cancer may be adenocarcinoma, sarcoma, small cell carcinoma, neuroendocrine tumor or transitional cell carcinoma. Preferably, the prostate cancer is adenocarcinoma.

As used herein, the term "colon cancer" refers to a cancer arising in the large intestine (including both the colon and rectum) of any histologic type, including but not limited to malignant epithelial tumors. The colon cancer may be adenocarcinoma, carcinoid tumor, mucinous adenocarcinoma (also termed colloid adenocarcinoma), signet ring adenocarcinoma, scirrhous tumor, carcinoma simplex or sarcoma. Preferably, the colon cancer is adenocarcinoma.

As used herein, the term "skin cancer" refers to cancer arising in the skin of any histological type, including but not limited to basal cell carcinoma, Merkel cell carcinoma, squamous cell carcinoma or melanoma. Preferably, the skin cancer is melanoma.

As used herein, the term "lung cancer" refers to a cancer arising in the lung of any histological type, including but not limited to small cell lung cancer or non small cell lung cancer (including adenocarcinoma, squamous cell carcinoma, large cell carcinoma). Preferably, the cancer is non-small cell lung cancer.

As used herein, the term "pancreas cancer" refers to a cancer arising in the pancreas of any histological type, including but not limited to exocrine tumors and endocrine tumors. The pancreas tumor may be adenocarcinoma, acinar cell carcinoma, intraductal papillary-mucinous neoplasm, mucinous cystadenocarcinoma, glucagonoma, insulinoma, multiple endocrine neoplasia type-1. Preferably, the pancreas cancer is an exocrine tumor.

As used herein, the term "liver cancer" refers to a cancer arising in the liver, of any histological type, including but not limited to hepatocellular carcinoma, fibrolamellar carcinoma, cholangiocarcinoma. Preferably, the liver cancer is hepatocellular carcinoma.

As used herein, the term "kidney cancer" refers to a cancer arising in the kidney, of any histological type, including but not limited to renal cell cancer (also called renal cell adenocarcinoma or hypernephroma). The renal cell cancer may be clear cell renal cancer, papillary renal cell cancer, chromophobe renal cell cancer. Preferably the kidney cancer is renal cell carcinoma.

As used herein, the term "head and neck cancer" refers to a cancer arising in the tissues and organs of the head and neck. They include cancers of the larynx, throat, lips, mouth, nose and salivary glands of any histological types. The head and neck tumor may be squamous cell cancers (squamous cell carcinomas), adenocarcinomas or sarcomas. Preferably, the head and neck tumor is a squamous cell carcinoma.

As used herein, the term "breast cancer" refers to any cancer of the mammary gland of any histological type. The breast cancer may be ductal carcinoma in situ, invasive ductal carcinoma, invasive lobular carcinoma. Preferably, the breast cancer is an invasive breast cancer.

As used herein, the term "treatment", "therapy", "treat" or "treating" refers to any act intended to ameliorate the health status of patients such as therapy, prevention, prophylaxis and retardation of the disease. In certain embodiments, such term refers to the amelioration or eradication of a disease or symptoms associated with a disease. In other embodiments, this term refers to minimizing the spread or worsening of the disease resulting from the administration of one or more therapeutic agents to a subject with such a disease. In preferred embodiments, the therapy is a chemotherapy. As used herein, the term "chemotherapeutic treatment" or "chemotherapy" refers to a cancer therapeutic treatment using chemical or biochemical substances, in particular using one or several antineoplastic agents.

By a "therapeutically efficient amount" is intended an amount of therapeutic agent(s) administered to a patient that is sufficient to constitute a treatment of a cancer.

As used herein, the term "poor prognosis" refers to a decreased patient survival and/or an early disease progression and/or an increased disease recurrence and/or an increased metastasis formation. Conversely, the term "good prognosis" refers to an increased patient survival and/or a delayed disease progression and/or a decreased disease recurrence and/or a decreased metastasis formation.

As used herein, the term "signaling pathway" refers to any intra- or intercellular process by which cells converts one kind of signal or stimulus into another, most often involving ordered sequences of biochemical reactions out- and inside the cell, that are carried out by enzymes and linked through hormones and growth factors (intercellular), as well as second messengers (intracellular).

A "therapeutically targetable signaling pathway" is a signaling pathway that can be modulated by a therapeutic arsenal, preferably already available or under development.

The term "marker" as used herein, refers to a differentially expressed gene whose expression pattern can be determined and correlated with a known condition, in particular with the activation of a signaling pathway.

The methods of the invention as disclosed herein, may be in vivo, ex vivo or in vitro methods, preferably in vitro methods.

The inventors developed a powerful tool which helps to identify the best therapeutic strategies for a patient affected with a cancer, in particular among available therapeutic arsenal. Indeed, this tool is intended to provide clinicians a decision tool helping to select which tumor signaling pathway(s) has/have to be targeted for best therapeutic effect. As illustrated in the experimental section, the inventors demonstrated that a personal predictive classification may be obtained from a patient biopsy by determining the expression levels of a set of genes representative of therapeutically targetable pathway(s) and applying a multi-step normalization procedure. They showed that this sequential normalization is mandatory to take into account the heterogeneity and complexity of tumors and to provide reliable results.

Accordingly, in a first aspect, the present invention relates to a method for determining dominant signaling pathways in a tumor that could be targeted by a therapy, i.e. therapeutically targetable dominant signaling pathways, in a cancer sample from a subject affected with a cancer.

The method comprises
a) providing the expression levels in a cancer sample from the subject of a set of genes representative of several therapeutically targetable signaling pathways;
b) determining the variations of the expression levels of each of said genes provided in step a) compared to the expression levels of said genes
   in the organ from which said cancer originates,
   in at least one low grade or benign tumor tissue corresponding to said cancer and
   in at least one normal cellular subtype of the organ from which said cancer originates;
c) calculating a score for each of said genes that represents the global variation amplitude of the expression of said gene in the cancer sample compared to the expression of said gene in the organ from which said cancer originates, in low grade or benign tumor tissue(s) corresponding to said cancer and normal cellular subtype(s) of the organ from which said cancer originates; and
d) ranking said genes according to said calculated scores, wherein the therapeutically targetable dominant signaling pathway(s) correspond to genes having the highest rank(s).

In an embodiment, the method further comprises, before step a), determining in said cancer sample the expression levels of said genes representative of several therapeutically targetable signaling pathways. Optionally, the method may further comprise providing a cancer sample from the subject, e.g. a cancer sample obtained from the patient during surgery.

The expression level of genes may be determined by any method known by the skilled person. In particular, expression level may be determined (i) by measuring the quantity of mRNA and/or (ii) by measuring the quantity of encoded protein.

Methods for determining the quantity of mRNA are well known in the art and include, but are not limited to, quantitative or semi-quantitative RT-PCR, real time quantitative or semi-quantitative RT-PCR, Nanostring technology, sequencing based approaches or transcriptome approaches.

The nucleic acid contained in the sample (e.g., cells or tissue prepared from the patient) may be first extracted according to standard methods, for example using lytic enzymes or chemical solutions or extracted by nucleic-acid-binding resins following the manufacturer's instructions. These nucleic acids may be frozen to be stored before use.

The extracted mRNA may be then detected by hybridization (e.g., Northern blot analysis) and/or amplification (e.g., RT-PCR). Quantitative or semi-quantitative RT-PCR is preferred. Real-time quantitative or semi-quantitative RT-PCR is particularly advantageous. Preferably, primer pairs were designed in order to overlap an intron, so as to distinguish cDNA amplification from putative genomic contamination. Such primers may be easily designed by the skilled person. Other methods of Amplification include, but are not limited to, ligase chain reaction (LCR), transcription-mediated amplification (TMA), strand displacement amplification (SDA) and nucleic acid sequence based amplification (NASBA).

Alternatively, the quantity of mRNA may also be measured using the Nanostring's NCOUNTER™ Digital Gene Expression System (Geiss et al. 2008 Nat. Biotechnol. 26:317-325) which captures and counts individual mRNA transcripts by a molecular bar-coding technology and is commercialized by Nanostring Technologies, or the QuantiGene® Plex 2.0 Assay (Affymetrix).

The quantity of mRNA may further be determined using approaches based on high-throughput sequencing technology such as RNA-Seq (Wang et al. Nat Rev Genet. 2009 January; 10(1): 57-63) or sequencing technologies using microfluidic systems.

The expression level of a gene may also be determined by measuring the quantity of mRNA by transcriptome approaches, in particular by using DNA microarrays. To determine the expression level of a gene, the sample, optionally first subjected to a reverse transcription, is labelled and contacted with the microarray in hybridization conditions, leading to the formation of complexes between target nucleic acids that are complementary to probe sequences attached to the microarray surface. The labelled hybridized complexes are then detected and can be quantified or semi-quantified. Labelling may be achieved by various methods, e.g. by using radioactive or fluorescent labelling. Many variants of the microarray hybridization technology are available to the man skilled in the art. Examples of DNA biochips suitable to measure the expression level of the genes of interest include, but are not limited to, Human Genome U133 Plus 2.0 array (Affymetrix)

Next Generation Sequencing methods (NGS) may also be used.

In a particular embodiment, the quantity of mRNA is measured by quantitative RT-PCR.

Methods for measuring the quantity or the activity of the encoded protein are also well-known by the skilled person and the choice of the method depends on the encoded protein. Usually, these methods comprise contacting the sample with a binding partner capable of selectively interacting with the protein present in the sample. The binding partner is generally a polyclonal or monoclonal antibody, preferably monoclonal. The quantity of protein is measured by semi-quantitative Western blots, immunochemistry (enzyme-labeled and mediated immunoassays, such as ELISAs, biotin/avidin type assays, radioimmunoassay, immunoelectrophoresis or immunoprecipitation) or by protein or antibody arrays. In a particular embodiment, the protein expression level is assessed by reverse-phase protein microarray (RPPM). The protein expression level may also be assessed by immunohistochemistry on a tissue section of the cancer sample (e.g. frozen or formalin-fixed paraffin embedded material). The reactions generally include revealing labels such as fluorescent, chemiluminescent, radioactive, enzymatic labels or dye molecules, or other methods for detecting the formation of a complex between the antigen and the antibody or antibodies reacted therewith. Specific activity assays may also be used, in particular when the encoded protein is an enzyme.

In preferred embodiments, expression levels of genes are determined by measuring the quantity of mRNA by quantitative RT-PCR.

Preferably, expression levels of genes provided in step a) and/or determined as described above, are normalized to a reference expression level, preferably to the expression level of one or more housekeeping (or control or reference) genes.

As used herein, the term "housekeeping gene" refers to a gene involved in basic functions needed for maintenance of the cell. Housekeeping genes are transcribed at a relative constant level and are thus used to normalize expression levels of genes that vary across different samples. Examples of housekeeping genes include, but are not limited to, GAPDH (Gene ID NCBI: 2597), ribosomal 18S gene (RNA18S5, Gene ID NCBI: 100008588), beta-glucuronidase, actin, tubulin, ubiquitin, RPLPO, HPRT1 and B2M genes.

In a particular embodiment, the expression level of each gene is determined by measuring the amount of mRNA by quantitative RT-PCR and is normalized with respect to that of a housekeeping gene, preferably the ribosomal 18S (R18S) and/or GAPDH reference gene, by the $2^{-\Delta Ct}$ method.

The set of genes representative of therapeutically targetable signaling pathways may be chosen by the skilled person based on the indications below. Optionally, the method may further comprise before step a), determining the set of genes representative of therapeutically targetable signaling pathways.

Signaling pathways ranked thanks to the method of the invention may vary, in particular according to the type of cancer and the development of new therapeutic targets. The skilled person may choose genes representing a therapeutically targetable signaling pathway on the basis of i) a good knowledge of related biological functions, ii) a correlation between expression level and aggressiveness of the tumor, and/or iii) the existence of a therapeutic arsenal already in clinical use (including off-label drugs).

Preferably, the set of genes representative of therapeutically targetable signaling pathways comprises markers of the tumor status including markers of inflammation, cancer stem cells, hypoxia, cell death, posttranslational modifications and proliferation; markers of the angiogenic and lymphangiogenic status of the sample including markers of microvessel density, endothelial stem or progenitor cells, pro-angiogenic/pro-lymphangiogenic factors and receptors for pro-angiogenesis/pro-lymphangiogenesis; markers of the tumor microenvironment including markers of extracellular components and their receptors and extracellular component regulators; and markers of the migration activity of tumor cells including markers of pro-migratory factors, receptors for pro-migratory factors, epithelial to mesenchymal transition and actin cytoskeleton regulators associated with cell migration.

Markers of the Tumor Status

Markers of the tumor status reflect the level of inflammation, cancer stem cells, hypoxia, the level of cell death, the level of posttranslational modifications and the level of proliferation in the sample.

Markers of Inflammation

Inflammation is defined by the presence of inflammatory cells (T or B-cells, mast cells, eosinophils, dendritic cells, macrophages) and inflammatory factors (cytokines, nitric oxide).

The level of inflammation in the sample may be assessed by any marker known by the skilled person, including, but not being limited to, SDF1 pathway members such as SDF1, CXCR4, CRCR7, JAK 2, STAT3 and NFkB; other molecules reflecting the level of inflammation such as VCAM-1, ICAM-1, pSelectin, TNFa, tumor promoting cytokines such as IL-6, IL-23, IL-1, IL-13 and other members of the family, IGF-1, BAFF, CSF-1, MSP, TGFb and Nitric oxide (NO); chemokines such as CCL2/MCP-1, CCL3/MIP-1a, CCL4/MIP-1b, CCL5 or RANTES, CCL8 and MCP-2; markers of immune cell infiltration such as CD163, CD204, CD4, CD8, CD68, CD66b, CD25, OX40 (CD134), Foxp3 and CD20 (Grivennikov et al., Cell. 2010, 140(6): 883-899; Xueqing et al., Cancer Metastasis Rev. 2010 December; 29(4): 709-722; Beverly et al., Clin Cancer Res; 16(11); 2927-31; Shiao et al., Genes and development 2011, 25:2559-2572; Pollard, Nature 2004, 71-78; Raposo, The Veterinary Journal 2015, 1090-0233; Ino et al., Br J Cancer 2013., 914-23; Ladanyi et al., Clinical Cancer Research 2004, 521-530).

In a preferred embodiment, the level of inflammation in the sample is assessed by determining the expression level of SDF1. SDF1 (Stromal-derived factor-1 also known as CXCL12; Gene ID NCBI: 6387) is a homeostatic CXC α-chemokine, a small pro-inflammatory chemoattractant cytokine, expressed in a variety of tissues types, including lymphocytes, hematopoietic stem cells, endothelial cells, epithelial cells, and cancer cells. It facilitates the communication between cancer and normal cells in the tumor microenvironment. It promotes migration, infiltration, activation of neutrophils and tumor-associated macrophages (TAMs) within tumor microenvironment. It also mediates tumor metastasis in several types of cancers.

SDF1 signaling pathway may be therapeutically targeted, for example, with Plerixafor (trade name Mozobil, currently in clinical trial in association with Bevacizumab for recurrent high-grade glioma), a hematopoietic stem cell mobilizer that is used to stimulate the release of stem cells from the bone marrow into the blood in patients with non-Hodgkin lymphoma and that blocks CXCR4, the receptor for SDF1 (Beverly A. T., Simon P. F., Clinical Cancer Research, (2010), 16: 11; Xueqing Sun, Guangcun Cheng, et al., Cancer Metastasis Rev. (2010), 29(4): 709-722).

Markers of Cancer Stem Cells

Cancer stem cells are defined as the subpopulation of tumor cells exhibiting markers or combination of markers shared with stem cells. Cancer stem cells define a subpopulation of cancer cells with many clinical implications in most cancer types including: initiation of micro and macrometastases, causing treatment resistance and recurrence in cancer. These multiple functions reflect the activation of different signaling pathways such as Notch, Wnt/β-catenin, TGF-β, Hedgehog, PI3K/Akt/mTOR and JAK/STAT pathways.

The presence of cancer stem cells can be assessed by any marker known by the skilled person, including, but not being limited to, CD133, Nestin, CD15, CD24, CD31, CD34, CD44, CD45, CD49f (Integrin α6 chain), CD166, CD171, CD184 (CXCR4), CD325 (N-Cadherin), CD326 (EpCAM), CD338 (ABCG2), HER-2/neu, Lgr5, Notch1, Notch2, SSEA-1, BMI-1, B-Catenin, CDX-2, Doublecortin, EZH2, Fibronectin, GFAP, Nucleosemin, Oct3/4, Sox2, Vimentin, ALDH1, Trop2, TGFb, Musashi, NRP1, Wnt/β-catenin pathway, TGF-β pathway, Hedgehog pathway, PI3K/Akt/ mTOR pathway and JAK/STAT pathway (Klonisch et al., Trends Mol Med. 2008, 450-60; Wu et al., Journal of Experimental & Clinical Cancer Research 2015, 34:44; Medema, Nat Cell Biol. 2013 April; 15(4):338-44; Dahlrot R H et al., Dan Med J. 2014, B4944; Zhong Li, Experimental Hematology & Oncology, (201)3, 2:17).

In a preferred embodiment, the cancer stem cells content of the sample is assessed by determining the expression level of CD133. CD133, also known as PROM1 (Gene ID NCBI: 8842), is a progenitor and a cancer stem cell marker. It maintains stem cell properties by suppressing differentiation. Its expression is associated with several types of cancer. It contributes to tumorigenesis, metastasis, recurrence, chemoresistance and poor prognosis. It is also involved in transdifferenciation.

CD133 signaling pathway, i.e. Wnt/0-catenin signaling pathway, may be therapeutically targeted, for example, with XAV939, a Tankyrase inhibitor currently in preclinical trial. XAV939 stimulates beta-catenin degradation by stabilizing axin, the concentration-limiting component of the destruction complex (Zhong Li, Experimental Hematology & Oncology, (201)3, 2:17).

Markers of Hypoxia

Hypoxia (hypoxiation or anoxemia) is a condition in which the body or a region of the body is deprived of adequate oxygen supply. Most tumors develop regions that have insufficient vascular supply, and therefore present severe hypoxia. In many hypoxic, yet viable areas, oxygen partial pressure is almost two orders of magnitude lower that in normal tissues. Hypoxic cells are resistant to radiotherapy or chemotherapy and hence are a source of recurrence of the tumors.

The hypoxic status of a sample can be assessed by any marker known by the skilled person, including, but not being limited to, HIF and its target genes, GLUT-1, CA IX carbonic anhydrase IX, LDH-5 lactate deshydrogenase isoenzyme 5, MCT-1 and MCT-4 (Vaupel et al., Cancer Metastasis Rev 2007, 26:225-239; Rademakers et al., BMC Cancer 2011, 11:167)

In a preferred embodiment, the hypoxic status of the sample is assessed by determining the expression level of HIF1α (Gene ID NCBI: 3091). HIF1A is a member of hypoxia-inducible factors family (HIF family). It functions as a master transcriptional regulator of the adaptive response to hypoxia which is associated with malignant progression, invasion, angiogenesis, changes in metabolism and increased risk of metastasis. It has also a role in cancer resistance to treatment.

HIF1α signaling pathway may be therapeutically targeted, for example, with digoxin, a nonspecific HIF1a inhibitor currently under evaluation in early phase trials in lung and prostate cancer, or bortezomib that represses HIF-1α protein expression, licensed for treatment of multiple myeloma and currently under evaluation in early-phase trials in solid tumors (Favaro et al. Genome Medicine, (2011), 3:55).

Markers of Cell Death

Cell death can occur through different mechanisms, defined by their nature and physiological implications. This includes apoptosis, necrosis and autophagic cell death.

The level of cell death in a sample can be assessed by any marker known by the skilled person, including, but not being limited to, markers of apoptosis such as BCL-2, Bcl-XL, Bcl-w, Mcl-1, A1/Bfl-1, CED-9, cFLIP, PARG, Bax and related anti-apoptotic factors, markers of necrosis such as RIP3 and Caspase 8, markers of autophagy such as PI3K and Beclin1 (Portt et al., Biochimica et Bio-physica Acta 2011 238-259; Cory et al., Oncogene 2003, 22, 8590-8607; Liu et al., Int J Biochem Mol Biol 2012, 165-178; Su et al., Mol Cancer. 2015, 10.1186).

In a preferred embodiment, the level of cell death in the sample is assessed by determining the expression level of BCL-2 and/or PARG, preferably BCL-2 and PARG.

BCL-2 (B cell lymphoma protein 2; Gene ID NCBI: 596), a member of the BCL-2 family, is an anti-apoptotic protein and inhibits certain forms of necrotic cell death. It is overexpressed in a variety of human malignancies. BCL-2 signaling pathway may be therapeutically targeted, for example, with ABT-199, a potent and selective BCL-2 inhibitor currently under evaluation in clinical trials for leukemia and lymphoma (KW Yip and JC Reed, Oncogene (2008) 27, 6398-6406; Souers et al., Nature Medicine, 19, 202-208, 2013).

PARG (Poly ADP-ribose glycohydrolase; Gene ID NCBI: 8505) is a major enzyme responsible for catalyzing the formation and degradation of poly (ADP-ribose) (PAR) polymers, a reversible covalent-modifier of chromosomal proteins. PARG has a role in DNA repair and damage, in chromatin dynamics, transcriptional regulation, and cell death. PARG signaling pathway may be therapeutically targeted, for example, with GPI 16552, currently in preclinical study for melanoma (Rafiqul I., Fumiaki K., 24 (2014) 3802-3806; Lucio T., Carlo L., European Journal of Cancer 41, (2005) 2948-2957).

Markers of Posttranslational Modifications

Many cellular responses (including cell proliferation, migration or response to DNA double-stranded breaks) involve numerous proteins triggering ubiquitination and other ubiquitin-like modifiers such as SUMOylation, phosphorylation, methylation, acetylation or ADP-ribosylation.

The level of posttranslational modifications in a sample can be assessed by any marker known by the skilled person, including, but not being limited to, PARG, PARP 1 and 2, Histone deacetylases (HDACs), Histone acetyltransferases (HATs), Histone methyltransferases, Histone demethylases, DNA methyltransferase (DNMTs), Protein methyltransferases (PMTs), Protein arginine methyltransferases (PRMTs), Protein lysine methyltransferases (PKMTs), Lysines demethylases, Kinases Aurora-B, SUMO family and N/O glycosylation markers such as lectins (Nilufer Jasmine Selimah Fauzee & Juan Pan, Pathol. Oncol. Res. (2010) 16:469-478; Wan Feng, Bin Zhang et al., Cancer Letters 347 (2014) 183-190; Debby M. E. I. Hellebrekers, Arjan W. Griffioen, et al., Biochimica et Biophysica Acta 1775 (2007) 76-91; Roy M. Pollock, Victoria M. Richon, Drug Discovery Today: Therapeutic Strategies, (2009) 6-2; Robert A Copeland, Edward J Olhava, Current Opinion in Chemical Biology, (2010), 14:505-510; Ruth G. F. and Frauke M., Nature Reviews molecular cell biology, (2007), 8; Niall O'D., Biochimica et Biophys-ica (2002) 336-345).

In a preferred embodiment, the level of posttranslational modifications in the sample is assessed by determining the expression level of PARG.

Markers of Proliferation

Cell proliferation and more particularly uncontrolled cell proliferation is a very important component of cancer progression. A myriad of factors, be them cytokines, growth factors, hormones, etc. are known to modulate directly or indirectly the cell cycle.

The level of proliferation in a sample can be assessed by any marker known by the skilled person, including, but not being limited to, PDGFRs/PDGF, EGFR/EGF, HER, C-MET/HGF, IGFR/IGF, FGFRs/FGF, Semaphorins, Neuropilins, Plexins, VEGFRs/VEGF, RAS oncogene and extracellular matrix elements (Masaubmi Shibuya, Angiogenesis (2006) 9:225-230; Masaubmi Shibuya et al. Journal of biochemistry and molecular biology, 5: 469-478; Seker & Harvey, Dev Dyn (2015) 244: 323-331; Alexander K., Satdarshan P. M., Gen Expr (2015), 16(3): 109-127; Juan Carlos Samame Perez-Vargas, et al, Int. J. Mol. Sci. 2013, 14, 18056-18077; Y. Yarden, European Journal of Cancer 37 (2001) S3-S8; Perez E A et al., Cancer Treat Rev (2014) 276-284; Nicholas T., Richard G., nature review cancer, (2010) 10).

In a preferred embodiment, the level of proliferation in the sample is assessed by determining the expression level of EGFR, HER2, PDGFR, Sema3A, NRP1, NRP2, PlexA1, PlexB1, VEGFA, VEGFR1, VEGFR2, MMP9, MMP2, TNC, TNW, IntB1, CMET and/or FGF2, preferably EGFR, AER2, PDGFR, Sema3A, NRP1, NRP2, PrexA1, PexB1, VEGFA, VEGFR1, VEGFR2, MKP9, MMP2, TNC, TNW, IntB1, CMET and FGF2, and more preferably EGFR, HER2, PDGFR, Sema3A, NRP1, NRP2, PlexA1, VEGFA, VEGFR1, VEGFR2, MMIP9, MMIP2, TNC, IntB1, CMET and FGF2.

In a particular embodiment, the markers of the tumor status are selected from the group consisting of genes listed in Table 1.

TABLE 1

List of preferred markers of the tumor status

| Gene | Official Symbol | Official Full Name | Gene ID NCBI |
|---|---|---|---|
| ABL1 | ABL1 | ABL proto-oncogene 1, non-receptor tyrosine kinase | 25 |
| ALK | ALK | anaplastic lymphoma receptor tyrosine kinase | 238 |
| B7-H3 (CD276) | CD276 | CD276 molecule | 80381 |
| BCL2 | BCL2 | BCL2, apoptosis regulator | 596 |
| BRAF | BRAF | B-Raf proto-oncogene, serine/threonine kinase | 673 |
| CD133 (PROM1) | PROM1 | prominin 1 | 8842 |
| CMET | MET | MET proto-oncogene, receptor tyrosine kinase | 4233 |
| CTLA4 | CTLA4 | cytotoxic T-lymphocyte associated protein 4 | 1493 |
| EGFR | EGFR | epidermal growth factor receptor | 1956 |
| FGFR1 | FGFR1 | fibroblast growth factor receptor 1 | 2260 |
| FGFR2 | FGFR2 | fibroblast growth factor receptor 2 | 2263 |
| FGFR3 | FGFR3 | fibroblast growth factor receptor 3 | 2261 |
| HER2 | ERBB2 | erb-b2 receptor tyrosine kinase 2 | 2064 |
| ERBB3 | ERBB3 | erb-b2 receptor tyrosine kinase 3 | 2065 |
| HIF1A | HIF1A | hypoxia inducible factor 1 alpha subunit | 3091 |
| IGF1R | IGF1R | insulin like growth factor 1 receptor [(human)] - NCBI | 3480 |
| IntαV (ITGA5) | ITGA5 | integrin subunit alpha 5 | 3678 |
| JAG1 | JAG1 | jagged 1 | 182 |
| MEK 1 (MAP2K1) | MAP2K1 | mitogen-activated protein kinase kinase 1 | 5604 |
| MEK 2 (MAP2K2) | MAP2K2 | mitogen-activated protein kinase kinase 2 | 5605 |
| MMP9 | MMP9 | matrix metallopeptidase 9 | 4318 |
| PDL1 (CD274) | CD274 | CD274 molecule | 29126 |
| RET | RET | ret proto-oncogene | 5979 |
| CXCL12 (SDF1) | CXCL12 | C-X-C motif chemokine ligand 12 | 6387 |
| VEGFA | VEGFA | vascular endothelial growth factor A | 7422 |
| VEGFR2 (KDR) | KDR | kinase insert domain receptor | 3791 |
| VEGFR3 (FLT4) | FLT4 | fms related tyrosine kinase 4 | 2324 |
| CEACAM-1 | CEACAM1 | carcinoembryonic antigen related cell adhesion molecule 1 | 634 |
| CEACAM-5 | CEACAM5 | carcinoembryonic antigen related cell adhesion molecule 5 | 1048 |
| PI3K alpha (PIK3CA) | PIK3CA | phosphatidylinositol-4,5-bisphosphate 3-kinase catalytic subunit alpha | 5290 |
| AKT1 | AKT1 | AKT serine/threonine kinase 1 | 207 |
| AR (androgen receptor) | AR | androgen receptor | 357 |
| HDAC1 | HDAC1 | histone deacetylase 1 | 3065 |
| HDAC2 | HDAC2 | histone deacetylase 2 | 3066 |
| C-RAF (RAF1) | RAF1 | Raf-1 proto-oncogene, serine/threonine kinase | 5894 |
| PD1 | PDCD1 | programmed cell death 1 | 5133 |
| MDM2 | MDM2 | proto-oncogene | 4193 |
| CDK4 | CDK4 | cyclin dependent kinase 4 | 1019 |
| CDK6 | CDK6 | cyclin dependent kinase 6 | 1021 |
| IDO1 | IDO1 | indoleamine 2,3-dioxygenase 1 | 3620 |
| ABL2 | ABL2 | ABL proto-oncogene 2, non-receptor tyrosine kinase | 27 |
| FGFR4 | FGFR4 | fibroblast growth factor receptor 4 | 2264 |
| HER4 (ERBB4) | ERBB4 | erb-b2 receptor tyrosine kinase 4 | 2066 |
| KIT | KIT | KIT proto-oncogene receptor tyrosine kinase | 3815 |
| EZH2 | EZH2 | EZH2 enhancer of zeste 2 polycomb repressive complex 2 subunit | 2146 |
| IDH1 | IDH1 | isocitrate dehydrogenase (NADP(+)) 1, cytosolic | 3417 |
| IDH2 | IDH2 | isocitrate dehydrogenase (NADP(+)) 2, mitochondrial | 3418 |
| VHL | VHL | von Hippel-Lindau tumor suppressor | 7428 |
| mTOR | MTOR | mechanistic target of rapamycin | 2475 |

TABLE 1-continued

List of preferred markers of the tumor status

| Gene | Official Symbol | Official Full Name | Gene ID NCBI |
|---|---|---|---|
| TRAIL-R1 (TNFRSF10A) | TNFRSF10A | TNF receptor superfamily member 10a | 8797 |
| TRAIL-R2 (TNFRSF10B) | TNFRSF10B | TNF receptor superfamily member 10b | 8795 |
| CD39 (ENTPD1) | ENTPD1 | ectonucleoside triphosphate diphosphohydrolase 1 | 953 |
| CREBBP | CREBBP | CREB binding protein | 1387 |
| EP300 | EP300 | E1A binding protein p300 | 2033 |
| BRD4 | BRD4 | bromodomain containing 4 | 23476 |
| GRB2 | GRB2 | growth factor receptor bound protein 2 | 2885 |
| NOTCH 1 | NOTCH1 | notch 1 | 4851 |
| NOTCH 2 | NOTCH2 | notch 2 | 4853 |
| EPHA1 | EPHA1 | EPH receptor A1 | 2041 |
| ANGPT1 | ANGPT1 | angiopoietin 1 | 284 |
| Tie2 (TEK) | TEK | TEK receptor tyrosine kinase | 7010 |
| RHOA | RHOA | ras homolog family member A | 387 |
| MMP2 | MMP2 | matrix metallopeptidase 2 | 4313 |
| DDR1 | DDR1 | discoidin domain receptor tyrosine kinase 1 | 780 |
| DDR2 | DDR2 | discoidin domain receptor tyrosine kinase 2 | 4921 |
| KDM1A (LSD1) | KDM1A | lysine demethylase 1A | 23028 |
| FOXP3 | FOXP3 | forkhead box P3 | 50943 |
| CD27 | CD27 | CD27 molecule | 939 |
| ICOS (CD278) | ICOS | inducible T-cell costimulator | 29851 |
| IL4 | IL4 | interleukin 4 | 3565 |
| IL13 | IL13 | interleukin 13 | 3596 |
| HMGB1 | HMGB1 | high mobility group box 1 | 3146 |
| FPR1 | FPR1 | formyl peptide receptor 1 | 2357 |
| TGFb 1 | TGFB1 | transforming growth factor beta 1 | 7040 |
| TGFb 2 (LDS4) | TGFB2 | transforming growth factor beta 2 | 7042 |
| CD40 | CD40 | CD40 molecule | 958 |
| IL6 | IL6 | interleukin 6 | 3569 |
| CTNNB1 | CTNNB1 | catenin beta 1 | 1499 |
| MYC | MYC | v-myc avian myelocytomatosis viral oncogene homolog | 4609 |
| WNT 2 | WNT2 | Wnt family member 2 | 7472 |
| WNT 3 | WNT3 | Wnt family member 3 | 7473 |
| CXCR4 | CXCR4 | C-X-C motif chemokine receptor 4 | 7852 |
| CXCL10 | CXCL10 | C-X-C motif chemokine ligand 10 | 3627 |
| TLR4 | TLR4 | toll like receptor 4 | 7099 |
| IL2RB | IL2RB | interleukin 2 receptor subunit beta | 3560 |
| PDL2 (PDCD1LG2) | PDCD1LG2 | programmed cell death 1 ligand 2 | 80380 |
| KIR2DL5A | KIR2DL5A | killer cell immunoglobulin like receptor, two Ig domains and long cytoplasmic tail 5A | 57292 |
| NRP1 | NRP1 | Neuropilin-1 | 8829 |
| NRP2 | NRP2 | Neuropilin-2 | 8828 |
| PARG | PARG | poly(ADP-ribose) glycohydrolase | 8505 |
| VEGFR1 | FLT1 | fms related tyrosine kinase 1 | 2321 |
| FGF2 | FGF2 | fibroblast growth factor 2 | 2247 |
| INTB1 (ITGB1) | ITGB1 | Integrin subunit beta1 | 3688 |

In a more particular embodiment, the markers of the tumor status are selected from the group consisting of ABL1, ALK, B37-H-3 (CD276), BCL2, BRAT, CD133 (PROM1), CMET, CTLA4, EGFR, FGFR1, FGFR2, FGFR3, HER2, ERBB3, HIF1A, IGF1R, IntαV (ITGA5), JAG1, MEK 1 (MAP2K1), MEK 2 (MAP2K2), MMIP9, PDL1 (CD274), RET, CXCL12 (SDF1), VEGFA, VEGFR2 (KDR), VEGFR3 (FLT4), CEACAM-1, CEACAM-5, PI3K alpha (PIK3 CA), AKT 1, AR (androgen receptor), HIDAC1, HIDAC2, C-RAF (RAF1), PD 1, MIDM2, CDK4, CDK6, IDO1, ABL2, FGFR4, HER4 (ERBB34), KIT, EZH2, IDH1, TDH2, VHL, mTOR, TRAIL-R1 (TNFRSF10A), TRAIL-R2 (TNFRSF10B), CD39 (ENTPD1), CREBBP, EP300, BRD4, GRB2, NOTCH 1, NOTCH 2, EPHA1, ANGPT1, Tie2 (TEK), RHOA, MMP2, DDR1, DDR2, KDM1A (LSD1), FOXP3, CD27, ICOS (CD278), IL4, IL13, HMNGB1, FPR1, TGFb 1, TGFb 2 (LDS4), CD40, IL6, CTNNB1, MYC, WNT 2, WNT 3, CXCR4, CXCL10, TLR4, IL2RB, PDL2 (PDCD1LG2) and KIR2DL5A.

In a preferred embodiment, the markers of the tumor status are selected from the group consisting of BCL2, CD133 (PROM1), CMET, EGFR, HER2, HIF1A, JAG1, MMP9, CXCL12 (SDF1), VEGFA, VEGFR2 (KDR) and MMP2.

Markers of the Angiogenic and Lymphangiogenic Status

The angiogenic and lymphangiogenic status refers to blood or lymphatic vessels content in the sample, those vessels being generated from tumor surrounding pre-existing blood or lymphatic vessels. Markers of the angiogenic and lymphangiogenic status reflect the microvessel density, the level of endothelial stem or progenitor cells, the level of pro-angiogenic/pro-lymphangiogenic factors and the level of expression of receptors for pro-angiogenesis/pro-lymphangiogenesis.

Markers of the Microvessel Density

Microvessel density refers to the nascent vascular bed associated with the angiogenic switch known as the key step towards the increased of tumor blood supply required for further tumor development.

Microvessel density can be assessed by any marker known by the skilled person, including, but not being limited to, CD34, LYVE1, NG2, VE cadherin, Integrin isoforms such as ITGB1 and CD31 (Sidney et al., stem cells 2014, 10.1002; Armulik et al., Circulation Research 2005, 10.1161).

In a preferred embodiment, the microvessel density in the sample is assessed by determining the expression level of CD34 and/or ITGB1, preferably CD34 and ITGB1.

CD34 (Gene ID NCBI: 947) is a transmembrane glycoprotein marker of hematopoietic stem cells and progenitor cells and also a marker of non-hematopoietic cell types as vascular endothelial progenitors.

ITGB1 (or INTB1, Gene ID NCBI: 3688), i.e. integrin beta 1, is the beta sub-unit of the integrin receptor, a matrisome member. It is fundamental in cell motility, migration, angiogenesis, differentiation and metastatic diffusion of tumor cells. It is involved in the turnover of cell adhesion in a dynamic way. It is also an actor of EMT (epithelial-mesenchymal transition) and a regulator of actin cytoskeleton. ITGB1 signaling pathway may be therapeutically targeted, for example, with cilengitide currently in clinical study for many cancers (Timothy M E, S., Maddy P., Current Opinion in Cell Biology (2011), 23:562-568).

Markers of Endothelial Stem or Progenitor Cells

Endothelial stem or progenitor cells include hematopoietic and non-hematopoietic stem cells being capable of producing new blood vessels.

The level of endothelial stem or progenitor cells can be assessed by any marker known by the skilled person, including, but not being limited to, CD34, CD144, VEGFR2 or KDR, CD45, CD133, CD146 and NRP1 (Urbich et al., Circulation Research 2004, 10.1161; Yoder, Cold Spring Harb Perspect Med. 2012, 10.1101).

In a preferred embodiment, the level of endothelial stem or progenitor cells in the sample is assessed by determining the expression level of CD34, NRP1 and/or CD133, preferably CD34, NRP1 and CD133.

NRP1 (Neuropilin-1, Gene ID NCBI: 8829) binds many ligands such as class 3 Semaphorins and vascular endothelial growth factor, and has various types of co-receptors. It affects cell survival, migration, and attraction. It plays a role during nervous system development, angiogenesis, tumorigenesis. It is also a part of the matrisome.

NRP1 signaling pathway may be therapeutically targeted, for example, with an antibody anti-NRP1 or MTP-NRP1, a peptide targeting neuropilin-1 (Nasarre C, et al., (2010) Oncogene 29: 2381-2392; Lee M. Ellis, Mol Cancer Ther, (2006) 5(5)).

Markers of Pro-Angiogenic Pro-Lymphangiogenic Factors

A huge diversity of secreted or membrane bound factors have been shown to promote endothelial cells proliferation, migration or differentiation during the process of blood vessel construction.

The level of pro-angiogenic/pro-lymphangiogenic factors can be assessed by any marker known by the skilled person, including, but not being limited to, VEGF isoforms, PLGF, Angiopoetins, JAG1,2, NICD, DLLs, Ephrins, Wnt family, Semaphorins, Interleukins, FGFs, and Extracellular Matrix molecules such as Tenascins, MMPs and others (Shibuya, Journal of Biochemistry and Molecular Biology 2006, 469-478; Zheng, The Journal of Clinical Investigation 2014, 10.1172; Carmeliet et al., Nature 2011, 10.1038; Duong et al., Journal of oncology 2012, 10.1155; Weis et al., Nature 2011, 10.1038; Yancopoulos et al., Nature 2000, 14; 407; Secker et al., Dev Dyn. 2015, 10.1002; Andersson et al., Nature 2014, 10.1038).

In a preferred embodiment, the level of pro-angiogenic/pro-lymphangiogenic factors in the sample is assessed by determining the expression level of VEGFA, JAG, Sema3A FGF2, TNC, TNW, MMP-2 and/or MMP-9, preferably VEGFA, JAG, Sema3A FGF2, TNC, TNW, MMP-2 and MMP-9.

VEGFA (Vascular Endothelial Growth Factor A; Gene ID NCBI: 7422) is a key angiogenesis activator. It increases vascular permeability, vasculogenesis, lymphoangiogenesis, and growth of endothelial cell derived from arteries, veins and lymphatics. It is aberrantly overexpressed in many types of cancer. VEGFA signaling pathway may be therapeutically targeted, for example, with bevacizumab currently used as second line treatment of glioblastoma (Napoleone F., Hns-Peter G., et al., (2003) 9-6).

JAG1 (Jagged1; Gene ID NCBI: 182) is Notch receptor ligand promoting angiogenesis. It activates endothelial cells proliferation and sprouting. It is a key factor in vascular smooth muscle cell coverage of new vessels and also in CD34-mediated interaction of endothelial and perivascular cells. It is also a part of the matrisome. It is involved in many cancer types. JAG1 signaling pathway may be therapeutically targeted, for example, with RO4929097 currently in phase I for malignant glioma and phase II for metastatic colorectal Cancer (Demin Li, Massimo Masiero, et al., (2004) 4 254; Emma R. Andersson, Urban Lendahl, drug discovery, (2014), 13).

MMP2 (matrix metalloproteinase 2; Gene ID NCBI: 4313) plays a role in the regulation of both cell-cell and cell-extracellular matrix interactions. It controls angiogenesis, cell differentiation, proliferation, migration and apoptosis. It is involved in multiple pathways including roles in nervous system, regulation of vascularization, and metastasis. It is an actor of EMT (epithelial-mesenchymal transition) thanks to its capacity to degrade extracellular matrix components leading to cell migration in many tissues. MMP2 signaling pathway may be therapeutically targeted, for example, with Incyclidine or Marimastat, currently in phase III for lung cancer and other (Jialiang Hu, et al., Nature Reviews Drug Discovery 2007 June; 6, 480-498; Gillian Murphy, Mol Aspects Med. 2008 October; 29(5): 290-308).

MMP9 (matrix metalloproteinase 9; Gene ID NCBI: 4318) plays a role in the regulation of both cell-cell and cell-extracellular matrix interactions. It controls angiogenesis, cell differentiation, proliferation, migration, apoptosis and cellular differentiation. It is also involved in embryonic development, reproduction, tissue remodeling, and metastasis. It is an actor of EMT (epithelial-mesenchymal transition) thanks its capacity to degrade extracellular matrix components leading to cell migration in other tissues. MMP9 signaling pathway may be therapeutically targeted, for example, with Marimastat and PCK 3145 currently in phase I for prostate cancer (Jialiang Hu, et al., Nature Reviews Drug Discovery 2007 June; 6, 480-498; Gillian Murphy, Mol Aspects Med. 2008 October; 29(5): 290-308).

SEMA3A (Class 3 semaphorins, Gene ID NCBI: 10371) is a member of Semaphorin family. It is involved nervous system development, axon attraction and repulsion, cell migration, cytoskeleton dynamics, immune response, apoptosis, organogenesis, tumor suppression and promotion, and vasculature development. It is also a member of the matrisome.

TNW (also known as TNN or tenascin N, Gene ID NCBJ: 63923 is implicated in many cellular mechanisms such as cell adhesion, motility, proliferation, migration, differentiation and angiogenesis. Is not expressed in a majority of adult organs, but is overexpressed in solid tumors.

TNC (Tenascin-C; Gene ID NCBI: 3371) is an extracellular matrix glycoprotein involved in cell adhesion, in tissue architecture, in regulation of cell proliferation, angiogenesis and migration, especially during developmental differentiation and wound healing. It is implicated in guidance of migrating neurons as well as axons during development, synaptic plasticity, and neuronal regeneration. TNC promotes tumor progression, dissemination and metastasis. TNC signaling pathway may be therapeutically targeted, for example, with Neuradiab (Bradmer Pharmaceuticals, Inc.).

FGF2 (Gene ID NCBI: 2247) is a ligand of fibroblast growth factor (FGFR) family. It plays a role in tumorigenesis by its implication in cell division, survival, and migration, in angiogenesis. It is also a member of the matrisome. FGF2 signaling pathway may be therapeutically targeted, for example, with Vargatef or AZD4547 currently in phase II for lung cancer (Nicholas T., Richard G., nature review cancer, (2010) 10).

Markers of Pro-Angiogenic Receptors

The level of pro-angiogenic receptors can be assessed by any marker known by the skilled person, including, but not being limited to, NOTCH1, 2, 3, 4, VEGFRs, TIEs, PDGFRs, EGFRs, Neuropilins, JAK, FGFRs, WNTs, EPHRs, Plexins, Alk Receptors, CXCR4/12, HER2 and Integrins (Shibuya, Journal of Biochemistry and Molecular Biology 2006, 469-478; Zheng, The Journal of Clinical Investigation 2014, 10.1172; Carmeliet et al., Nature 2011, 10.1038; Duong et al., Journal of oncology 2012, 10.1155; Weis et al., Nature 2011, 10.1038; Yancopoulos et al., Nature 2000, 14; 407; Secker et al., Dev Dyn. 2015, 10.1002; Andersson et al., Nature 2014, 10.1038).

In a preferred embodiment, the level of pro-angiogenic receptors in the sample is assessed by determining the expression level of VEGFR1, VEGFR2, HER2, EGFR, NRP1, NRP2, PlexA1, PlexB1 and/or INTB1, preferably VEGFR1, VEGFR2, HER2, EGFR, NRP1, NRP2, PlexA1, PlexB1 and INTB1.

VEGFR1 (Flt1) plays an important role in angiogenesis and vasculogenesis. It promotes endothelial cell proliferation, migration and survival. VEGFR1 signaling pathway may be therapeutically targeted, for example, with Vandatenib, Pasopanib, Sunitinib or Axitinib currently in clinical trial for glioblastoma (Masaubmi Shibuya, Angiogenesis (2006) 9:225-230).

VEGFR2 (KDR/Flk1) is the main mediator of VEGF-induced endothelial proliferation, survival, migration, tubular morphogenesis and sprouting. It is also important in the lymphatic vasculature. VEGFR2 signaling pathway may be therapeutically targeted, for example, with Ponatinib or Cediranib in clinical trial for glioblastoma and metastatic colorectal cancer and other (Masabumi Shibuya, Angiogenesis, (2006), 5: 469-478; Seker & Harvey, Dev Dyn (2015) 244: 323-331).

HER2 (Epidermal growth factor receptor 2) plays an important role in the development and progression of certain aggressive types of breast cancer and other cancers. It is involved in cell survival, migration, and angiogenesis. HER2 signaling pathway may be therapeutically targeted, for example, with Lapatinib, Afatinib or Trastuzumab (HERCEPTIN®) used in breast cancer treatment (Perez E A et al., Cancer Treat Rev (2014) 276-284).

EGFR (Epidermal Growth Factor Receptor) represents an important target for cancer treatment. It leads to tumor growth, progression, including proliferation, migration, angiogenesis, invasion, and metastasis. It is associated with a large number of cancers. It is an actor of EMT (epithelial-mesenchymal transition). EGFR signaling pathway may be therapeutically targeted, for example, with Lapatinib, Afatinib or cetuximab (ERBITUX®) currently used as first line treatment in colorectal cancer (Yarden, European Journal of Cancer 37 (2001) S3-S8).

PLEXA1 (PlexinA1) is a partner of NRP and interacts with Rho-GTPase proteins. It triggers growth cone collapse in neurons, and also migration and angiogenesis. It is a part of the matrisome. PLEXA1 signaling pathway may be therapeutically targeted, for example, with MTP-PlexA1 currently in pre-clinical study.

PLEXB1 (PlexinB1) interacts with Rho-GTPase proteins, it plays a role in axon guidance, invasive growth, cell migration and angiogenesis. It is a part of the matrisome.

NRP2 (Neuropilin-2) is a co-receptor for class 3 Semaphorins and vascular endothelial growth factor. It plays a role in neuronal guidance. It is implicated in tumorigenesis and metastasis. NRP2 signaling pathway may be therapeutically targeted, for example, with MTP-NRP2 currently in pre-clinical study (Parker and Vander Kooin, Anal Biochem. 2014 May 15; 453:4-6).

In a particular embodiment, the markers of the angiogenic and lymphangiogenic status are selected from the group consisting of genes listed in Table 2.

TABLE 2

List of preferred markers of the angiogenic and lymphangiogenic status

| Gene | Official Symbol | Official Full Name | Gene ID NCBI |
|---|---|---|---|
| BRAF | BRAF | B-Raf proto-oncogene, serine/threonine kinase | 673 |
| EGFR | EGFR | epidermal growth factor receptor | 1956 |
| FGFR1 | FGFR1 | fibroblast growth factor receptor 1 | 2260 |
| FGFR2 | FGFR2 | fibroblast growth factor receptor 2 | 2263 |
| FGFR3 | FGFR3 | fibroblast growth factor receptor 3 | 2261 |
| HER2 | ERBB2 | erb-b2 receptor tyrosine kinase 2 | 2064 |
| ERBB3 | ERBB3 | erb-b2 receptor tyrosine kinase 3 | 2065 |
| IGF1R | IGF1R | insulin like growth factor 1 receptor [(human)] - NCBI | 3480 |
| IntαV (ITGA5) | ITGA5 | integrin subunit alpha 5 | 3678 |
| JAG1 | JAG1 | jagged 1 | 182 |
| MEK 1 (MAP2K1) | MAP2K1 | mitogen-activated protein kinase kinase 1 | 5604 |
| MEK 2 (MAP2K2) | MAP2K2 | mitogen-activated protein kinase kinase 2 | 5605 |
| MMP9 | MMP9 | matrix metallopeptidase 9 | 4318 |

TABLE 2-continued

List of preferred markers of the angiogenic and lymphangiogenic status

| Gene | Official Symbol | Official Full Name | Gene ID NCBI |
|---|---|---|---|
| PDGFRA | PDGFRA | platelet derived growth factor receptor alpha | 5156 |
| PDGFRB | PDGFRB | platelet derived growth factor receptor beta | 5159 |
| CXCL12 (SDF1) | CXCL12 | C-X-C motif chemokine ligand 12 | 6387 |
| VEGFA | VEGFA | vascular endothelial growth factor A | 7422 |
| VEGFR2 (KDR) | KDR | kinase insert domain receptor | 3791 |
| VEGFR3 (FLT4) | FLT4 | fms related tyrosine kinase 4 | 2324 |
| CEACAM-1 | CEACAM1 | carcinoembryonic antigen related cell adhesion molecule 1 | 634 |
| CEACAM-5 | CEACAM5 | carcinoembryonic antigen related cell adhesion molecule 5 | 1048 |
| PI3K alpha (PIK3CA) | PIK3CA | phosphatidylinositol-4,5-bisphosphate 3-kinase catalytic subunit alpha | 5290 |
| AKT1 | AKT1 | AKT serine/threonine kinase 1 | 207 |
| C-RAF (RAF1) | RAF1 | Raf-1 proto-oncogene, serine/threonine kinase | 5894 |
| FGFR4 | FGFR4 | fibroblast growth factor receptor 4 | 2264 |
| HER4 (ERBB4) | ERBB4 | erb-b2 receptor tyrosine kinase 4 | 2066 |
| mTOR | MTOR | mechanistic target of rapamycin | 2475 |
| NOTCH 1 | NOTCH1 | notch 1 | 4851 |
| NOTCH 2 | NOTCH2 | notch 2 | 4853 |
| EPHA1 | EPHA1 | EPH receptor A1 | 2041 |
| ANGPT1 | ANGPT1 | angiopoietin 1 | 284 |
| Tie2 (TEK) | TEK | TEK receptor tyrosine kinase | 7010 |
| MMP2 | MMP2 | matrix metallopeptidase 2 | 4313 |
| CD34 | CD34 | CD34 molecule | 947 |
| CXCR4 | CXCR4 | C-X-C motif chemokine receptor 4 | 7852 |
| TNC | TNC | tenascin C | 3371 |
| NRP1 | NRP1 | neuropilin-1 | 8829 |
| NRP2 | NRP2 | neuropilin-2 | 8828 |
| PLXNA1 | PLXNA1 | plexin A1 | 5361 |
| PLXNB1 | PLXNB1 | plexin B1 | 5364 |
| FGF2 | FGF2 | fibroblast growth factor 2 | 2247 |
| VEGFR1 | FLT1 | fms related tyrosine kinase 1 | 2321 |
| TNW (TNN) | TNN | Tenascin W | 63923 |
| INTB1 (ITGB1) | ITGB1 | Integrin subunit beta1 | 3688 |

In a more particular embodiment, the markers of the angiogenic and lymphangiogenic status are selected from the group consisting of BRAF, EGFR, FGFR1, FGFR2, FGFR3, HER2, ERBB3, IGF1R, IntαV (ITGA5), JAG1, MEK 1 (MAP2K1), MEK 2 (MAP2K2), MMP9, PDGFRA, PDGFRB, CXCL12 (SDF1), VEGFA, VEGFR2 (KDR), VEGFR3 (FLT4), CEACAM-1, CEACAM-5, PI3K alpha (PIK3CA), AKT1, C-RAF (RAF1), FGFR4, HER4 (ERBB4), mTOR, NOTCH 1, NOTCH 2, EPHA1, ANGPT1, Tie2 (TEK), MMP2, CD34, CXCR4, preferably selected from the group consisting of EGFR, HER2, JAG1, MMP9, PDGFRA, CXCL12 (SDF1), VEGFA, VEGFR2 (KDR) and MMP2.

In a preferred embodiment, the markers of the angiogenic and lymphangiogenic status are selected from the group consisting of EGFR, HER2, JAG1, MMP9, PDGFRA, CXCL12 (SDF1), VEGFA, VEGFR2 (KDR) and MMP2.

Markers of Tumor Microenvironment

Tumor microenvironment is defined as the cellular and molecular context in which the tumor is developing. Generally speaking, any molecule/factor secreted by tumor cells and or surrounding stromal cells is part of the tumor microenvironment. This microenvironment is both a cause and consequence of tumorigenesis. Markers of tumor microenvironment reflect the level of extracellular components and their receptors and the level of extracellular component regulators.

Markers of Extracellular Components and their Receptors

Preferably, extracellular components and their receptors known to be abnormally expressed in the tumor type are studied. Markers are preferably chosen in the list of extracellular matrix (ECM) components defined as the "matrisome" which comprises about 300 proteins.

The level of extracellular components and their receptors can be assessed by any marker known by the skilled person, including, but not being limited to, Collagen isoforms; Extracellular Matrix Glycoproteins such as Laminins, Fibronectins, Tenascins; Proteoglycans such as Perlecan, Decorin, Syndecans; and Integrins (Langlois et al., Oncotarget 2014, 10529-10545; Hynes et al., Cold Spring Harb Perspect Biol 2012, 10.1101; Lu et al., J. Cell Biol. 2012, 10.1083).

In a preferred embodiment, the level of extracellular components and their receptors in the sample is assessed by determining the expression level of TNC, TNW and/or IntB1, preferably TNC, TNW and IntB1.

Markers of Extracellular Component Regulators

Extracellular component regulators refer to a vast ensemble of proteins known to be ECM-modifying enzymes, ECM-binding growth factors, and other ECM-associated proteins.

The level of extracellular component regulators can be assessed by any marker known by the skilled person, including, but not being limited to, ECM-modifying enzymes such as Metalloproteinases such as MMP2 and MMP9; ECM-binding growth factors such as VEGF isoforms, PLGF, Angiopoetins, FGFs and TGF; Other ECM-associated Proteins such as JAG1,2, DLLs, Ephrins, Wnt family, Semaphorins, Interleukins, Netrins and Slit (Egeblad et al., Nature 2002, 10.1038).

In a preferred embodiment, the level of extracellular component regulators in the sample is assessed by determining the expression level of MMP2, MMP9, FGF2, Sema3A, VEGFA and/or JAG, preferably MMP2, MMP9, FGF2, Sema3A, VEGFA and JAG.

In a particular embodiment, the markers of the tumor microenvironment are selected from the group consisting of genes listed in Table 3.

TABLE 3

List of preferred markers of the tumor microenvironment

| Gene | Official Symbol | Official Full Name | Gene ID NCBI |
|---|---|---|---|
| ABL1 | ABL1 | ABL proto-oncogene 1, non-receptor tyrosine kinase | 25 |
| ALK | ALK | anaplastic lymphoma receptor tyrosine kinase | 238 |
| CMET | MET | MET proto-oncogene, receptor tyrosine kinase | 4233 |
| IntαV (ITGA5) | ITGA5 | integrin subunit alpha 5 | 3678 |
| MEK 1 (MAP2K1) | MAP2K1 | mitogen-activated protein kinase kinase 1 | 5604 |
| MEK 2 (MAP2K2) | MAP2K2 | mitogen-activated protein kinase kinase 2 | 5605 |
| MMP9 | MMP9 | matrix metallopeptidase 9 | 4318 |
| RET | RET | ret proto-oncogene | 5979 |
| VEGFA | VEGFA | vascular endothelial growth factor A | 7422 |
| VEGFR2 (KDR) | KDR | kinase insert domain receptor | 3791 |
| VEGFR3 (FLT4) | FLT4 | fms related tyrosine kinase 4 | 2324 |
| CEACAM-1 | CEACAM1 | carcinoembryonic antigen related cell adhesion molecule 1 | 634 |
| CEACAM-5 | CEACAM5 | carcinoembryonic antigen related cell adhesion molecule 5 | 1048 |
| ABL2 | ABL2 | ABL proto-oncogene 2, non-receptor tyrosine kinase | 27 |
| HER4 (ERBB4) | ERBB4 | erb-b2 receptor tyrosine kinase 4 | 2066 |
| mTOR | MTOR | mechanistic target of rapamycin | 2475 |
| NOTCH 1 | NOTCH1 | notch 1 | 4851 |
| NOTCH 2 | NOTCH2 | notch 2 | 4853 |
| EPHA1 | EPHA1 | EPH receptor A1 | 2041 |
| ANGPT1 | ANGPT1 | angiopoietin 1 | 284 |
| Tie2 (TEK) | TEK | TEK receptor tyrosine kinase | 7010 |
| RHOA | RHOA | ras homolog family member A | 387 |
| ROCK 1 | ROCK1 | Rho associated coiled-coil containing protein kinase 1 | 6093 |
| ROCK 2 | ROCK2 | Rho associated coiled-coil containing protein kinase 2 | 9475 |
| MMP2 | MMP2 | matrix metallopeptidase 2 | 4313 |
| DDR1 | DDR1 | discoidin domain receptor tyrosine kinase 1 | 780 |
| DDR2 | DDR2 | discoidin domain receptor tyrosine kinase 2 | 4921 |
| VEGFR1 | FLT1 | fms related tyrosine kinase 1 | 2321 |
| FGF2 | FGF2 | fibroblast growth factor 2 | 2247 |
| TNC | TNC | tenascin C | 3371 |
| TNW (TNN) | TNN | Tenascin W | 63923 |
| SEMA3A | SEMA3A | semaphorin 3A | 10371 |
| INTB1 (ITGB1) | ITGB1 | Integrin subunit beta1 | 3688 |

In a more particular embodiment, the markers of the tumor microenvironment are selected from the group consisting of ABL1, ALK, CMET, IntαV (ITGA5), MILK 1 (MAP2K1), MEK 2 (MAP2K2), MMIP9, RET, VEGFA, VEGFR2 (KDR), VEGFR3 (FLT4), CEACAM-1, CEACAM-5, ABL2, HER4 (ERBB34), mTOR, NOTCH 1, NOTCH 2, EPHA1, ANGPT1, Tie2 (TEK), RHOA, ROCK 1, ROCK 2, MMP2, DDR1 and DDR2.

In a preferred embodiment, the markers of the tumor microenvironment are selected from the group consisting of CMET, MMP9, VEGFA, VEGFR2 (KDR) and MMIP2.

Markers of the Migration Activity

Tumor cell migration is a crucial step of tumor growth involving colonization of peritumoral stroma. This also includes the process of epithelial to mesenchymal transition and the production of metastases, i.e. tumor cells disseminating in the body and eventually giving rise to one or more tumor bulk in various organs. Markers of the migration activity reflect the level of pro-migratory factors, the level of receptors for pro-migratory factors, the level of indicators of epithelial to mesenchymal transition and the level of actin cytoskeleton regulators associated with cell migration.

Markers of Pro-Migratory Factors

Pro-migratory factors include a large number of soluble or membrane interacting factors that have been shown to modulate cell migration.

The level of pro-migratory factors can be assessed by any marker known by the skilled person, including, but not being limited to, ECM factors & regulators such as Fibronectins, Laminins, MMPs, Tenascins; Guidance molecules such as Netrin, Ephrin, Semaphorins, Slit; Growth factors such as TGFalpha, GDNF, IGF, FGF, VEGF isoforms; Chimiokines such as SDF1; and Shh (Dützmann et al., Cell adhesion and migration 2010, 10.4161; Frield et al., Nature 2013, 10.1038; Gaillard et al., Rev Neurol 2005, 153-72; Nasarre C, et al., (2010) Oncogene 29: 2381-2392; Nasarre C, et al, Cell Adh Migr 2009, 3: 383-389; Heath G. P., Yuxiao W., et al., Progress in Biophysics and Molecular Biology (2015) 1-8).

In a preferred embodiment, the level of pro-migratory factors in the sample is assessed by determining the expression level of SDF1, VEGFA, MMP2, MMP9, TNC, TNW, FGF2 and/or Sema3A, preferably SDF1, VEGFA, MMP2, MMP9, TNC, TNW, FGF2 and Sema3A.

Markers of Receptors for Pro-Migratory Factors

Consistently with the diversity of pro-migratory factors, many receptors are involved for binding and signaling of pro-migratory factors.

The level of receptors for pro-migratory factors can be assessed by any marker known by the skilled person, including, but not being limited to, Plexins, Neuropilins, EGRFs, FGFRs, VEGFRs, PDGFRs, HER2, DCC/UNC5, Integrins, Cadherins, EPH Receptors, C-MET and CXCR4 (Dützmann et al., Cell adhesion and migration 2010, 10.4161; Frield et al., Nature 2013, 10.1038; Gaillard et al., Rev Neurol 2005, 153-72; Nasarre C, et al., (2010) Oncogene 29: 2381-2392; Nasarre C, et al, Cell Adh Migr 2009, 3: 383-389; Heath G. P., Yuxiao W., et al., Progress in Biophysics and Molecular Biology (2015) 1-8).

In a preferred embodiment, the level of receptors for pro-migratory factors in the sample is assessed by determining the expression level of VEGFR1, VEGFR2, INTB1, CMET, PDGFRA, HER2, EGFR, NRP1, NRP2, PlexA1 and/or PlexB1, preferably VEGFR1, VEGFR2, INTB1, CMET, PDGFRA, HER2, EGFR, NRP1, NRP2, PlexA1 and PlexB1.

PDGFRα (Platelet derived growth factor alpha, also known as PDGFR2, Gene ID NCBI: 5156) is an isoform of the PDGFR family. It is involved in cell proliferation, survival, migration, differentiation, growth and tumor progression. It plays also a role in EMT (epithelial-mesenchymal transition). It is implicated in several cancers. PDGFRα signaling pathway may be therapeutically targeted, for example, with Axitinib or Imatinib (GLIVEC®) currently used in chronic myeloid leukaemia and gastrointestinal stromal tumour (Kikuchi & Monga, Gene Expression (2015), 16(3): 109-127).

cMET (also known as MET, Gene ID NCBI: 4233) plays a crucial role in several biological activities such as motility, proliferation, migration, cell survival, angiogenesis, and. It is an actor of EMT (epithelial-mesenchymal transition). It is involved in development and metastatic progression of many different tumor types. cMET signaling pathway may be therapeutically targeted, for example, with SU11274 or Crizotinib (XALKORI®) currently used as treatment in non-small cell lung cancer (Juan Carlos Samame Perez-Vargas, et al, Int. J. Mol. Sci. 2013, 14, 18056-18077).

Markers of EMT

As above mentioned, EMT is a process by which epithelial cells lose their cell polarity and cell-cell adhesion, and gain migratory and invasive properties. The level of EMT indicators can be assessed by any marker known by the skilled person, including, but not being limited to, Smooth Muscle Actin SMA, Vimentin, Desmin, IGFRs/IGF, C-MET/HGF, EGFRs/EGF, PDGFRs/PDGF, TGFb, Integrins, Alk-5, b-Catenin, Slug, Cadherin, Wnt, Notch, Matrix degrading enzymes such as MMP2 and MMP9, and Claudins (Kalluri et al., J. Clin. Invest. 2000, 10.1172, Heerboth et al., Clinical and Translational Medicine 2015, 10.1186, Li et al., Pharmacology & Therapeutics 2015, 33-46; Samatov et al., Molecular Cancer 2013, 12:107; Margadant et al., Current Opinion in Cell Biology 2011, 10.1016).

In a preferred embodiment, the level of EMT indicators in the sample is assessed by determining the expression level of INTB1, MMP2 and/or MMP9, preferably INTB1, MMP2 and MMP9.

Markers of Actin Cytoskeleton Regulators

The process of cell migration involves continuous remodelling of cell actin cytoskeleton. This process results from the complex roles of different families of actin-regulator proteins or protein binding to actin-regulator proteins. The level of actin cytoskeleton regulators can be assessed by any marker known by the skilled person, including, but not being limited to, α-actinin, Plexins, RHO-GTPase, RAC, CDC42, myosin light chain, integrins and tropo-myosins (Shankar et al., Cancer Cells, PLOS ONE 2015, 10.1371; Rottner et al., Current Opinion in Cell Biology 2011, 10.1016).

In a preferred embodiment, the level of actin cytoskeleton regulators in the sample is assessed by determining the expression level of PLEXA1, PLEXB1 and/or INTB1, preferably PLEXA1, PLEXB1 and INTB1.

In a particular embodiment, the markers of the migration activity are selected from the group consisting of genes listed in Table 4.

TABLE 4

List of preferred markers of the migration activity

| Gene | Official Symbol | Official Full Name | Gene ID NCBI |
|---|---|---|---|
| ABL1 | ABL1 | ABL proto-oncogene 1, non-receptor tyrosine kinase | 25 |
| ALK | ALK | anaplastic lymphoma receptor tyrosine kinase | 238 |
| BRAF | BRAF | B-Raf proto-oncogene, serine/threonine kinase | 673 |
| CMET | MET | MET proto-oncogene, receptor tyrosine kinase | 4233 |
| EGFR | EGFR | epidermal growth factor receptor | 1956 |
| FGFR1 | FGFR1 | fibroblast growth factor receptor 1 | 2260 |
| FGFR2 | FGFR2 | fibroblast growth factor receptor 2 | 2263 |
| FGFR3 | FGFR3 | fibroblast growth factor receptor 3 | 2261 |
| IGF1R | IGF1R | insulin like growth factor 1 receptor [(human)] - NCBI | 3480 |
| IntαV (ITGA5) | ITGA5 | integrin subunit alpha 5 | 3678 |
| JAG1 | JAG1 | jagged 1 | 182 |
| MEK 1 (MAP2K1) | MAP2K1 | mitogen-activated protein kinase kinase 1 | 5604 |
| MEK 2 (MAP2K2) | MAP2K2 | mitogen-activated protein kinase kinase 2 | 5605 |
| MMP9 | MMP9 | matrix metallopeptidase 9 | 4318 |
| PDGFRA | PDGFRA | platelet derived growth factor receptor alpha | 5156 |
| PDGFRB | PDGFRB | platelet derived growth factor receptor beta | 5159 |
| RET | RET | ret proto-oncogene | 5979 |
| CXCL12 (SDF1) | CXCL12 | C-X-C motif chemokine ligand 12 | 6387 |

TABLE 4-continued

List of preferred markers of the migration activity

| Gene | Official Symbol | Official Full Name | Gene ID NCBI |
|---|---|---|---|
| VEGFA | VEGFA | vascular endothelial growth factor A | 7422 |
| VEGFR2 (KDR) | KDR | kinase insert domain receptor | 3791 |
| VEGFR3 (FLT4) | FLT4 | fms related tyrosine kinase 4 | 2324 |
| CEACAM-1 | CEACAM1 | carcinoembryonic antigen related cell adhesion molecule 1 | 634 |
| CEACAM-5 | CEACAM5 | carcinoembryonic antigen related cell adhesion molecule 5 | 1048 |
| PI3K alpha (PIK3CA) | PIK3CA | phosphatidylinositol-4,5-bisphosphate 3-kinase catalytic subunit alpha | 5290 |
| AKT1 | AKT1 | AKT serine/threonine kinase 1 | 207 |
| C-RAF (RAF1) | RAF1 | Raf-1 proto-oncogene, serine/threonine kinase | 5894 |
| ABL2 | ABL2 | ABL proto-oncogene 2, non-receptor tyrosine kinase | 27 |
| FGFR4 | FGFR4 | fibroblast growth factor receptor 4 | 2264 |
| HER4 (ERBB4) | ERBB4 | erb-b2 receptor tyrosine kinase 4 | 2066 |
| KIT | KIT | KIT proto-oncogene receptor tyrosine kinase | 3815 |
| mTOR | MTOR | mechanistic target of rapamycin | 2475 |
| NOTCH 1 | NOTCH1 | notch 1 | 4851 |
| NOTCH 2 | NOTCH2 | notch 2 | 4853 |
| EPHA1 | EPHA1 | EPH receptor A1 | 2041 |
| ANGPT1 | ANGPT1 | angiopoietin 1 | 284 |
| Tie2 (TEK) | TEK | TEK receptor tyrosine kinase | 7010 |
| RHOA | RHOA | ras homolog family member A | 387 |
| ROCK 1 | ROCK1 | Rho associated coiled-coil containing protein kinase 1 | 6093 |
| ROCK 2 | ROCK2 | Rho associated coiled-coil containing protein kinase 2 | 9475 |
| MMP2 | MMP2 | matrix metallopeptidase 2 | 4313 |
| DDR1 | DDR1 | discoidin domain receptor tyrosine kinase 1 | 780 |
| DDR2 | DDR2 | discoidin domain receptor tyrosine kinase 2 | 4921 |
| HMGB1 | HMGB1 | high mobility group box 1 | 3146 |
| TGFb 1 | TGFB1 | transforming growth factor beta 1 | 7040 |
| TGFb 2 (LDS4) | TGFB2 | transforming growth factor beta 2 | 7042 |
| MYC | MYC | v-myc avian myelocytomatosis viral oncogene homolog | 4609 |
| WNT 2 | WNT2 | Wnt family member 2 | 7472 |
| WNT 3 | WNT3 | Wnt family member 3 | 7473 |
| CXCR4 | CXCR4 | C-X-C motif chemokine receptor 4 | 7852 |
| CXCL10 | CXCL10 | C-X-C motif chemokine ligand 10 | 3627 |
| VEGFR1 | FLT1 | fms related tyrosine kinase 1 | 2321 |
| FGF2 | FGF2 | fibroblast growth factor 2 | 2247 |
| TNC | TNC | tenascin C | 3371 |
| TNW (TNN) | TNN | Tenascin W | 63923 |
| SEMA3A | SEMA3A | semaphorin 3A | 10371 |
| NRP1 | NRP1 | neuropilin-1 | 8829 |
| NRP2 | NRP2 | neuropilin-2 | 8828 |
| PLXNA1 | PLXNA1 | plexin A1 | 5361 |
| PLXNB1 | PLXNB1 | plexin B1 | 5364 |
| INTB1 (ITGB1) | ITGB1 | Integrin subunit beta1 | 3688 |

In a more particular embodiment, the markers of the migration activity are selected from the group consisting of ABL1, ALK, BRAF, CMET, EGFR, FGFR1, FGFR2, FGFR3, IGF1R, IntαV (ITGA5), JAG1, MEK 1 (MAP2K1), MEK 2 (MAP2K2), MMP9, PDGFRA, PDGFRB, RET, CXCL12 (SDF1), VEGFA, VEGFR2 (KDR), VEGFR3 (FLT4), CEACAM-1, CEACAM-5, PI3K alpha (PIK3CA), AKT1, C-RAF (RAF1), ABL2, FGFR4, HER4 (ERBB4), KIT, mTOR, NOTCH 1, NOTCH 2, EPHA1, ANGPT1, Tie2 (TEK), RHOA, ROCK 1, ROCK 2, MMP2, DDR1, DDR2, HMGB1, TGFb 1, TGFb 2 (LDS4), MYC, WNT 2, WNT 3, CXCR4 and CXCL10.

In a preferred embodiment, the markers of the migration activity are selected from the group consisting of CMET, EGFR, JAG1, MMP9, PDGFRA, CXCL12 (SDF1), VEGFA, VEGFR2 (KDR) and MMP2.

In a particular embodiment, the set of genes comprises
(i) markers of the tumor status of the sample comprising
  at least one marker of inflammation,
  at least one marker of cancer stem cells,
  at least one marker of hypoxia,
  at least one marker of cell death,
  at least one marker of posttranslational modifications and
  at least one marker of proliferation;
(ii) markers of the angiogenic and lymphangiogenic status of the sample comprising
  at least one marker of microvessel density,
  at least one marker of endothelial stem or progenitor cells,
  at least one marker of pro-angiogenic/pro-lymphangiogenic factors and
  at least one marker of receptors for pro-angiogenesis/pro-lymphangiogenesis;

(iii) markers of the tumor microenvironment of the sample comprising
at least one marker of extracellular components and their receptors and
at least one marker of extracellular component regulators; and
(iv) markers of the migration activity of tumor cells of the sample comprising
at least one marker of pro-migratory factors,
at least one marker of receptors for pro-migratory factors,
at least one marker of epithelial to mesenchymal transition and
at least one marker of actin cytoskeleton regulators associated with cell migration.

In another particular embodiment, the set of genes comprises (i) at least one, two, three or four, preferably at least 5, 6, 7, 8, 9, 10 or 11, more preferably at least 12, markers of the tumor status selected from the group consisting of the genes listed in Table 1, preferably from the group consisting of ABL1, ALK, B7-H3 (CD276), BCL2, BRAF, CD133 (PROM1), CMET, CTLA4, EGFR, FGFR1, FGFR2, FGFR3, HER2, ERBB3, HIF1A, IGF1R, IntαV (ITGA5), JAG1, MEK 1 (MAP2K1), MEK 2 (MAP2K2), MMP9, PDL1 (CD274), RET, CXCL12 (SDF1), VEGFA, VEGFR2 (KDR), VEGFR3 (FLT4), CEACAM-1, CEACAM-5, PI3K alpha (PIK3CA), AKT1, AR (androgen receptor), HDAC1, HDAC2, C-RAF (RAF1), PD1, MDM2, CDK4, CDK6, IDO1, ABL2, FGFR4, HER4 (ERBB4), KIT, EZH2, IDH1, IDH2, VHL, mTOR, TRAIL-R1 (TNFRSF10A), TRAIL-R2 (TNFRSF10B), CD39 (ENTPD1), CREBBP, EP300, BRD4, GRB2, NOTCH 1, NOTCH 2, EPHA1, ANGPT1, Tie2 (TEK), RHOA, MMP2, DDR1, DDR2, KDM1A (LSD1), FOXP3, CD27, ICOS (CD278), IL4, IL13, HMGB1, FPR1, TGFb 1, TGFb 2 (LDS4), CD40, IL6, CTNNB1, MYC, WNT 2, WNT 3, CXCR4, CXCL10, TLR4, IL2RB, PDL2 (PDCD1LG2) and KIR2DL5A, more preferably selected from the group consisting of BCL2, CD133 (PROM1), CMET, EGFR, HER2, HIF1A, JAG1, MMP9, CXCL12 (SDF1), VEGFA, VEGFR2 (KDR) and MMP2;

ii) at least one, two, three or four, preferably at least 5, 6, 7 or 8, more preferably at least 9 markers of the angiogenic and lymphangiogenic status selected from the group consisting of the genes listed in Table 2, preferably from the group consisting of BRAF, EGFR, FGFR1, FGFR2, FGFR3, HER2, ERBB3, IGF1R, IntαV (ITGA5), JAG1, MEK 1 (MAP2K1), MEK 2 (MAP2K2), MMP9, PDGFRA, PDGFRB, CXCL12 (SDF1), VEGFA, VEGFR2 (KDR), VEGFR3 (FLT4), CEACAM-1, CEACAM-5, PI3K alpha (PIK3CA), AKT1, C-RAF (RAF1), FGFR4, HER4 (ERBB4), mTOR, NOTCH 1, NOTCH 2, EPHA1, ANGPT1, Tie2 (TEK), MMP2, CD34, CXCR4, preferably selected from the group consisting of EGFR, HER2, JAG1, MMP9, PDGFRA, CXCL12 (SDF1), VEGFA, VEGFR2 (KDR) and MMP2, more preferably selected from the group consisting of EGFR, HER2, JAG1, MMP9, PDGFRA, CXCL12 (SDF1), VEGFA, VEGFR2 (KDR) and MMP2;

iii) at least one or 2, preferably at least 3 or 4, more preferably at least 5, markers of the tumor microenvironment selected from the group consisting of the genes listed in Table 3, preferably from the group consisting of ABL1, ALK, CMET, IntαV (ITGA5), MEK 1 (MAP2K1), MEK 2 (MAP2K2), MMP9, RET, VEGFA, VEGFR2 (KDR), VEGFR3 (FLT4), CEACAM-1, CEACAM-5, ABL2, HER4 (ERBB4), mTOR, NOTCH 1, NOTCH 2, EPHA1, ANGPT1, Tie2 (TEK), RHOA, ROCK 1, ROCK 2, MMP2, DDR1 and DDR2, more preferably selected from the group consisting of CMET, MMP9, VEGFA, VEGFR2 (KDR) and MMP2; and iv) at least one, two, three or four, preferably at least 5, 6, 7 or 8, more preferable at least 9, markers of the cell migration activity selected from the group consisting of the genes listed in Table 4, preferably from the group consisting of ABL1, ALK, BRAF, CMET, EGFR, FGFR1, FGFR2, FGFR3, IGF1R, IntαV (ITGA5), JAG1, MEK 1 (MAP2K1), MEK 2 (MAP2K2), MMP9, PDGFRA, PDGFRB, RET, CXCL12 (SDF1), VEGFA, VEGFR2 (KDR), VEGFR3 (FLT4), CEACAM-1, CEACAM-5, PI3K alpha (PIK3CA), AKT1, C-RAF (RAF1), ABL2, FGFR4, HER4 (ERBB4), KIT, mTOR, NOTCH 1, NOTCH 2, EPHA1, ANGPT1, Tie2 (TEK), RHOA, ROCK 1, ROCK 2, MMP2, DDR1, DDR2, HMGB1, TGFb 1, TGFb 2 (LDS4), MYC, WNT 2, WNT 3, CXCR4 and CXCL10, preferably selected from the group consisting of CMET, EGFR, JAG1, MMP9, PDGFRA, CXCL12 (SDF1), VEGFA, VEGFR2 (KDR) and MMP2.

Any of these markers may be replaced by another marker reflecting the same pathway or the same target.

It should be noted that the same gene can be a marker for different features.

The genes selected to be included into the set preferably encode proteins that can be targeted by a therapeutic agent. In particular, the set of genes has to include the therapeutic targets for which a predictive rank of efficacy has to be determined. Preferably, therapeutic targets are chosen among markers encoding tyrosine kinase receptors or ligands thereof.

However, the set of genes may also include non-targetable genes, i.e. genes that are only representative of a signaling pathway, said signaling pathway comprising a therapeutic target.

In an embodiment, the set of genes comprises
SDF1, BCL2, CD133, HIF1A and/or PARG, preferably SDF1, BCL2, CD133 and/or HIF1A as markers of the tumor status,
CD34, VEGFA, VEGFR1, VEGFR2 and/or JAG1, preferably VEGFA, VEGFR1, VEGFR2 and/or JAG1, more preferably CD34, VEGFA, VEGFR2 and/or JAG1 as markers of the angiogenic and lymphangiogenic status,
MMP9, MMP2, TNC, TNW and/or INTB1, preferably MMP9, MMP2, TNC and/or INTB1, more preferably MMP9 and/or MMMP2 as markers of the tumor microenvironment, and/or
cMET, FGF2, PDGFRA, HER2, EGFR, SEMA3, NRP1, NRP2, PLEXA1 and/or PLEXB1, preferably cMET, FGF2, PDGFRA, HER2, EGFR, SEMA3, NRP1, NRP2 and/or PLEXA1, more preferably cMET, PDGFRA, HER2 and/or EGFR as markers of the migration activity.

In a particular embodiment, the set of genes comprises SDF1, BCL2, CD133, HIF1A, PARG, CD34, VEGFR1, VEGFR2, VEGFA, JAG1, MMP2, MMP9, TNC, TNW, SEMA3, NRP1, NRP2, PLEXA1, PLEXB1, INTB1, PDGFRA, c-MET, EGFR, HER2 and/or FGF2, preferably SDF1, BCL2, CD133, HIF1A, PARG, CD34, VEGFR1, VEGFR2, VEGFA, JAG1, MMP2, MMP9, TNC, TNW, SEMA3, NRP1, NRP2, PLEXA1, PLEXB1, INTB1, PDGFRA, c-MET EGFR, HER2 and FGF2, more preferably SDF1, BCL2, CD133, HIF1A, PARG, VEGFR1, VEGFR2, VEGFA, JAG1, MMP2, MMP9, TNC, SEMA3, NRP1, NRP2, PLEXA1, INTB1, PDGFRA, c-MET, EGFR, HER2 and/or FGF2, and even more preferably SDF1, BCL2, CD133, HIF1A, VEGFR2, VEGFA, JAG1, MMP2, MMP9, PDGFRA, c-MET, EGFR and/or HER2. Any of these markers may be replaced by another marker reflecting the same pathway or the same target.

In another particular embodiment, the set of genes comprises (i) at least HIF1A, SDF1, MMP9, JAG1, BCL2 and CD133 genes and (ii) other markers of the tumor status, the angiogenic and lymphangiogenic status, the tumor microenvironment, and the migration activity, preferably selected from the group consisting of the genes listed in Tables 1 to 4, more preferably selected from the group consisting of ABL1, ALK, B7-H3 (CD276), BRAF, CMET, CTLA4, EGFR, FGFR1, FGFR2, FGFR3, HER2, ERBB3, IGF1R, IntαV (ITGA5), MEK 1 (MAP2K1), MEK 2 (MAP2K2), PDGFRA, PDGFRB, PDL1 (CD274), RET, VEGFA, VEGFR2 (KDR), VEGFR3 (FLT4), CEACAM-1, CEACAM-5, PI3K alpha (PIK3CA), AKT1, AR (androgen receptor), HDAC1, HDAC2, C-RAF (RAF1), PD1, MDM2, CDK4, CDK6, IDO1, ABL2, FGFR4, HER4 (ERBB4), KIT, EZH2, IDH1, IDH2, VHL, mTOR, TRAIL-R1 (TNFRSF10A), TRAIL-R2 (TNFRSF10B), CD39 (EN-TPD1), CREBBP, EP300, BRD4, GRB2, NOTCH 1, NOTCH 2, EPHA1, ANGPT1, Tie2 (TEK), RHOA, ROCK 1, ROCK 2, MMP2, CD34, DDR1, DDR2, KDM1A (LSD1), FOXP3, CD27, ICOS (CD278), IL4, IL13, HMGB1, FPR1, TGFb 1, TGFb 2 (LDS4), CD40, IL6, CTNNB1, MYC, WNT 2, WNT 3, CXCR4, CXCL10, TLR4, IL2RB, PDL2 (PDCD1LG2) and KIR2DL5A.

In a preferred embodiment, the set of genes comprises at least 20, 30, 40, 50, 60, 70, 80 or 90 genes selected from the group consisting of the genes listed in Tables 1 to 4, preferably selected from the group consisting of ABL1, ALK, B7-H3 (CD276), BCL2, BRAF, CD133 (PROM1), CMET, CTLA4, EGFR, FGFR1, FGFR2, FGFR3, HER2, ERBB3, HIF1A, IGF1R, IntαV (ITGA5), JAG1, MEK 1 (MAP2K1), MEK 2 (MAP2K2), MMP9, PDGFRA, PDG-FRB, PDL1 (CD274), RET, CXCL12 (SDF1), VEGFA, VEGFR2 (KDR), VEGFR3 (FLT4), CEACAM-1, CEACAM-5, PI3K alpha (PIK3CA), AKT1, AR (androgen receptor), HDAC1, HDAC2, C-RAF (RAF1), PD1, MDM2, CDK4, CDK6, IDO1, ABL2, FGFR4, HER4 (ERBB4), KIT, EZH2, IDH1, IDH2, VHL, mTOR, TRAIL-R1 (TNFRSF10A), TRAIL-R2 (TNFRSF10B), CD39 (EN-TPD1), CREBBP, EP300, BRD4, GRB2, NOTCH 1, NOTCH 2, EPHA1, ANGPT1, Tie2 (TEK), RHOA, ROCK 1, ROCK 2, MMP2, CD34, DDR1, DDR2, KDM1A (LSD1), FOXP3, CD27, ICOS (CD278), IL4, IL13, HMGB1, FPR1, TGFb 1, TGFb 2 (LDS4), CD40, IL6, CTNNB1, MYC, WNT 2, WNT 3, CXCR4, CXCL10, TLR4, IL2RB, PDL2 (PDCD1LG2) and KIR2DL5A. In a more particular embodiment, the set of genes comprises all of these genes. Any of these markers may be replaced by another marker reflecting the same pathway or the same target.

In preferred embodiments, the set of genes for which the expression levels are provided or determined, comprises less than 10 000, 9000, 8000, 7000, 6000, 5000, 4000, 3000, 2000, 1000 different genes, preferably less than 900, 800, 700, 600, 500, 400, 300, 200, 150, 120 or 100 genes, and more preferably less than 90, 80, 70, 60, 50, 40 or 30 genes.

In particular, the set of genes included in the signature may comprise from 10 to 1000 genes, more particularly from 10, 12, 14, 16, 18, 20, 22, 24, 26, 30, 40, 50, 60, 70, 80, 90 to 200 genes, and even more particularly from 10, 20, 30, 40, 50, 60, 70, 80, 90 to 150 or 100 genes.

As shown in the experimental section, raw data of expression levels (e.g. expressed as $2\text{-}2^{-\Delta Ct}$ where $\Delta Ct$ corresponds to the variation of a given gene expression compared to the averaged expression of the two internal reference genes 18S and GAPDH) do not allow the identification of dominant signaling pathways in a cancer sample.

The inventors showed that these pathways can be revealed by a normalization process defined as multiple rounds of comparisons of expression of genes of interest in reference normal tissue, low grade or benign tumor tissue and major cell types of the tissue.

Accordingly, in step b) of the method of the invention, each expression level provided in step a) is compared to the expression level of the same gene
- in the organ from which said cancer originates, i.e. in a normal tissue corresponding to, or histologically matched to, said cancer,
- in at least one low grade or benign, preferably low grade, tumor tissue corresponding, or histologically matched, to said cancer and
- in at least one normal cellular subtype of the organ from which said cancer originates, i.e. at least one normal cellular subtype that can be found in a tissue histologically matched to said cancer.

The tissues and cell types of reference depend on the type of cancer and may be easily defined by the skilled person.

The method of the invention may further comprise, before step b), providing
- a sample of organ from which said cancer originates, i.e. a sample of normal tissue corresponding to, or histologically matched to, said cancer,
- a sample of low grade or benign, preferably low grade, tumor tissue corresponding, or histologically matched, to said cancer and/or
- a sample of at least one normal cellular subtype of the organ from which said cancer originates.

The samples of tissues and cell types of reference may be provided from the patient affected with a cancer, from another subject or from a healthy subject, i.e. a subject who does not suffer from a cancer. Samples of tissues and cell types of reference may also be provided from tissue banks.

The method may further comprise determining the expression levels in said samples of the set of genes representative of several therapeutically targetable signaling pathways and described above.

The normal tissue or organ does not contain any tumoral cells and preferably comprises a plurality of cellular subtypes and preferably all, or almost all, cellular subtypes from which the cancer can be originated. In case of metastasis, the organ from which the cancer originates can be different that the final localization of the tumor.

The low grade or benign tumor tissue is chosen according to international recognized nomenclatures defined and used by scientific and medical organizations (i.e. World Health Organization WHO; Union for International Cancer Control UICC; American Joint Committee on Cancer). Preferably, as used herein "low grade tumor" refers to Grade I and II tumors or stage O or I according to the TNM cancer staging notation system. The term "benign tumor" is used herein to refer to a tumor which is not-malignant, i.e. does not grow in an unlimited, aggressive manner, does not invade surrounding tissues, and does not metastasize. The skilled person may easily choose low grade or benign tumor according to the type cancer. One or several (e.g. 2 or 3) low grade and/or benign tumors may be used as references.

Depending on the type of cancer, one, two, three or more major tissue cellular subtypes may be used as references. Cellular subtypes preferentially reflect the normal composition of non-tumoral tissues or organs from which the cancer originates. For example, for brain tumors, cellular subtypes may be neurons, astrocytes, oligodendrocytes, endothelial cells and/or microglial cells. The skilled person may easily choose tissue cellular subtypes according to the type cancer, and in particular according to the cellular type(s) from which said cancer originates. One or several (e.g. 2, 3 or 4) cellular types may be used as references. Preferably, at least one of the cellular type is a cellular type from which said cancer originates or from which said cancer is suspected to originate.

In a particular embodiment, the cancer sample is from glioma, and preferably from glioblastoma and, in step b) of the method of the invention, the expression level of each gene of the set in the cancer sample, is compared to the expression level of the same gene
  in normal brain, i.e. the normal organ from which said cancer originates,
  in at least a low grade glioma, e.g. astrocytoma grade I or II, i.e. a low grade or benign tumor tissue, and
  in at least normal brain astrocytes, oligodendrocytes and/or neuronal cells, preferably normal brain astrocytes and oligodendrocytes, i.e. normal cellular subtypes of the organ from which said cancer originates.

In another particular embodiment, the cancer sample is from colon cancer and, in step b) of the method of the invention, the expression level of each gene of the set in the cancer sample, is compared to the expression level of the same gene
  in normal colon or in colonic smooth muscle cells, i.e. a normal tissue or organ,
  in at least a non cancerous polyp or a low grade colon tumor (grade I or II), preferably a polyp, i.e. a low grade or benign tumor tissue, and
  in at least normal colonic epithelial cells, i.e. normal cellular subtype of the organ from which said cancer originates.

In a further particular embodiment, the cancer sample is from prostate cancer and, in step b) of the method of the invention, the expression level of each gene of the set in the cancer sample, is compared to the expression level of the same gene
  in a normal prostate, i.e. the normal organ or tissue,
  in at least a low grade prostate tumor (grade I or II) or benign prostatic hyperplasia, i.e. a low grade or benign tumor tissue, and
  in at least normal prostate epithelial cells, prostate microvascular endothelial cells and/or prostate fibroblasts, i.e. normal cellular subtypes of the organ from which said cancer originates.

In a further particular embodiment, the cancer sample is from skin cancer and, in step b) of the method of the invention, the expression level of each gene of the set in the cancer sample, is compared to the expression level of the same gene
  in normal skin tissue, i.e. the normal organ or tissue,
  in at least a low grade melanoma (stage 0), i.e. a low grade or benign tumor tissue, and
  in at least normal epidermal epithelial cells, dermal epithelial cells, keratinocytes, melanocytes, Langerhans cells, Merkel cells and/or skin endothelial cells, i.e. normal cellular subtypes of the organ from which said cancer originates.

In a further particular embodiment, the cancer sample is from lung cancer and, in step b) of the method of the invention, the expression level of each gene of the set in the cancer sample, is compared to the expression level of the same gene
  in normal lung, i.e. the normal organ or tissue,
  in at least a low grade lung tumor (grade I or II), i.e. a low grade or benign tumor tissue, and
  in at least normal lung smooth muscular cells, lung fibroblasts, alveolar epithelial cells, bronchial epithelial cells and/or tracheal epithelial cells, i.e. normal cellular subtypes of the organ from which said cancer originates.

In a further particular embodiment, the cancer sample is from pancreas cancer and, in step b) of the method of the invention, the expression level of each gene of the set in the cancer sample, is compared to the expression level of the same gene
  in normal pancreas, i.e. the normal organ or tissue,
  in at least a low grade pancreas tumor (grade I or II), i.e. a low grade or benign tumor tissue, and
  in at least normal pancreas endothelial cells, acinar cells, centroacinar cells, duct cells, stellate cells and/or islets cells (Langerhans), i.e. normal cellular subtypes of the organ from which said cancer originates.

In a further particular embodiment, the cancer sample is from liver cancer and, in step b) of the method of the invention, the expression level of each gene of the set in the cancer sample, is compared to the expression level of the same gene
  in normal liver, i.e. the normal organ or tissue,
  in at least a low grade liver tumor (grade I or II), i.e. a low grade or benign tumor tissue, and
  in at least normal hepatocytes, liver endothelial cells and/or Kupffer Cells, i.e. normal cellular subtypes of the organ from which said cancer originates.

In a further particular embodiment, the cancer sample is from kidney cancer and, in step b) of the method of the invention, the expression level of each gene of the set in the cancer sample, is compared to the expression level of the same gene
  in normal kidney, i.e. the normal organ or tissue,
  in at least a low grade kidney tumor (grade I or II), i.e. a low grade or benign tumor tissue, and
  in at least normal mesangial cells, stroma cells, glomerular endothelial cells, podocytes, epithelial cells, cortical epithelial cells and/or tubular cells, i.e. normal cellular subtypes of the organ from which said cancer originates.

In a further particular embodiment, the cancer sample is from a head and neck cancer and, in step b) of the method of the invention, the expression level of each gene of the set in the cancer sample, is compared to the expression level of the same gene
  in the normal organ or tissue, i.e. in the larynx, throat, lips, mouth, nose or salivary glands depending on the exact tumor location;
  in at least a low grade head and neck tumor (grade I or II), i.e. a low grade or benign tumor tissue, and
  in at least normal cells from the oral cavity (e.g. mouth floor, tongue), normal cells from oropharynx (e.g. tonsil, tongue base, velum, larynx) and/or normal cells from hypopharynx (e.g. piriform sinus), i.e. normal cellular subtypes of the organ from which said cancer originates.

In a further particular embodiment, the cancer sample is from breast cancer and, in step b) of the method of the invention, the expression level of each gene of the set in the cancer sample, is compared to the expression level of the same gene in normal breast, i.e. the normal organ or tissue,
in at least a low grade breast tumor (grade I or II), i.e. a low grade or benign tumor tissue, and
in at least normal breast fibroblasts and/or epithelial cells (e.g. duct cells, lobule cells), i.e. normal cellular subtypes of the organ from which said cancer originates.

Optionally, immune cells infiltrating the organ of interest may be further included as normal cellular subtypes.

The expression levels of each gene of the set in these reference tissues or cell types may be determined by any method as described above, preferably by the same method as used for the cancer sample.

In preferred embodiments, the expression levels of each gene in these reference tissues or cell types are determined by quantitative RT-PCR.

The variations of expression levels of each gene of the set provided in step a) of the method of the invention are compared to expression levels of said genes in each reference tissue or cell type as described above.

In preferred embodiments, expression levels are determined by quantitative RT-PCR and the variations are obtained by the method commonly known as the ΔΔCt method:

$$\Delta\Delta Ct(\text{organ}) = \Delta Ct(\text{cancer sample}) - \Delta Ct(\text{organ sample})$$

where

ΔCt (cancer sample)=Ct (target gene in the cancer sample)− Ct (housekeeping gene in the cancer sample), and ΔCt (organ sample)=Ct (target gene in the sample of organ from which the cancer originates)−Ct (housekeeping gene in the sample of organ from which the cancer originates)

$$\Delta\Delta Ct(\text{low grade or benign tumor tissue}) = \Delta Ct(\text{cancer sample}) - \Delta Ct(\text{low grade or benign tumor tissue sample})$$

where

ΔCt (cancer sample)=Ct (target gene in the cancer sample)− Ct (housekeeping gene in the cancer sample), and ΔCt (low grade or benign tumor tissue sample)=Ct (target gene in the sample of low grade or benign tumor tissue)−Ct (housekeeping gene in the sample of low grade or benign tumor tissue)

$$\Delta\Delta Ct(\text{normal cellular subtype}) = \Delta Ct(\text{cancer sample}) - \Delta Ct(\text{normal cellular subtype})$$

where

ΔCt (cancer sample)=Ct (target gene in the cancer sample)− Ct (housekeeping gene in the cancer sample), and ΔCt (normal cellular subtype sample)=Ct (target gene in the sample of normal cellular subtype)−Ct (housekeeping gene in the sample of normal cellular subtype)

The variation of the expression level of each gene of the set obtained in the cancer sample compared to the expression level of said gene in a reference tissue or cell type (i.e. in a sample of organ from which the cancer originates, in a sample of low grade or benign tumor tissue corresponding, or histologically matched, to the cancer, and in a sample of normal cellular subtype(s) of the organ from which the cancer originates) can thus be obtained by taking $2^{-\Delta Ct}$.

In step c) of the method of the invention, a score is calculated for each gene of the set and represents the global variation amplitude of the expression of the gene in the cancer sample compared to the expression in normal organ or tissue, low grade or benign tumor tissue(s) and tissue cellular subtype(s). The score is proportional to the absolute value of the global variation amplitude of the expression of the gene.

In an embodiment, the score of each gene is obtained by adding up the variations determined in each reference tissue or cell type.

In preferred embodiments, expression levels are determined by quantitative RT-PCR and the score for each gene is obtained as follow:

$$\text{score} = 2^{-\Delta\Delta Ct}(\text{organ}) + \sum_{k=1}^{n} [2^{-\Delta\Delta Ct}(\text{low grade or benign tumor tissue})_k] + \sum_{i=1}^{m} [2^{-\Delta\Delta Ct}(\text{cellular subtype})_i]$$

wherein n and m are positive integers and are identical or different.

The score for each gene is thus obtained by adding up the $2^{-\Delta\Delta Ct}$ value obtained for each reference tissue or cell type (i.e. score=$2^{-\Delta\Delta Ct}$ (reference tissue or cell type 1)+$2^{-\Delta\Delta Ct}$ (reference tissue or cell type 2)+ . . . +$2^{-\Delta\Delta Ct}$ (reference tissue or cell type n)).

In a particular embodiment, the score for each gene is obtained as follow:

score=$2^{-\Delta\Delta Ct}$(organ)+$2^{-\Delta\Delta Ct}$(low grade or benign tumor tissue 1)+ . . . +$2^{-\Delta\Delta Ct}$(low grade or benign tumor tissue $n$)+$2^{-\Delta\Delta Ct}$(cellular subtype 1)+ . . . +$2^{-\Delta\Delta Ct}$(cellular subtype $m$)

wherein n and m are positive integers and are identical or different.

In preferred embodiments, m is 1 or 2 and n is 1 or 2.

In other preferred embodiments, expression levels are determined using techniques allowing direct quantification of each RNA molecule in a given sample (e.g. nanostring or microfluidic PCR) and the variation of the expression level of each gene of the set obtained in the cancer sample compared to the expression level of said gene in a reference tissue or cell type may be obtained using the following calculation:

Variation of the expression level of a gene in the cancer sample compared to the expression level of said gene in a reference tissue or cell type=|RNA quantity in the cancer sample−RNA quantity in the reference tissue or cell type| wherein RNA quantities in the cancer sample and in the reference tissue or cell type are preferably normalized with the RNA quantities of one or two housekeeping genes.

In these embodiments, the score for each gene is obtained by adding up the variations compared to the normal organ or tissue, low grade or benign tumor tissue(s) and tissue cellular subtype(s).

As shown in the experimental section, the obtained scores are specific for each patient.

Optionally, the scores obtained for each gene of the set can be normalized by attributing an arbitrary value to the highest score.

In step d) of the method of the invention, the genes of the set, i.e. representative of therapeutically targetable signaling pathways, are ranked according to calculated scores thereby allowing to identify the dominant signaling pathway(s) of the cancer sample, i.e. the pathway(s) corresponding to the genes having the highest ranks. These dominant pathways are considered as the best therapeutic targets.

Preferably, the top three therapeutically targetable genes are considered as the dominant signaling pathways and thus as the best therapeutic targets.

In another embodiment, the top two therapeutically targetable genes are considered as the dominant signaling pathways.

In a further embodiment, the first ranked therapeutically targetable gene determines the dominant signaling pathway and the best therapeutic target.

Based on these results, monotherapy (e.g., targeting one of the first ranked therapeutically targetable signaling pathways such as one of the three first ranked therapeutically targetable signaling pathways, preferably the first ranked therapeutically targetable signaling pathway) or combined therapy (e.g., targeting one, two or all of the first ranked therapeutically targetable signaling pathways, such as the top three pathways) can be contemplated.

Accordingly, in a second aspect, the present invention relates to a method for determining a treatment protocol for a subject having cancer, the method comprising determining the therapeutically targetable dominant signaling pathways in a cancer sample from said subject according to the method of the invention as disclosed above and determining a treatment protocol that targets at least one of these dominant pathways, preferably at least one of the top three therapeutically targetable pathways or genes, more preferably at least one of the top two therapeutically targetable pathways or genes, and even more preferably at least the first ranked therapeutically targetable pathway or gene.

In a preferred embodiment, the treatment protocol is designed to target two or three dominant pathways, in particular two or three therapeutically targetable genes, preferably using combined therapy.

Examples of therapeutic agents that may be used to target genes of the signature are presented in table 1 below. These examples should be regarded as illustrative and not limiting.

TABLE 5

Examples of therapeutic agents targeting genes representative of signaling pathways

| Targets | Therapeutic agents |
| --- | --- |
| SDF1 | Plerixafor, NOX-A12 |
| BCL2 | ABT-199 (Venetoclax), Genasense (G3139), ABT-737, ABT-263, Venetoclax, SPC2996 |
| CD133 | XAV-939 |
| HIF1A | Digoxin, Bortezomib, RO7070179, EZN-2968 |
| PARG | GPI 16552 |
| VEGFA | Bevacizumab (or Avastin), aflibercept |
| VEGFR1 | Vandatenib, Pasopanib, Sunitinib, Axitinib, Regorafenib |
| VEGFR2 | Cediranib, Ponatinib, Regorafenib, ramucirumab, BR55, ZD6474 |
| MMP9 | The synthetic peptide PCK3145, Marimastat, GS-5745 |
| MMP2 | Incyclidine, Marimastat |
| ITGB1 | Cilengitide |
| CMET | Crizotinib, SU11274, cabozantinib, Tivantinib, capmatinib (INC280), AMG 337, Tepotinib (MSC2156119J) |
| FGF2 | Vargatef, AZD4547 |
| PDGFRA | Imatinib, Axitinib, Olaratumab (LY3012207, IMC-3G3), MEDI-575, crenolanib, DCC-2618 |
| HER2 | Trastuzumab (Herceptin ®), Lapatinib, Afatinib, pertuzumab, MM-111 |
| EGFR | Lapatinib, Afatinib, Cetuximab, Erlotinib, Osimertinib (AZD9291), Gefitinib (ZD-1839) |
| NRP1 | MTP-NRP1 peptidic antagonists described in the patent application WO 2007/000672 |
| NRP2 | MTP-NRP2 peptidic antagonists described in the patent application WO 2007/000672 |
| PLEXA1 | MTP-PLEXA1 peptidic antagonists described in the patent application WO 2007/000672 |
| JAG | RO4929097, LY3039478 |
| TNC | Neuradiab (Bradmer Pharmaceuticals Inc.) |
| PI3K alpha | GSK2636771, Wortmannin, XL147, Alpelisib (BYL719) |
| AKT1 | ARQ 751, AZD5363, BAY1125976 |
| PDL1 (CD274) | Atezolizumab (MPDL3280A), avelumab, durvalumab, pembrolizumab |
| VEGFR3 (FLT4) | axitinib, Famitinib, AG-013736 |
| AR (androgen receptor) | Bicalutamide, Flutamide |
| CXCR4 | BMS-936564, BKT140, BL-8040, USL311, Plerixafor, LY2510924, MSX-122 |
| CEACAM-5 | CEA inhibitors, SAR408701 |
| IGF1R | Cixutumumab, Figitumumab (CP-751871), Linsitinib (OSI-906), BIIB022, AVE1642, IMC-A12, RG1507 |
| ALK | Crizotinib, ceritinib, alectinib |
| C-RAF (RAF1) | dabrafenib trametinib |
| ABL1 | Dasatinib, bosutinib, imatinib, nilotinib |
| GRB2 | Dasatinib, BP1001 |
| MYC | DCR-MYC |
| IDO1 | Epacadostat (INCB024360), GDC-0919, Indoximod |
| mTOR | everolimus, Temsirolimus, SAR245409, MLN0128 |
| RHOA | Fasudil, Y39983, BA-210 |
| ROCK 1 | Fasudil, Y39983, BA-210 |
| ROCK 2 | Fasudil, Y39983, BA-210 |
| TLR4 | GSK1795091, TLR4 Agonist GLA-SE |

TABLE 5-continued

Examples of therapeutic agents targeting genes representative of signaling pathways

| Targets | Therapeutic agents |
| --- | --- |
| ICOS (CD278) | GSK3359609, MEDI-570 |
| IDH1 | IDH1 peptide vaccine, AG120, AG221, AG881, azacitidine, BAY1436032 |
| ABL2 | imatinib |
| KIR2DL5A | IPH2101, Lirilumab, Anti-KIR (1-7F9) |
| CD39 (ENTPD1) | IPH52, PSB 069 |
| CTLA4 | Ipilimumab, tremelimumab, MDX-010, AGEN 1884 |
| BRD4 | JQ1, PFI1, OTX015 |
| HER4 (ERBB4) | KBP-5209, ASLAN001 |
| FGFR1 | Lenvatinib, Nintedanib (BIBF 1120), GSK3052230 |
| FGFR2 | Lenvatinib, Nintedanib, BAY1187982 |
| FGFR4 | Lenvatinib, Nintedanib, FGF401, BLU-554, U3-1784 |
| FGFR3 | Lenvatinib, Nintedanib, LY3076226, B-701 |
| NOTCH 1 | LY3039478, MK0752 |
| NOTCH 2 | LY3039478, MK0752 |
| TRAIL-R1 (TNFRSF10A) | mapatumumab |
| TRAIL-R2 (TNFRSF10B) | mapatumumab |
| IL6 | mepolizumab |
| B7-H3 (CD276) | MGA271 |
| ERBB3 | MM-121, GSK2849330, U3-1287 (AMG888), MM-111 |
| PD1 | Nivolumab, pembrolizumab, Pidilizumab (CT-011) |
| MDM2 | nutlin, DS-3032, RO5503781 |
| KDM1A (LSD1) | OG-L002, GSK2879552, IMG-7289, INCB059872 |
| CDK4 | palbociclib (PD0332991), Ribociclib (LEE011), G1T28, Abemaciclib, |
| HDAC1 | panobinostat (LBH 589), vorinostat, Romidepsin (FR901228) |
| HDAC2 | panobinostat (LBH 589), vorinostat, Romidepsin (FR901228) |
| CREBBP | panobinostat, vorinostat, Romidepsin |
| EP300 | panobinostat, vorinostat, romidepsin, ep300i, BRD4i |
| IntαV (ITGA5) | PF-04605412 |
| CTNNB1 | PRI-724 |
| IL13 | QBX258, IL-13-PE, IL13-PE38QQR, |
| IL4 | QBX258, recombinant interleukin-4, |
| Tie2 (TEK) | RO6867461, CEP-11981 |
| IL2RB | Selectikine, ALT-801, Recombinant Human Interleukin-2 |
| KIT | Sunitinib, imatinib |
| PDGFRB | sunitinib, crenolanib, Axitinib, Sorafenib |
| EZH2 | Tazemetostat (EPZ-6438), GSK126, Azacitidine |
| MEK 1 (MAP2K1) | Trametinib, mekinist, Binimetinib (MEK162) |
| RET | Vandetanib, RXDX-105 |
| ANGPT1 | Vandetanib, regorafenib, Trebananib, CVX-241 |
| CD27 | Varlilumab (CDX-1127) |
| BRAF | Vemurafenib, Dabrafenib (GSK2118436), Encorafenib (LGX818) |
| WNT 2 | WNT974 |
| WNT 3 | WNT974 |

All embodiments disclosed for the method for determining the therapeutically targetable dominant signaling pathways in a cancer sample are also contemplated in this aspect.

In an embodiment, the method further comprises the step of providing a cancer sample from the subject and determining the expression levels of the set of genes representative of several therapeutically targetable dominant signaling pathways.

In another aspect, the present invention also relates to a method for selecting a subject affected with a cancer for therapy or determining whether a subject affected with a cancer is susceptible to benefit from a therapy, comprising determining the therapeutically targetable dominant signaling pathways in a cancer sample from said subject according to the method of the invention as disclosed above.

In this method, the subject is selected for the therapy or is susceptible to benefit from the therapy if the therapy targets at least one dominant pathway, preferably two or three dominant pathways.

In a preferred embodiment, the subject is selected for the therapy or is susceptible to benefit from the therapy if the therapy targets at least the first ranked therapeutically targetable pathway or gene.

All embodiments disclosed for the method for determining the therapeutically targetable dominant signaling pathways in a cancer sample are also contemplated in this aspect.

In an embodiment, the method further comprises the step of providing a cancer sample from the subject and determining the expression levels of the set of genes representative of several therapeutically targetable dominant signaling pathways.

In a further aspect, the present invention relates to a method for predicting clinical outcome of a subject affected with a cancer, comprising determining the therapeutically targetable dominant signaling pathways in a cancer sample from said subject according to the method of the invention.

In this method, the prognosis is good if the subject is treated with a therapy targeting at least one dominant pathway, preferably two or three dominant pathways.

In a preferred embodiment, the prognosis is good if the subject is treated with a therapy targeting at least the first ranked therapeutically targetable pathway or gene.

When the therapy does not target at least one therapeutically targetable dominant pathway, the prognosis may be improved by modifying the therapy in order to target at least one dominant pathway, preferably two or three dominant pathways.

All embodiments disclosed for the method for determining the therapeutically targetable dominant signaling pathways in a cancer sample are also contemplated in this aspect.

In an embodiment, the method further comprises the step of providing a cancer sample from the subject and determining the expression levels of the set of genes representative of several therapeutically targetable dominant signaling pathways.

In a further aspect, the present invention relates to a method of predicting the sensitivity of a cancer to a treatment comprising determining the therapeutically targetable dominant signaling pathways in a cancer sample from said subject according to the method of the invention as disclosed above. The cancer is considered potentially sensitive to the therapy if said therapy targets at least one of dominant pathways, preferably two or three dominant pathways.

In a preferred embodiment, the cancer is considered potentially sensitive to the therapy if said therapy targets at least the first ranked therapeutically targetable pathway or gene.

All embodiments disclosed for the method for determining the therapeutically targetable dominant signaling pathways in a cancer sample are also contemplated in this aspect.

In an embodiment, the method further comprises the step of providing a cancer sample from the subject and determining the expression levels of the set of genes representative of several therapeutically targetable dominant signaling pathways.

In a further aspect, the present invention relates to a method for treating a patient affected with a cancer comprising determining the therapeutically targetable dominant signaling pathways in a cancer sample from said subject according to the method of the invention as disclosed above, and administering a therapeutically efficient amount of therapy targeting at least one of dominant pathways.

Preferably, the therapy is a combined therapy targeting at least two or three of dominant pathways.

In a particular embodiment, the therapy targets at least the first ranked therapeutically targetable pathway or gene.

All embodiments disclosed for the method for determining the therapeutically targetable dominant signaling pathways in a cancer sample are also contemplated in this aspect.

In an embodiment, the method further comprises the step of providing a cancer sample from the subject and determining the expression levels of the set of genes representative of several therapeutically targetable dominant signaling pathways.

The present invention also relates to a method for screening or identifying a molecule suitable for treating a cancer, comprising determining the therapeutically targetable dominant signaling pathways in a cancer sample according to the method of the invention as disclosed above;

grafting tumor cells from said cancer sample in a non human animal model;

administering one or several candidate molecules to said model and analyzing the effect on the disease progression.

The efficiency of the molecule(s) can be evaluated, for instance, by analyzing the life span of animals, the occurrence of metastasis and/or the progression of the tumor. All these characteristics have to be compared with those of controls consisting of non human animal models with no treatment. Preferably, the non human animal model is immunodeficient mouse.

This method allows to establish a correlation between specific tumor signature and the therapy efficiency. Candidate molecules selected thanks to this method can thus be used in a patient affected with a cancer exhibiting similar dominant signaling pathways.

In another aspect, the present invention also relates to a kit comprising primers, probes and/or antibodies specific to the genes of the set, i.e. genes representative of the therapeutically targetable dominant signaling pathways, and optionally, a leaflet providing guidelines to use such a kit.

In particular the kit may comprise at least one pair of primers, probe or antibody specific to a marker of inflammation as described above, at least one pair of primers, probe or antibody specific to a marker of cancer stem cells as described above, at least one pair of primers, probe or antibody specific to a marker of hypoxia as described above, at least one pair of primers, probe or antibody specific to a marker of cell death as described above, at least one pair of primers, probe or antibody specific to a marker of posttranslational modifications as described above, at least one pair of primers, probe or antibody specific to a marker of proliferation as described above, at least one pair of primers, probe or antibody specific to a marker of microvessel density as described above, at least one pair of primers, probe or antibody specific to a marker of endothelial stem or progenitor cells as described above, at least one pair of primers, probe or antibody specific to a marker of pro-angiogenic/pro-lymphangiogenic factors as described above, at least one pair of primers, probe or antibody specific to a marker of receptors for pro-angiogenesis/pro-lymphangiogenesis as described above, at least one pair of primers, probe or antibody specific to a marker of extracellular components and their receptors as described above, at least one pair of primers, probe or antibody specific to a marker of extracellular component regulators as described above, at least one pair of primers, probe or antibody specific to a marker of pro-migratory factors as described above, at least one pair of primers, probe or antibody specific to a marker of receptors for pro-migratory factors as described above, at least one pair of primers, probe or antibody specific to a marker of epithelial to mesenchymal transition as described above, and/or at least one pair of primers, probe or antibody specific to a marker of actin cytoskeleton regulators associated with cell migration as described above.

In a particular embodiment, the kit comprises a pair of primers, a probe or an antibody specific to HIF1A, a pair of primers, a probe or an antibody specific to SDF1, a pair of primers, a probe or an antibody specific to MMP9, a pair of primers, a probe or an antibody specific to JAG1, a pair of primers, a probe or an antibody specific to BCL2, and/or a pair of primers, a probe or an antibody specific to CD133 genes.

The kit may further comprises a pair of primers, a probe or an antibody specific to at least one gene selected from the group consisting of PARG, CD34, VEGFR1, VEGFR2, VEGFA, MMIP2, TNC, TNW, SEMA3, NRP1, NRP2, PLEXA1, PLEXB1, INTB1, PDGFRA, c-MET EGFR, HER2 and FGF2, preferably from the group consisting of PARG, VEGFR1, VEGFR2, VEGFA, MMIP2, TNC, SEMA3, NRP1, NRP2, PLEXA1, INTB1, PDGFRA, c-MET, EGFR, HER2 and FGF2, preferably a pair of primers, a probe or an antibody specific to each of these genes.

In another embodiment, the kit comprises
(i) pairs of primers, probes or antibodies specific to at least one, two, three or four, preferably at least 5, 6, 7, 8, 9, 10 or 11, more preferably at least 12, markers of the tumor status selected from the group consisting of the genes listed in Table 1, preferably from the group consisting of ABL1, ALK, B7-H3 (CD276), BCL2, BRAF, CD133 (PROM1), CMET, CTLA4, EGFR, FGFR1, FGFR2, FGFR3, HER2, ERBB3, HIF1A, IGF1R, IntαV (ITGA5), JAG1, MEK 1 (MAP2K1), MEK 2 (MAP2K2), MMP9, PDL1 (CD274), RET, CXCL12 (SDF1), VEGFA, VEGFR2 (KDR), VEGFR3 (FLT4), CEACAM-1, CEACAM-5, PI3K alpha (PIK3CA), AKT1, AR (androgen receptor), HDAC1, HDAC2, C-RAF (RAF1), PD1, MDM2, CDK4, CDK6, IDO1, ABL2, FGFR4, HER4 (ERBB4), KIT, EZH2, IDH1, IDH2, VHL, mTOR, TRAIL-R1 (TNFRSF10A), TRAIL-R2 (TNFRSF10B), CD39 (ENTPD1), CREBBP, EP300, BRD4, GRB2, NOTCH 1, NOTCH 2, EPHA1, ANGPT1, Tie2 (TEK), RHOA, MMP2, DDR1, DDR2, KDM1A (LSD1), FOXP3, CD27, ICOS (CD278), IL4, IL13, HMGB1, FPR1, TGFb 1, TGFb 2 (LDS4), CD40, IL6, CTNNB1, MYC, WNT 2, WNT 3, CXCR4, CXCL10, TLR4, IL2RB, PDL2 (PDCD1LG2) and KIR2DL5A, more preferably selected from the group consisting of BCL2, CD133 (PROM1), CMET, EGFR, HER2, HIF1A, JAG1, MMP9, CXCL12 (SDF1), VEGFA, VEGFR2 (KDR) and MMP2;
ii) pairs of primers, probes or antibodies specific to at least one, two, three or four, preferably at least 5, 6, 7 or 8, more preferably at least 9 markers of the angiogenic and lymphangiogenic status selected from the group consisting of the genes listed in Table 2, preferably from the group consisting of BRAF, EGFR, FGFR1, FGFR2, FGFR3, HER2, ERBB3, IGF1R, IntαV (ITGA5), JAG1, MEK 1 (MAP2K1), MEK 2 (MAP2K2), MMP9, PDGFRA, PDGFRB, CXCL12 (SDF1), VEGFA, VEGFR2 (KDR), VEGFR3 (FLT4), CEACAM-1, CEACAM-5, PI3K alpha (PIK3CA), AKT1, C-RAF (RAF1), FGFR4, HER4 (ERBB4), mTOR, NOTCH 1, NOTCH 2, EPHA1, ANGPT1, Tie2 (TEK), MMP2, CD34, CXCR4, preferably selected from the group consisting of EGFR, HER2, JAG1, MMP9, PDGFRA, CXCL12 (SDF1), VEGFA, VEGFR2 (KDR) and MMP2, more preferably selected from the group consisting of EGFR, HER2, JAG1, MMP9, PDGFRA, CXCL12 (SDF1), VEGFA, VEGFR2 (KDR) and MMP2;
iii) pairs of primers, probes or antibodies specific to at least one or 2, preferably at least 3 or 4, more preferably at least 5, markers of the tumor microenvironment selected from the group consisting of the genes listed in Table 3, preferably from the group consisting of ABL1, ALK, CMET, IntαV (ITGA5), MEK 1 (MAP2K1), MEK 2 (MAP2K2), MMP9, RET, VEGFA, VEGFR2 (KDR), VEGFR3 (FLT4), CEACAM-1, CEACAM-5, ABL2, HER4 (ERBB4), mTOR, NOTCH 1, NOTCH 2, EPHA1, ANGPT1, Tie2 (TEK), RHOA, ROCK 1, ROCK 2, MMP2, DDR1 and DDR2, more preferably selected from the group consisting of CMET, MMP9, VEGFA, VEGFR2 (KDR) and MMP2; and
iv) pairs of primers, probes or antibodies specific to at least one, two, three or four, preferably at least 5, 6, 7 or 8, more preferable at least 9, markers of the cell migration activity selected from the group consisting of the genes listed in Table 4, preferably from the group consisting of ABL1, ALK, BRAF, CMET, EGFR, FGFR1, FGFR2, FGFR3, IGF1R, IntαV (ITGA5), JAG1, MEK 1 (MAP2K1), MEK 2 (MAP2K2), MMP9, PDGFRA, PDGFRB, RET, CXCL12 (SDF1), VEGFA, VEGFR2 (KDR), VEGFR3 (FLT4), CEACAM-1, CEACAM-5, PI3K alpha (PIK3CA), AKT1, C-RAF (RAF1), ABL2, FGFR4, HER4 (ERBB4), KIT, mTOR, NOTCH 1, NOTCH 2, EPHA1, ANGPT1, Tie2 (TEK), RHOA, ROCK 1, ROCK 2, MMP2, DDR1, DDR2, HMGB1, TGFb 1, TGFb 2 (LDS4), MYC, WNT 2, WNT 3, CXCR4 and CXCL10, preferably selected from the group consisting of CMET, EGFR, JAG1, MMP9, PDGFRA, CXCL 12 (SDF1), VEGFA, VEGFR2 (KDR) and MMP2.

In a further embodiment, the kit comprises
pairs of primers, probes or antibodies specific to SDF1, BCL2, CD133, HIF1A and/or PARG, preferably SDF1, BCL2, CD133 and/or HIF1A,
pairs of primers, probes or antibodies specific to CD34, VEGFA, VEGFR1, VEGFR2 and/or JAG1, preferably VEGFA, VEGFR1, VEGFR2 and/or JAG1, more preferably CD34, VEGFA, VEGFR2 and/or JAG1,
pairs of primers, probes or antibodies specific to MMP9, MMP2, TNC, TNW and/or INTB1, preferably MMP9, MMP2, TNC and/or INTB1, more preferably MMP9 and/or MMP2, and
pairs of primers, probes or antibodies specific to cMET, FGF2, PDGFRA, HER2, EGFR, SEMA3, NRP1, NRP2, PLEXA1 and/or PLEXB1, preferably cMET, FGF2, PDGFRA, HER2, EGFR, SEMA3, NRP1, NRP2 and/or PLEXA1, more preferably cMET, PDGFRA, HER2 and/or EGFR.

In another particular embodiment, the kit comprises pairs of primers, probes or antibodies specific to 1, 2, 3, 4, 5, 6, 7, 8, 9, 10, 11 or 12 genes selected from the group consisting of SDF1, BCL2, CD133, HIF1A, VEGFR2, VEGFA, JAG1, MMP2, MMP9, PDGFRA, c-MET, EGFR and HER2, preferably specific to all of these genes.

In another particular embodiment, the kit comprises (i) pairs of primers, probes or antibodies specific to at least HIF1A, SDF1, MMP9, JAG1, BCL2 and CD133 genes and (ii) pairs of primers, probes or antibodies specific to other markers of the tumor status, the angiogenic and lymphangiogenic status, the tumor microenvironment, and the migration activity, preferably selected from the group consisting of the genes listed in Tables 1 to 4, more preferably selected from the group consisting of ABL1, ALK, B7-H3 (CD276), BCL2, BRAF, CD133 (PROM1), CMET, CTLA4, EGFR, FGFR1, FGFR2, FGFR3, HER2, ERBB3, HIF1A, IGF1R, IntαV (ITGA5), JAG1, MEK 1 (MAP2K1), MEK 2 (MAP2K2), MMP9, PDGFRA, PDGFRB, PDL1 (CD274), RET, CXCL12 (SDF1), VEGFA, VEGFR2 (KDR), VEGFR3 (FLT4), CEACAM-1, CEACAM-5, PI3K alpha (PIK3CA), AKT1, AR (androgen receptor), HDAC1, HDAC2, C-RAF (RAF1), PD1, MDM2, CDK4, CDK6, IDO1, ABL2, FGFR4, HER4 (ERBB4), KIT, EZH2, IDH1, IDH2, VHL, mTOR, TRAIL-R1 (TNFRSF10A), TRAIL-R2 (TNFRSF10B), CD39 (ENTPD1), CREBBP, EP300, BRD4, GRB2, NOTCH 1, NOTCH 2, EPHA1, ANGPT1, Tie2 (TEK), RHOA, ROCK 1, ROCK 2, MMP2, CD34, DDR1, DDR2, KDM1A (LSD1), FOXP3, CD27, ICOS (CD278), IL4, IL13, HMGB1, FPR1, TGFb 1, TGFb 2 (LDS4), CD40, IL6, CTNNB1, MYC, WNT 2, WNT 3, CXCR4, CXCL10, TLR4, IL2RB, PDL2 (PDCD1LG2) and KIR2DL5A.

In a preferred embodiment, the kit comprises pairs of primers, probes or antibodies specific to at least 20, 30, 40, 50, 60, 70, 80 or 90 genes selected from the genes listed in Tables 1 to 4, preferably from the group consisting of ABL1, ALK, B7-H3 (CD276), BCL2, BRAF, CD133 (PROM1), CMET, CTLA4, EGFR, FGFR1, FGFR2, FGFR3, HER2, ERBB3, HIF1A, IGF1R, IntαV (ITGA5), JAG1, MEK 1 (MAP2K1), MEK 2 (MAP2K2), MMP9, PDGFRA, PDGFRB, PDL1 (CD274), RET, CXCL12 (SDF1), VEGFA, VEGFR2 (KDR), VEGFR3 (FLT4), CEACAM-1, CEACAM-5, PI3K alpha (PIK3CA), AKT1, AR (androgen receptor), HDAC1, HDAC2, C-RAF (RAF1), PD1, MDM2, CDK4, CDK6, IDO1, ABL2, FGFR4, HER4 (ERBB4), KIT, EZH2, IDH1, IDH2, VHL, mTOR, TRAIL-R1 (TNFRSF10A), TRAIL-R2 (TNFRSF10B), CD39 (ENTPD1), CREBBP, EP300, BRD4, GRB2, NOTCH 1, NOTCH 2, EPHA1, ANGPT1, Tie2 (TEK), RHOA, ROCK 1, ROCK 2, MMP2, CD34, DDR1, DDR2, KDM1A (LSD1), FOXP3, CD27, ICOS (CD278), IL4, IL13, HMGB1, FPR1, TGFb 1, TGFb 2 (LDS4), CD40, IL6, CTNNB1, MYC, WNT 2, WNT 3, CXCR4, CXCL10, TLR4, IL2RB, PDL2 (PDCD1LG2) and KIR2DL5A. In a more particular embodiment, the kit comprises pairs of primers, probes or antibodies specific to all of these genes.

In preferred embodiments, the kit comprises pairs of primers, probes or antibodies specific to less than 10 000, 9000, 8000, 7000, 6000, 5000, 4000, 3000, 2000, 1000 different genes, preferably less than 900, 800, 700, 600, 500, 400, 300, 200, 150, 120 or 100 genes, and more preferably less than 90, 80, 70, 60, 50, 40 or 30 genes.

Preferably, the kit comprises an array wherein probes specific of genes representative of the therapeutically targetable dominant signaling pathways as described above, are immobilized. Such probes may be easily designed by the skilled person.

Optionally, the kit may further comprise at least one pair of primer, probe or antibody specific to a housekeeping gene such as described above.

The kit may further comprise additional reagents such as buffer(s), enzyme(s) or nucleotides.

The present invention also relates to the use of a kit according to the invention and as disclosed above for (i) determining the therapeutically targetable dominant signaling pathways in a cancer sample, (ii) determining a treatment protocol for a subject having cancer, (iii) selecting a subject affected with a cancer for a therapy, (iv) determining whether a subject affected with a cancer is susceptible to benefit from a therapy, (v) predicting clinical outcome of a subject affected with a cancer, (vi) treating a patient affected with a cancer and/or (vii) predicting the sensitivity of a cancer to a therapy, according to the methods of the invention as disclosed above.

All embodiments disclosed for the methods of the invention are also contemplated in this aspect.

Further aspects and advantages of the present invention will be described in the following examples, which should be regarded as illustrative and not limiting.

Examples

Material and Methods

Tumor Samples Collection 21 patient glioblastoma biopsies were collected in the neurosurgery department at Strasbourg Hautepierre hospital (France). Only surgical remaining material not needed for tumor diagnosis or tissue collections were used. Patient consents are obtained and maintained systematically by the CRB (Centre de resources biologiques) and patient diagnoses are obtained from the Neuropathology department. Research samples are anonym for research. Biopsies were collected directly during the surgery, stored in DMEM (Dulbecco's Modified Eagle Medium High Glucose L0104-500) culture cell medium at 4° C. with 10% FBS (Fetal Bovine Serum; 10270-106), 100 U/mL of penicillin-100 µg/mL of Streptomycin and then immediately mechanically dissociated. A part of the biopsies is conserved at −80° C. The cell suspension is passed on a sieve made of 100 µm diameter pores, centrifuged at 800 rpm for 5 minutes. Supernatant is removed to add 20 mL of medium to suspend the pellet of cells, and centrifuged at 800 rpm for 5 minutes. This step is repeated 3 times in order to wash the cell suspension and to eliminate the red blood cells. Cells are then re-suspended in 5 mL of PBS 1x, 3 mL are kept for the RNA extraction and 2 mL for xenograft in mice.

Frozen fragments from 15 established patient-derived colorectal tumors xenografted and serially passaged subcutaneously in mice were provided by Oncodesign. (CR-IC-004M-P4/CR-IC-006M-P3/CR-IC-007M-P4/CR-IC-009M-P3/CR-IC-0013M-P3/CR-IC-0021M-P4/CR-IC-0025M-P3/CR-IC-0028M-P3/CR-IGR-002M-P4/CR-IGR-0023M-P3/CR-IGR-048M-P3/CR-IGR-052C-P4/CR-LRB-008M-P4/CR-LRB-009C-P4/CR-LRB-019C-P5). For each model, fragments from human primary tumor frozen in DMSO/SVF/RPMI 1640 medium (10/10/80) in liquid nitrogen were thawed at 37° C. for 5 minutes, rinsed twice in RPMI 1640 medium, and then were implanted on the right flank of 9 CB17 SCID mice.

We also collected RNA from 10 colon tumor stage I or IV (BIOSERVE; Z5ALYRSH/OQMNOR32/FC1AVRAA/4QDH8RIJ/RVBKJR34/EK21MRMMZ/R5NSMRQV/565HFAF2/65SVOR2E/38U4VRSY). The RNA samples were stored at −20° C.

We also collected RNA from 4 prostate adenocarcinomas (CLINISCIENCE; CR561921/CR559759/CR562458/CR560249), RNA from 5 PDX (patient-derived-xenograft provided by XENTECH, PAC120/HID28/HID28-CAS/HID110-CAS/HID115-CAS), and RNA from 6 stage II, III, or IV prostate tumor (BIOSERVE; GT55QRIQ; T523WRU4; 1XYXGRIR; VRS8ER21; PR3CURKH; MBUQ4RW3). All ARN samples were stored at −20° C.

RNA Extraction

For 5 PDX of prostate, tumor samples were at first crushed. Samples were placed in a tube (BERTIN TECHNOLOGIES; Precellys 24 Lysing Kit KT03961-1-403.2) with Tri Reagent® (MOLECULAR RESEARCH CENTER; RNA/DNA isolation reagent; TR118) and 5 beads (BERTIN TECHNOLOGIES; 2.8 mm Zirconium oxide beads 039661-1-102). Tubes were shacked with a Tissue Lyser (BERTIN TECHNOLOGIES; Precellys 24) at 6500 shake/min during 15s, centrifuged (EPPENDORF; Eppendorf Centrifuge 5417R) at 14 000 rpm during 14 min at 4° C. The aqueous phase is kept to extract the RNA.

Total RNA is extracted with Tri Reagent® (MOLECULAR RESEARCH CENTER; RNA/DNA isolation reagent;

TR118). 200 μL of chloroform (VWR Chemicals, 22706.292) is added; samples are vigorously mixed and incubated at room temperature for 15 minutes, and then centrifuged at 12000 g for 15 minutes at 4° C. Aqueous phase is transferred into a new tube and 500 μL of isopropanol (VWR Chemicals, 20839.366) is added, samples are mixed, and after 10 minutes at room temperature they are spin down at 12000 g for 8 minutes at 4° C. RNA pellet is mixed with 1 mL 75% ethanol and centrifuged at 7500 g for 5 minutes at 4° C. This step is repeated 3 times. Ethanol (VWR Chemicals, 20821.365) is removed, RNA pellet is air dried for 30 minutes to 1 hour, and then dissolved in ultra-pure water, and incubated at 50-60° C. for 10 minutes. After spin down, ARN concentration is measured with nanodrop (Thermo Scientific; Nanodrop 1000 Spectrophotometer). RNAs are stored at −20° until use.

Reverse Transcription

High Capacity cDNA Reverse Transcription Kit (APPLIED BIOSYSTEM; 4368814) is used to perform the reverse transcription of RNA. RNA are diluted at 2 μg/10 μL and incubate in an RNA MIX solution composed by 7.8 μL of ultra-pure water, 2 μL of 10X DNASE I reaction buffer, 0.2 μL of DNASE (10 U/μL) at room temperature for 15 minutes and then at 85° C. for 10 minutes. Samples are then cooled, mixed and spin. The half of the sample is incubated with 2 μL of RT buffer 10×, 0.8 μL DNTP mix, 2 μL random primers 10×, 4.2 μL of water and 1 μL of reverse transcriptase. Samples are incubated at 25° C. for 10 minutes, 37° C. for 2 hours, and 85° C. for 5 minutes. cDNA are then diluted 1/50 in ultra-pure water and conserved at −20° C.

RTqPCR

Expression levels of target genes composing the tumor signature is determined from RNA extracts freshly prepared from patient biopsies using customized microplate specially produced for this project by Applied Biosystems (APPLIED; Custom TaqMan Array Plates). 3 different batches were used for this project.

27 μL of cDNA are mixed with a TaqMan® master mix solution (APPLIED BIOSYSTEM; 4369016) to obtain a concentration between 1 and 100 ng per 20 μL reaction. TaqMAn plate is briefly centrifuged at 1000 rpm for 1 minute, the cover is then removed from the plate and 20 μL of cDNA and the master mix solution are dispensed in the appropriate wells of the plate. The plate is covered using a MicroAmp® Optical Adhesive Film (APPLIED BIOSYSTEM; 4311971) and briefly centrifuged (EPPENDORF Centrifuge 5417R) at 1000 rpm for 1 minute to bring the solution to the bottom of the wells. RTqPCR is performed with 7500 Real Time PCR System.

Normalization Process

Quantitative RT-qPCR provides the relative expression level of target genes compared with 2 housekeeping genes ribosomal 18S and GAPDH (ΔCt, ΔCt (cancer sample)=Ct (target gene in cancer sample)−mean Ct (housekeeping gene in cancer sample); ΔCt (reference tissue or cell type)=Ct (target gene in reference tissue or cell type−mean Ct (housekeeping gene in reference tissue or cell type)).

The normalization process is based on multiple rounds of comparisons of the expression level in the cancer sample and the expression level of the target genes in specific references for each tumor type (normal tissue, low grade or begin tumor tissue(s) and tissue cellular subtype(s)).

All the intermediate relative expression levels are calculated ($2^{-\Delta\Delta Ct}$, $2^{-\Delta\Delta Ct}=2^{-\Delta Ct}$ (cancer sample)$-2^{-\Delta Ct}$ (reference tissue or cell type)) and added (Addition=$2^{-\Delta\Delta Ct}$ (reference tissue or cell type 1)+$2^{-\Delta\Delta Ct}$ (reference tissue or cell type 2)+ . . . +$2^{-\Delta\Delta Ct}$ (reference tissue or cell type n)).

After ranking the score for each target, a Normalized score is determined given 1000 points to the highest level.

References for the glioblastoma are total RNA from normal brain (AGILENT TECHNOLOGIES; 540005), astrocytoma (CLINISCIENCES; CR562205), astrocyte (SCIENCELL; 1805), and oligodendrocytes (BIOCHAIN; R1234045-10).

TABLE 6

Composition of three different sets of genes (batches) used in this project

| Batch 1 | Batch 2 | Batch 3 |
|---|---|---|
| 18S Hs99999901_s1 | 18S Hs99999901_s1 | 18S Hs99999901_s1 |
| GAPDH Hs99999905_m1 | GAPDH Hs99999905_m1 | GAPDH Hs99999905_m1 |
| CXCL12 Hs00171022_m1 | CXCL12 Hs00171022_m1 | CXCL12 Hs00171022_m1 |
| BCL2 Hs00153350_m1 | BCL2 Hs00153350_m1 | BCL2 Hs00153350_m1 |
| PROM1 Hs01009250_m1 | PROM1 Hs01009250_m1 | PROM1 Hs01009250_m1 |
| HIF1A Hs00936368_m1 | HIF1A Hs00936368_m1 | HIF1A Hs00936368_m1 |
| CD34 Hs02576480_m1 | | |
| | PARG Hs00608256_m1 | PARG Hs00608256_m1 |
| VEGFA Hs00173626_m1 | VEGFA Hs00173626_m1 | VEGFA Hs00173626_m1 |
| FLT1 Hs01052936_m1 | FLT1 Hs01052936_m1 | FLT1 Hs01052936_m1 |
| KDR Hs00911700_m1 | KDR Hs00911700_m1 | KDR Hs00911700_m1 |
| JAG1 Hs001064982_m1 | JAG1 Hs001064982_m1 | JAG1 Hs001064982_m1 |
| MMP9 Hs00957562_m1 | MMP9 Hs00957562_m1 | MMP9 Hs00957562_m1 |
| MMP2 Hs00234422_m1 | MMP2 Hs00234422_m1 | MMP2 Hs00234422_m1 |
| TNC Hs001115665_m1 | TNC Hs001115665_m1 | TNC Hs001115665_m1 |
| TNW Hs00295597_m1 | | |
| ITGB1 Hs00236976_m1 | ITGB1 Hs00236976_m1 | ITGB1 Hs00236976_m1 |
| CMET Hs01565583_m1 | CMET Hs01565583_m1 | CMET Hs01565583_m1 |
| FGF2 Hs0026645_m1 | | FGF2 Hs0026645_m1 |
| PDGFRA Hs00183486 | PDGFRA Hs00183486 | PDGFRA Hs00183486 |
| | HER2 Hs01001580_m1 | HER2 Hs01001580_m1 |
| | EGFR Hs01076078_m1 | EGFR Hs01076078_m1 |
| SEMA3A Hs00173810_m1 | SEMA3A Hs00173810_m1 | SEMA3A Hs00173810_m1 |
| NRP1 Hs00826129_m1 | NRP1 Hs00826129_m1 | NRP1 Hs00826129_m1 |
| NRP2 Hs00187290_m1 | NRP2 Hs00187290_m1 | NRP2 Hs00187290_m1 |
| PLXNA1 Hs00413698_m1 | PLEXA1 Hs00413698_m1 | PLEXA1 Hs00413698_m1 |
| PLXNB1 Hs00963507_m1 | | |

References for the colon tumor are total RNA from human colonic smooth muscle cell (CLINISCIENCES; 2945-SC), human colonic epithelial cells (CLINISCIENCES; 2955-SC), and Polyps.

References for the prostate tumor are total RNA from prostate epithelial cell (CLINISCIENCES; 4405-SC), prostate micro-vascular endothelial cells (CLINISCIENCES; 4415-SC), prostate fibroblast cells (CLINISCIENCES; 4435-SC), prostate within normal limits (CLINISCIENCES; CR559759), and glandular hyperplasia of prostate (CLINISCIENCES; CR560153).

The intermediate relative expression level $2^{-\Delta\Delta Ct}$ obtained with the different reference samples are added before ranking genes in a decreasing order to calculate the scores. The gene with highest score is set to an arbitrary unit of 1000 points, and the other genes are normalized with this value. Each gene receives a score between [0; 1000] (FIG. 1).

In Vivo Experiments: Glioblastoma Model

All procedures using animals were submitted to the Animal Care and Use Committee of and received approval.

Immunocompromised mice were anesthetized with isoflurane 3% (BAXTER), under 0.5 L O2, and received a subcutaneous injection of ketofen 1% 1.5 mL/Kg (MERIAL). The scalp was incised and 100 000 cells of the dissociated glioblastoma biopsy were engrafted with a 2 µL Hamilton syringe (HARVARD APPARATUS; HAM-88400) mounted on a stereotaxic set up (HARVARD APPARATUS) at the following coordinates from the bregma x: −2 mm; y: +1 mm; z: −3.5 mm at a speed of 0.66 µl/min, 5 minutes after the syringe introduction. After injection, the syringe was kept in place for 5 minutes, and then raised for 1 mm per minute. The scalp was sutured with 7.5 mm Michel stainless steel wound clips (A75, PERFECT). Animals were allowed to recover under a heat lamp several minutes before they were returned to their cage.

After 52 days of tumor development, mice were randomized in 4 groups of treatment. First group was treated with Temozolomide 40 mg/kg (n=9) i.v during 5 consecutive days, second one was treated with SB-3CT 25 mg/kg (n=9) p.o during 10 days interrupted by 2 days of wash-out after 5 days, a third group was treated with Cediranib 6 mg/kg (n=10) p.o during 10 days interrupted by 2 days of wash-out after 5 days, a last one group was treated with Erlotinib 50 mg/kg (n=9) p.o 1 time per week during 3 weeks. The administration volume was 100 µL. On the day of termination (21 days after the first treatment), all mice are sacrificed by cervical dislocation, brains are removed (38 total samples), and included in cryo-embedding media OCT© and stored at −80° C.

Brains were cut in 20 µm sections with a cryostat (LEICA CM 3050S), mounted on blade (Superfrost Super Plus), and stored at −20° C. In order to visualize the tumor, brain sections were thawed in distilled water and Stained with 2% diluted Giemsa's staining (SUBRA; RAL diagnostic 320310-1000) in distilled water at 37° C. for 2 hours. Sections were then rinsed in distilled water, incubated in 0.5% aqueous acetic acid (SIGMA; 33209-12) for 15 seconds, rapidly dehydrated in 70, 95 and 100% ETOH baths, in toluene (VWR Chemicals; 28676.297) and mounted under a cover slips (KNITTEL GLASS). Tumor volume was calculated by the addition of every partial volume: $[V_{total}=\Sigma partial \ volumes=\Sigma d_1 \times (S1+S2)/2+d_2 \times (S2+S3)/2+ \ldots +d_n \times (S_n+S_{n+1})]$. All the surfaces were obtained by surrounding the tumor limits on every brain slices with ZEN software.

In Vivo Experiments: Colorectal Tumor Model

All procedures using animals were submitted to the Animal Care and Use Committee of Oncodesign (Oncomet) agreed by French authorities.

The predictive value of the calculated score was tested in a colorectal cancer tumor animal model. Small tumor fragments (CR-IC-004M-P4/CR-IC-006M-P3/CR-IC-007M-P4/CR-IC-009M-P3/CR-IC-0013M-P3/CR-IC-0021M-P4/CR-IC-0025M-P3/CR-IC-0028M-P3/CR-IGR-002M-P4/CR-IGR-0023M-P3/CR-IGR-048M-P3/CR-IGR-052C-P4/CR-LRB-008M-P4/CR-LRB-009C-P4/CR-LRB-019C-P5) were subcutaneously implanted in the right flank of CB17 SCID mice. The treatment started when tumors reached a mean volume of 200-300 mm³. Animals were randomized according to their individual tumor volume into 2 groups using Vivo Manager® software (Biosystemes, Couternon, France). A statistical test (analysis of variance) was performed to test for homogeneity between groups. The first group was treated with Cetuximab 12.5 mg/kg (n=10) i.p 1 times per week during 3 weeks, the second with the vehicle of Cetuximab 0.9% NaCl. The tumor volume was calculated by $[(a \times b^2) \ 2]$, where a is the largest tumor diameter and b the perpendicular tumor diameter measured with a caliper.

The predictive value of the signature was tested in one PDX models (ONCODESIGN; CR-IC-028M) chosen according to the obtained signatures and previous results having demonstrated that these two models were not responsive to Cetuximab. Small tumor fragments were subcutaneously implanted in the right flank of 9 CB17 SCID mice. When tumor size reached 500-700 mm³, tumors were surgically excised and small tumor fragments were subcutaneously implanted in the right flank of 52 recipient SWISS Nude mice.

The treatment started when tumors reached a mean volume of 200-300 mm³. 40 animals out were randomized according to their individual tumor volume into 4 groups each of 10 animals using Vivo Manager® software (Biosystemes, Couternon, France). A statistical test (analysis of variance) was performed to test for homogeneity between groups.

The first group of the model CR-IC-028M was treated with Cetuximab 12.5 mg/kg (n=10) i.p 1 times per week during 3 weeks, the second with Trastuzumab 1 mg/kg (n=10) i.p twice weekly during 3 weeks, a third group was treated with Cediranib 6 mg/kg (n=10) p.o during 10 days interrupted by 2 days of wash-out after 5 days. The last one, the control group received a mix of the vehicle of Cetuximab and Cediranib. The administration volume for the two models was 10 mL/kg (200 µL/mouse of 20 g) adjusted to the most recent individual body weight of mice.

The tumor volume was calculated by $[(a \times b^2) \ 2]$, where a is the largest tumor diameter and b the perpendicular tumor diameter measured with a caliper every 3 days.

On the day of termination (31 days after the first treatment), mice were sacrificed (40 total samples) by gas anesthesia over-dosage (Isoflurane) followed by cervical dislocation or exsanguination and tumor were collected from all mice.

In Vivo Experiments: Prostate Tumor Model

The authorization to use animals in the CERFE facilities was obtained by The Direction des Services Vétérinaires, Ministère de l'Agriculture et de la Pêche, France. The animal care and housing are in accordance with French regulatory legislation concerning the protection of laboratory animals. All experiments are performed in accordance with French legislation concerning the protection of laboratory animals and in accordance with a currently valid license for experiments on vertebrate animals, issued by the French Ministry for Agriculture and Fisheries.

One PDX model (XENTECH; HID-28, a hormone refractory prostate cancer (HRPC) variant) was chosen according to the obtained signature and previous results having demonstrated that this model is responsive to Docetaxel. Small tumor fragments are subcutaneously implanted in the flank of athymic nude mice. When tumor size reached 1000 to 2000 mm$^3$, tumors are surgically excised and small tumor fragments (approximately 40 mm$^3$) are implanted in the subcutaneous tissue of the interscapular region of 82 nude mice. 36 mice with established growing tumors and tumor volume ranging 60 to 200 mm$^3$ are included in the study and randomized according to their individual tumor volume into 4 groups of 9 mice. Tumor signature is verified during the amplification and also after engraftment.

The first group is treated with Erlotinib 50 mg/kg (n=9) p.o 1 time per week during 3 weeks, the second is treated with Cediranib 6 mg/kg (n=9) p.o during 3 cycles of 5 days interrupted by 2 days of wash-out, the third group with a mix of the vehicle of Erlotinib and Cediranib (sodium carboxymethylcellulose 0.5%, captisol 15%, DMSO 1% and methylcellulose 0.5%), and the last group is treated with Docetaxel 20 mg/kg (n=9) i.p during 2 cycles of 1 injection every 3 weeks.

Tumor volume is evaluated biweekly by measuring tumor diameters, with a caliper. The formula TV (mm$^3$)=[length (mm)×width (mm)$^2$]/2 will be used, where the length and the width are the longest and the shortest diameters of the tumor, respectively.

On the day of termination (28 days after the first treatment), mice are sacrificed by cervical dislocation, tumor are collected from all mice (36 tumor samples totally) and serum from 5 mice per group is collected (20 serum samples totally).

Drugs and Formulation

Temodal (Selleckchem) is solubilized in DMSO 20%, SB-3CT (Selleckchem) is prepared in DMSO 30%. Cediranib (Selleckchem) is solubilized in methylcellulose 0.5%. Erlotinib (Selleckchem) is solubilized in sodium carboxymethylcellulose 0.5%, captisol 15% (Cydex pharmaceuticals), DMSO 1%. All drugs are diluted in PBS 1X. Cetuximab is solubilized in NaCl 0.9% (Aguettant, Lyon, France). Trastuzumab is prepared in NaCl 0.9% (75 mg/mL). The stock solution is kept at +4° C. for all the duration of the study. Each day of administration to mice, the stock solution is diluted in NaCl 0.9%. Docetaxel is prepared in Ethanol 12% and NaCl 0.9%.

Results

Determination of the Personal Signatures:

The present invention is intended to provide clinicians with a patient personal molecular signature allowing the identification of the best treatment of a solid cancer. The proof of concept is illustrated here for three representative solid tumors comprising brain glioblastoma (GBM), colon cancer (CC) and prostate cancer (PC). The personal signatures are obtained after different rounds of normalization comparing the expression of target genes in the biopsy with different reference samples as detailed above. The final signature is showing a predictive ranking of drug efficacy resulting from the different comparisons for each target. As illustrated in FIG. 1 for a GBM biopsy, the score is obtained by adding the values ($2^{-\Delta\Delta Ct}$) obtained when normalizing data to the brain (intermediate relative expression 1), to astrocytes (intermediate relative expression 2), to oligodendrocytes (intermediate relative expression 3) and to low grade astrocytoma (intermediate relative expression 4). The obtained values are then converted into arbitrary units set at 1000 points for the highest score. Data are finally represented in a radar mode showing the log of the Normalized scores (FIG. 1).

The best therapeutic target is considered as the target exhibiting the highest score post normalization. A restricted signature can then be extracted from this list. This restricted list is defined by only conserving target genes for which a drug is available. In this case, the target gene with the highest score is set to 1000 points before representing data in a radar mode showing the log of the scores of best available therapeutic tools/drug (FIG. 2).

Figure 3A:
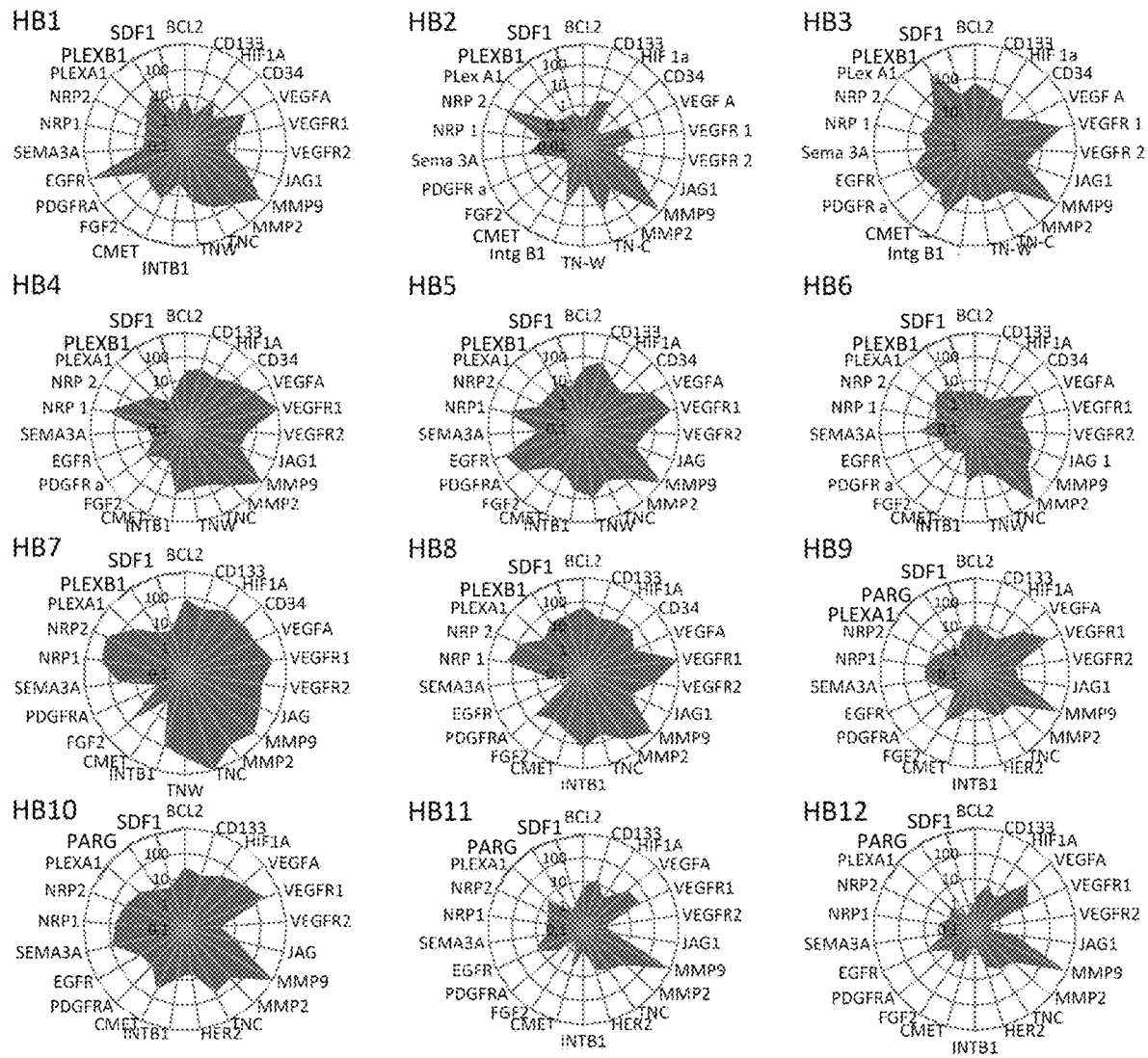
FIGS. 3A and 3B: Radar mode of the personal signatures of 21 patients with glioblastome. Patients HB1 to HB 12 (FIG. 3A) and HB13 to HB21 (FIG. 3B).
Figure 3B:
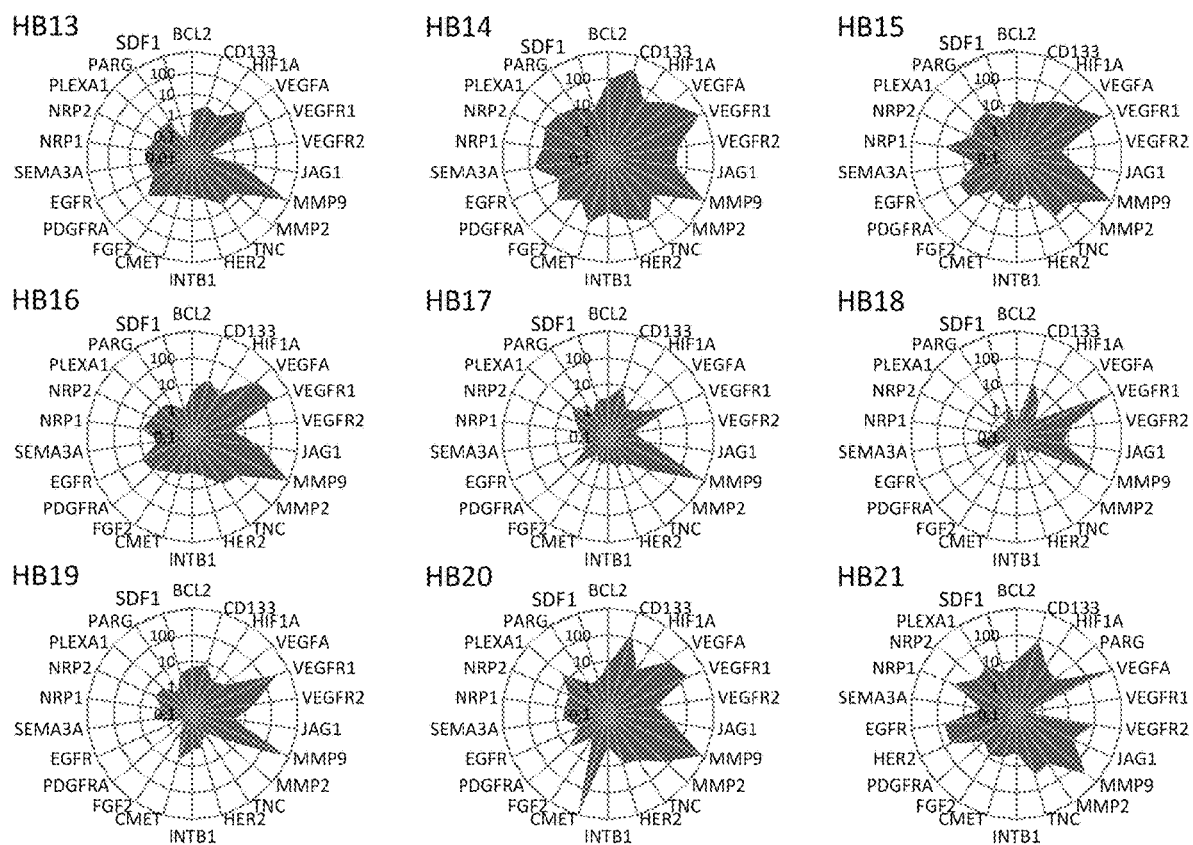

As seen in FIG. 3 for 21 patients with GBM, all signatures were different from each other. In some cases, the signatures shared similarities in term of the genes with the highest score but always had genes with specific scores, different from all other patients (FIG. 3A, 3B).

Figure 4:
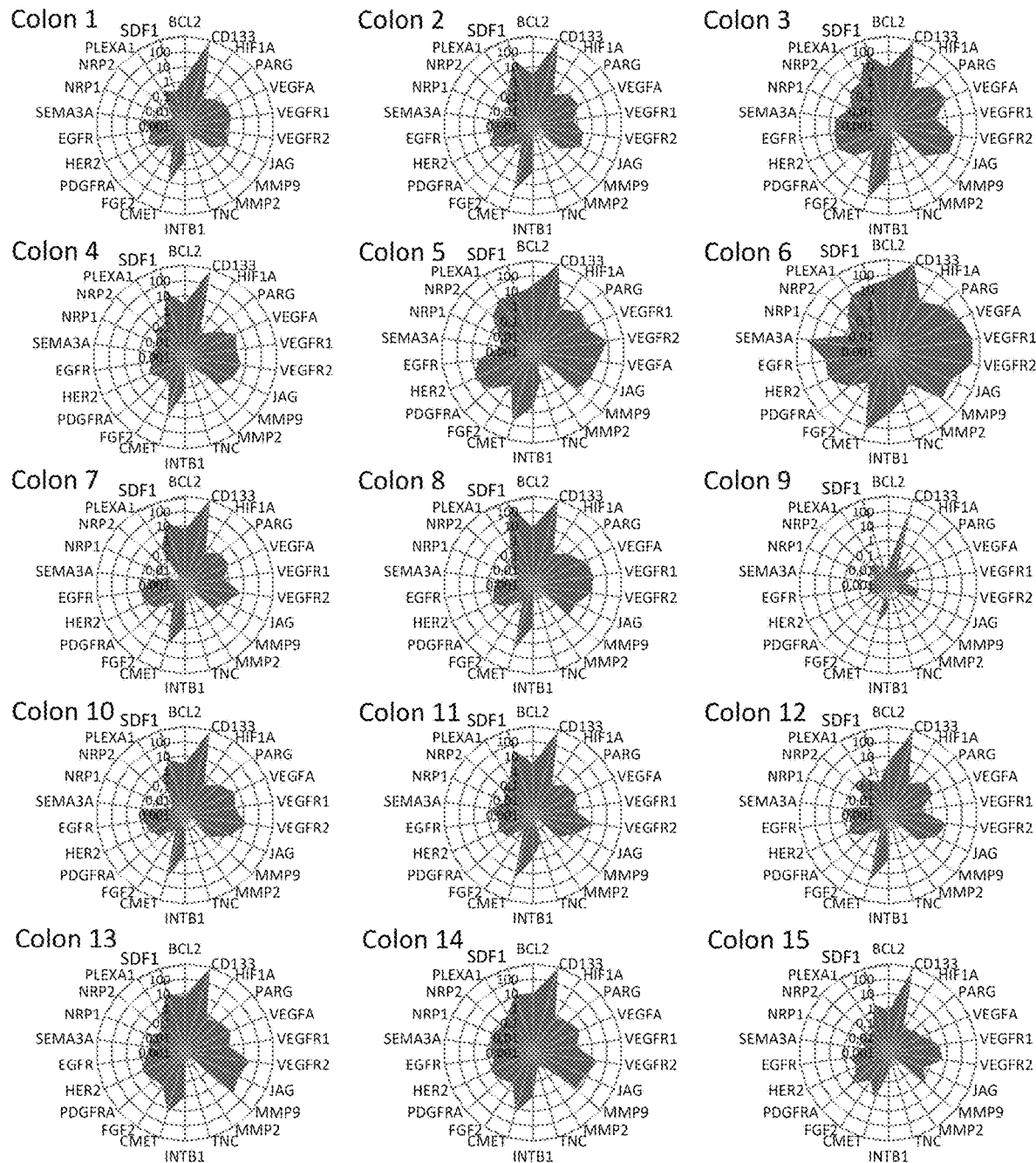
FIG. 4: Radar mode of the personal signatures of 15 patients with colorectal cancer.
Figure 5:
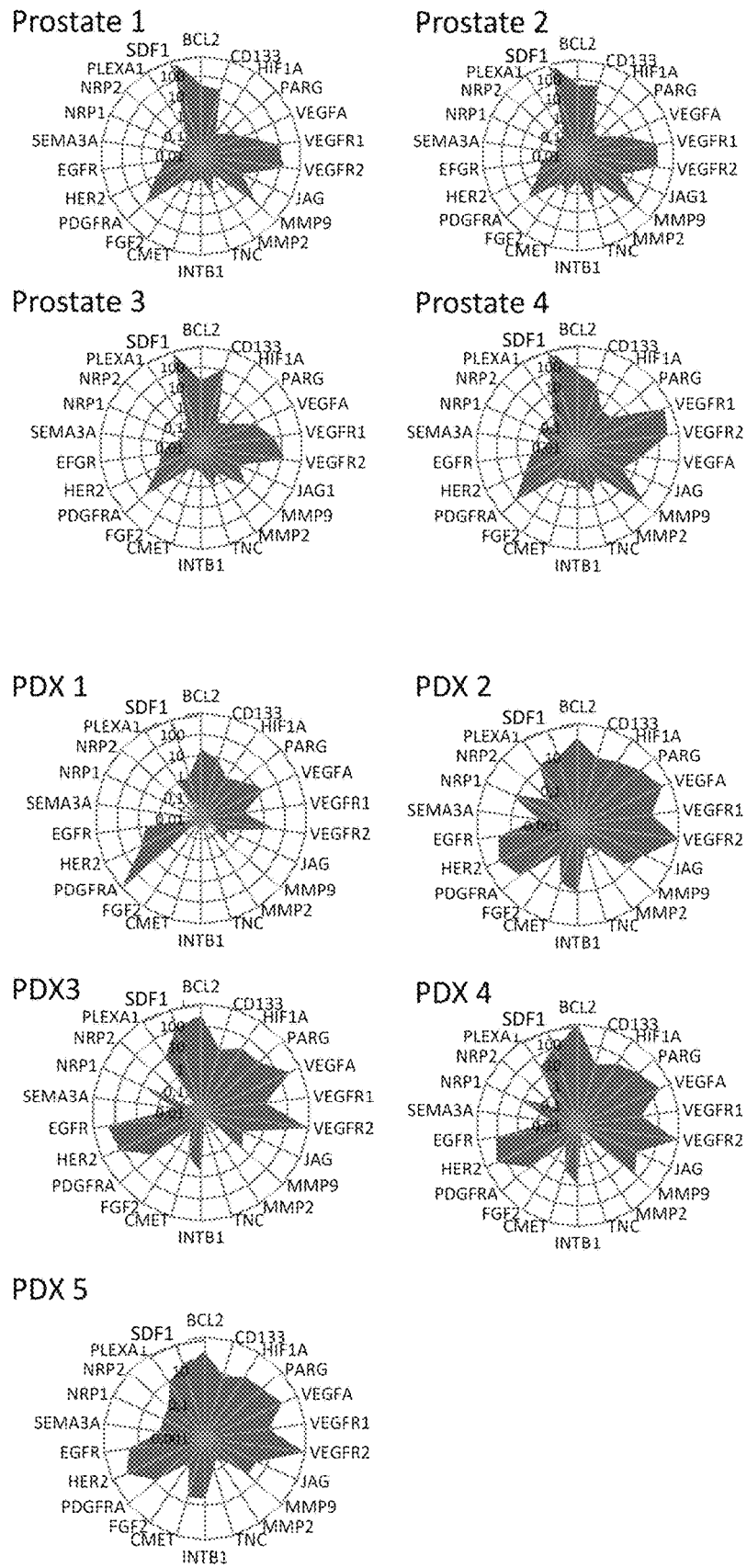
FIG. 5: Radar mode of the personal signatures of 15 patients with prostate cancer.
Figure 6A:
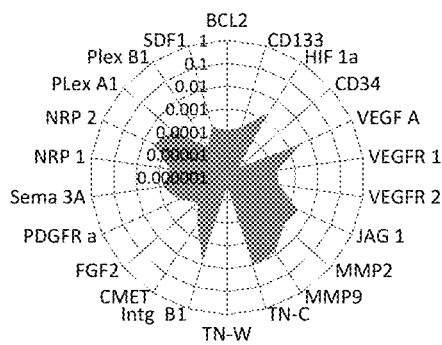
FIGS. 6A-6E: Personal signature obtained from a GBM biopsy (HB2). Radar mode of raw data (FIG. 6A), with one step of normalization (FIG. 6B), with two steps of normalization (FIG. 6C), with three steps of normalization (FIG. 6D), and with four steps of normalization (FIG. 6E).
Figure 6B:
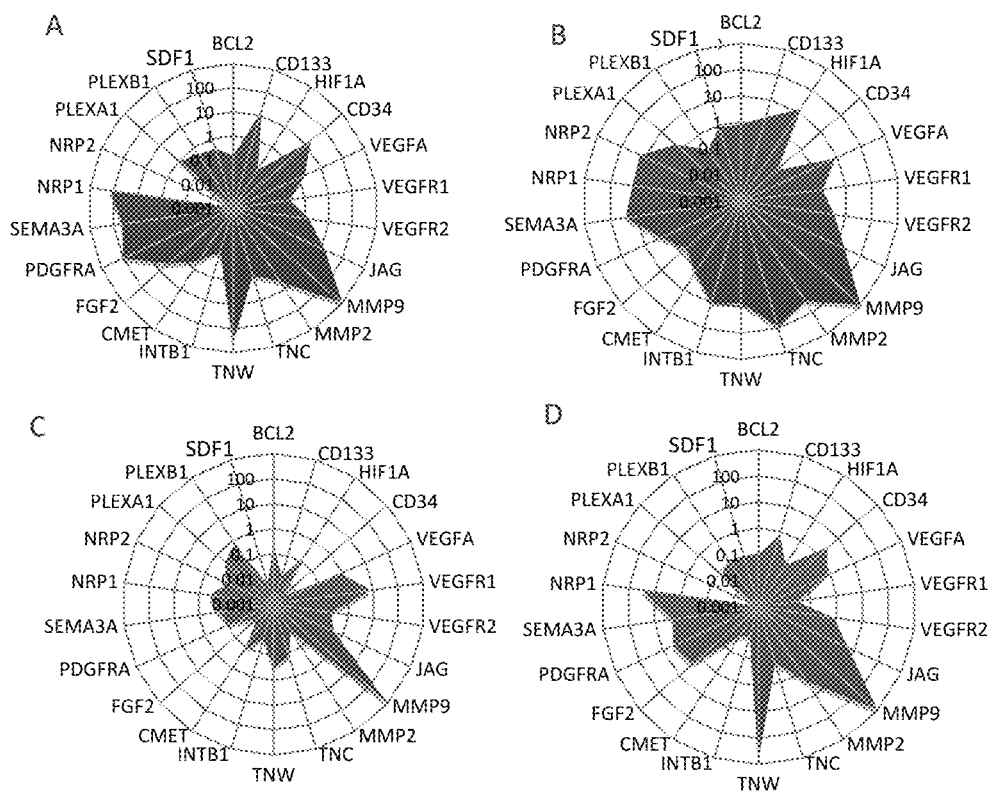
Figure 6C:
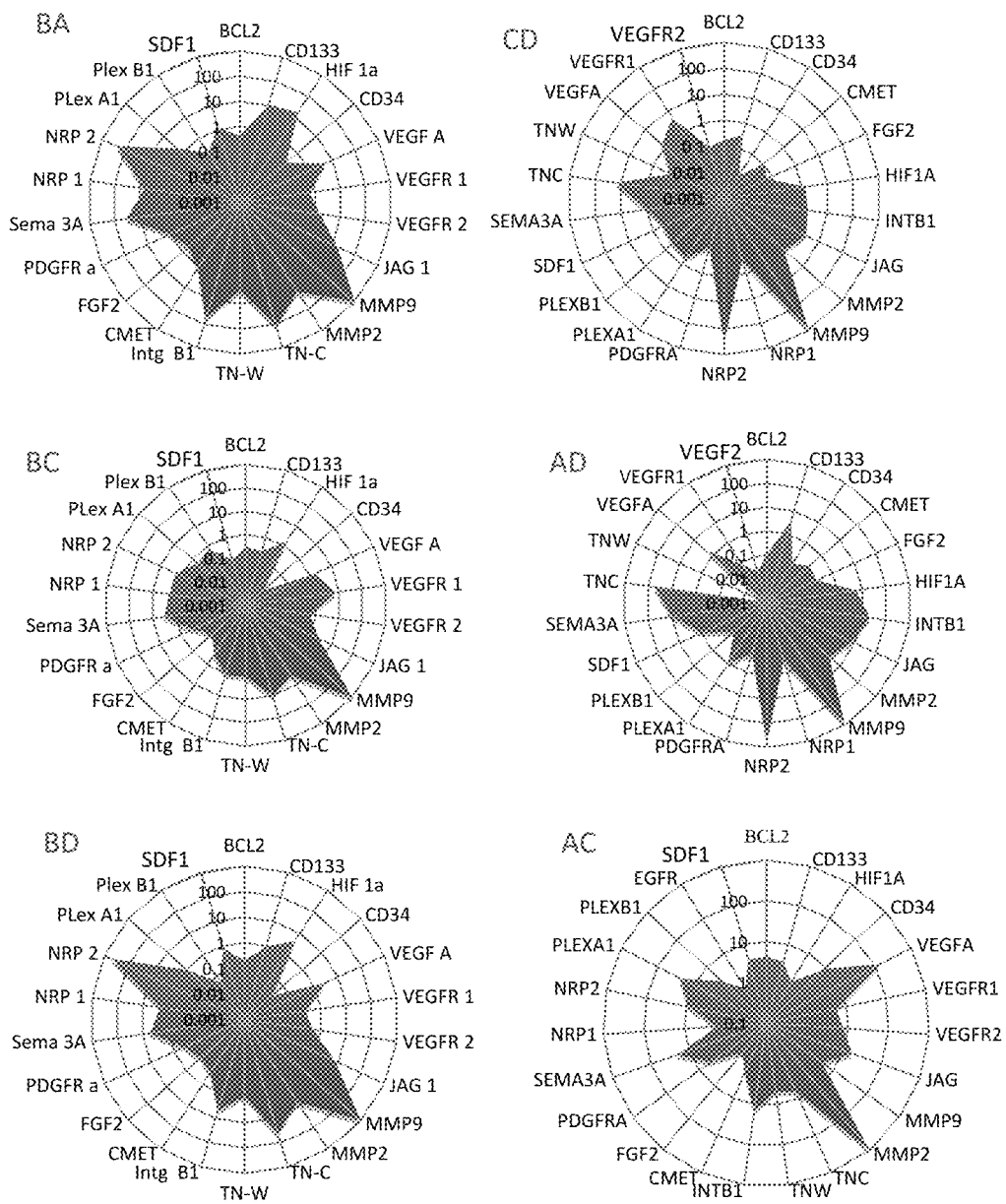
Figure 6D:
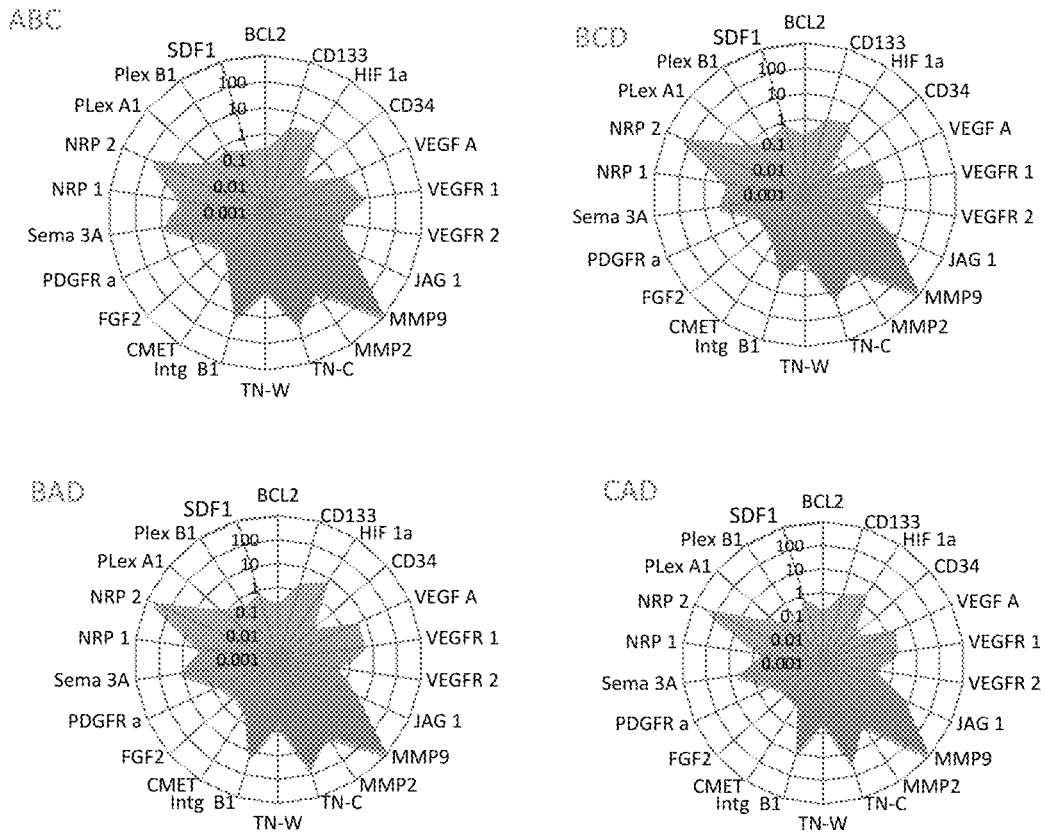
Figure 6E:
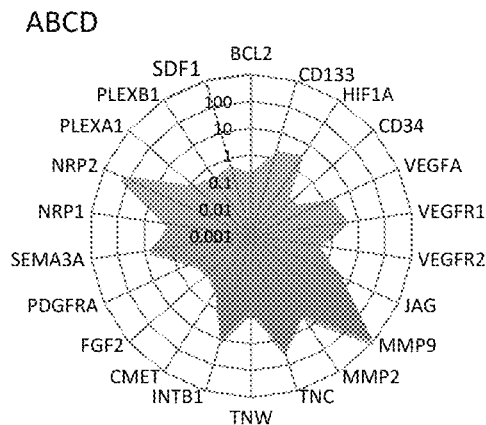

A similar study was conducted on 15 patients with CC (FIG. 4). In this case, RNA samples were collected from the patient-derived xenografted biopsies. For this tumor type, scores were obtained by adding the values ($2^{-\Delta\Delta Ct}$) obtained when normalizing data to the normal colon (intermediate relative expression 1), to human epithelial colonic cells (intermediate relative expression 2), to microvascular colonic cells (intermediate relative expression 3) and to low grade colon tumors (intermediate relative expression 4). FIG. 4 illustrates the different signatures. While presenting less variability, each signature showed again highly specific and individual expression level of each target genes leading to individual signatures, specific for each patient. Hence, we performed the analysis on 9 patients with PC (4 biopsies and 5 patient-derived xenografted biopsies). For this tumor type, scores were obtained by adding the values ($2^{-\Delta\Delta Ct}$) obtained when normalizing data to the normal prostate (intermediate relative expression 1), to epithelial cells (intermediate relative expression 2), to prostate microvascular endothelial cells (intermediate relative expression 3), to prostate fibroblasts (Intermediate relative expression 4) and to low grade prostate cancer (intermediate relative expression 5). Here again, each patient exhibited a personal signature eventually sharing common traits for some target genes (FIG. 5).

Figure 7C:
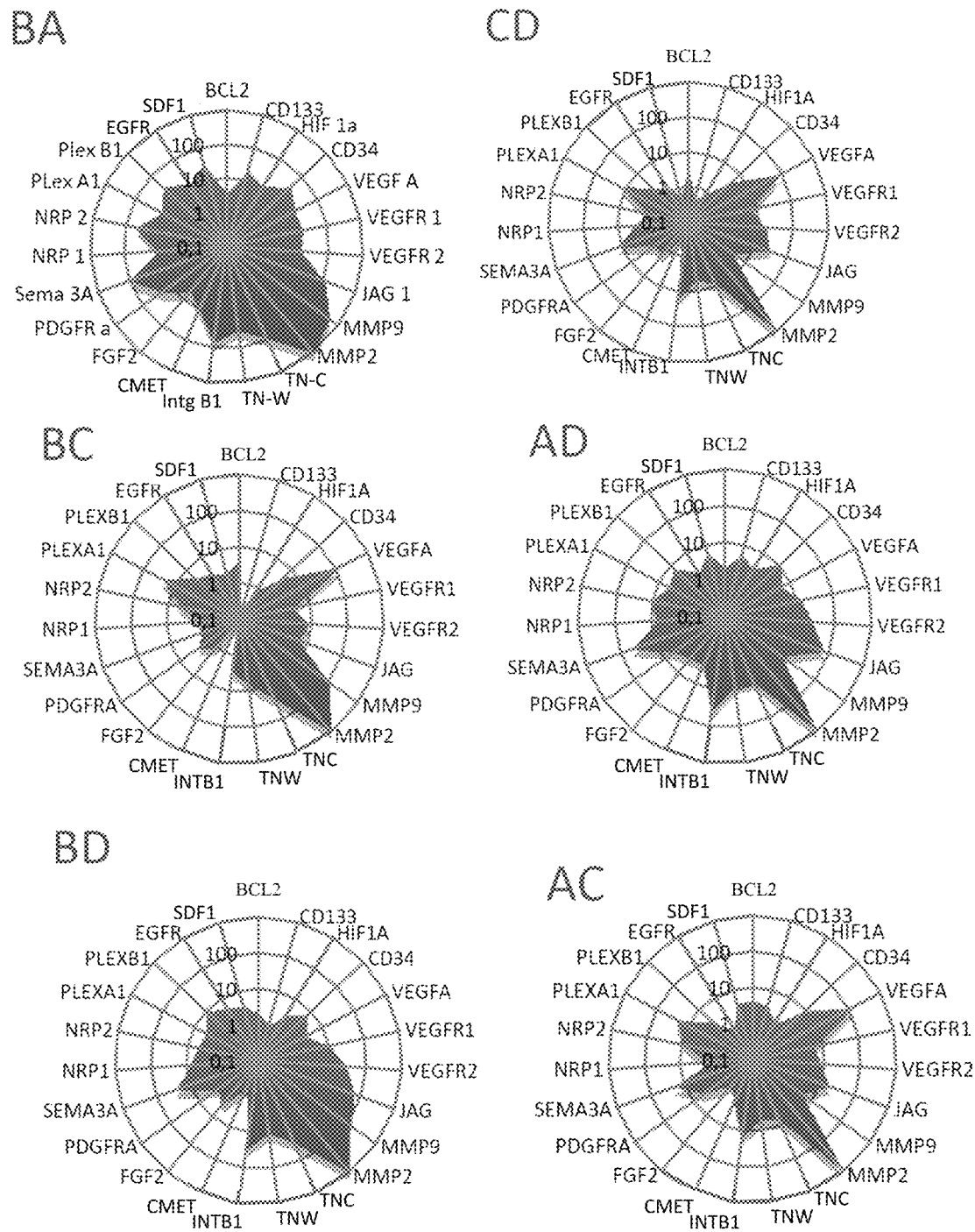
Figure 7D:
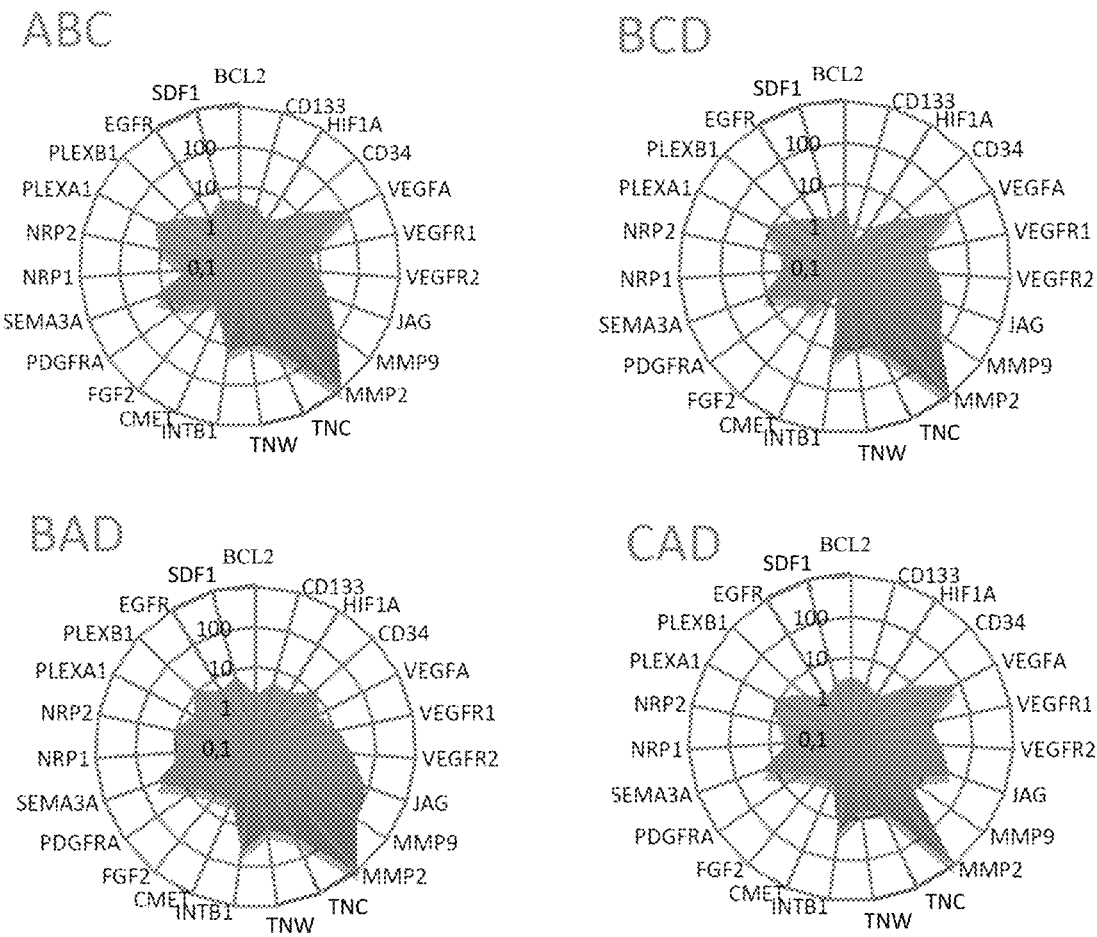
Figure 7E:
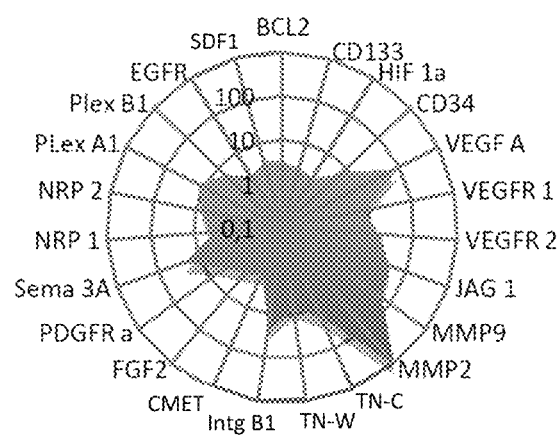
Figure 8A:
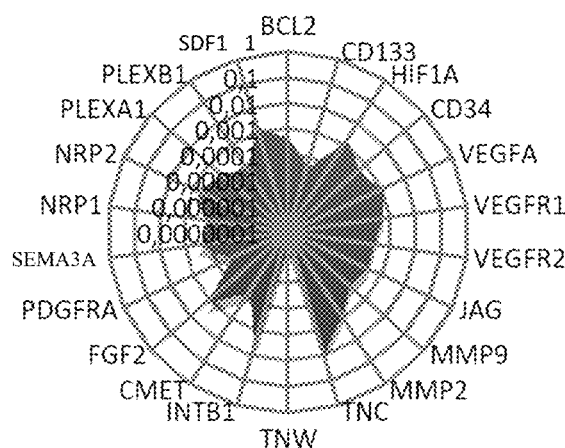
FIGS. 8A-8E: Personal signature obtained from a GBM biopsy (HB7). Radar mode of raw data (FIG. 8A), with one step of normalization (FIG. 8B), with two steps of normalization (FIG. 8C), with three steps of normalization (FIG. 8D), and with four steps of normalization (FIG. 8E).
Figure 8B:
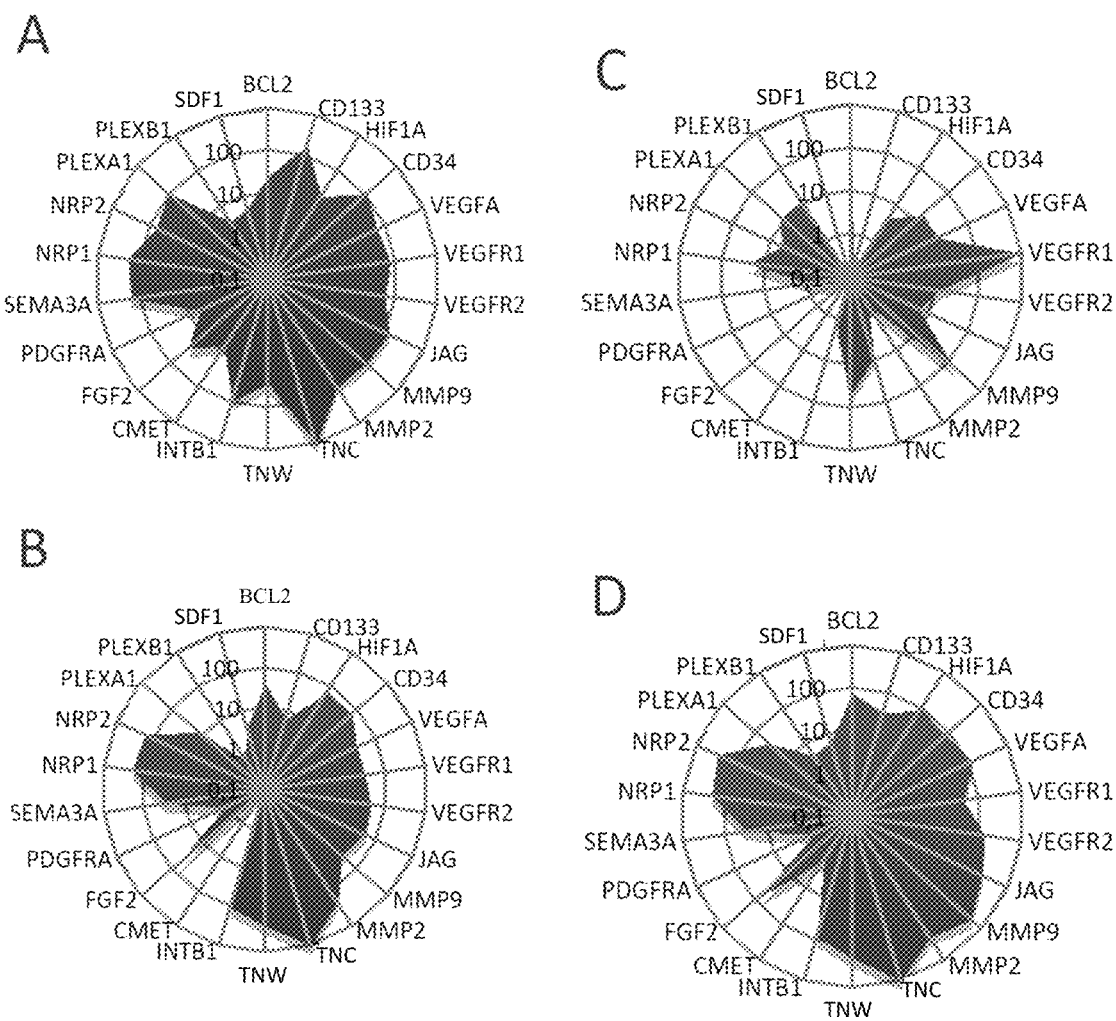
Figure 8C:
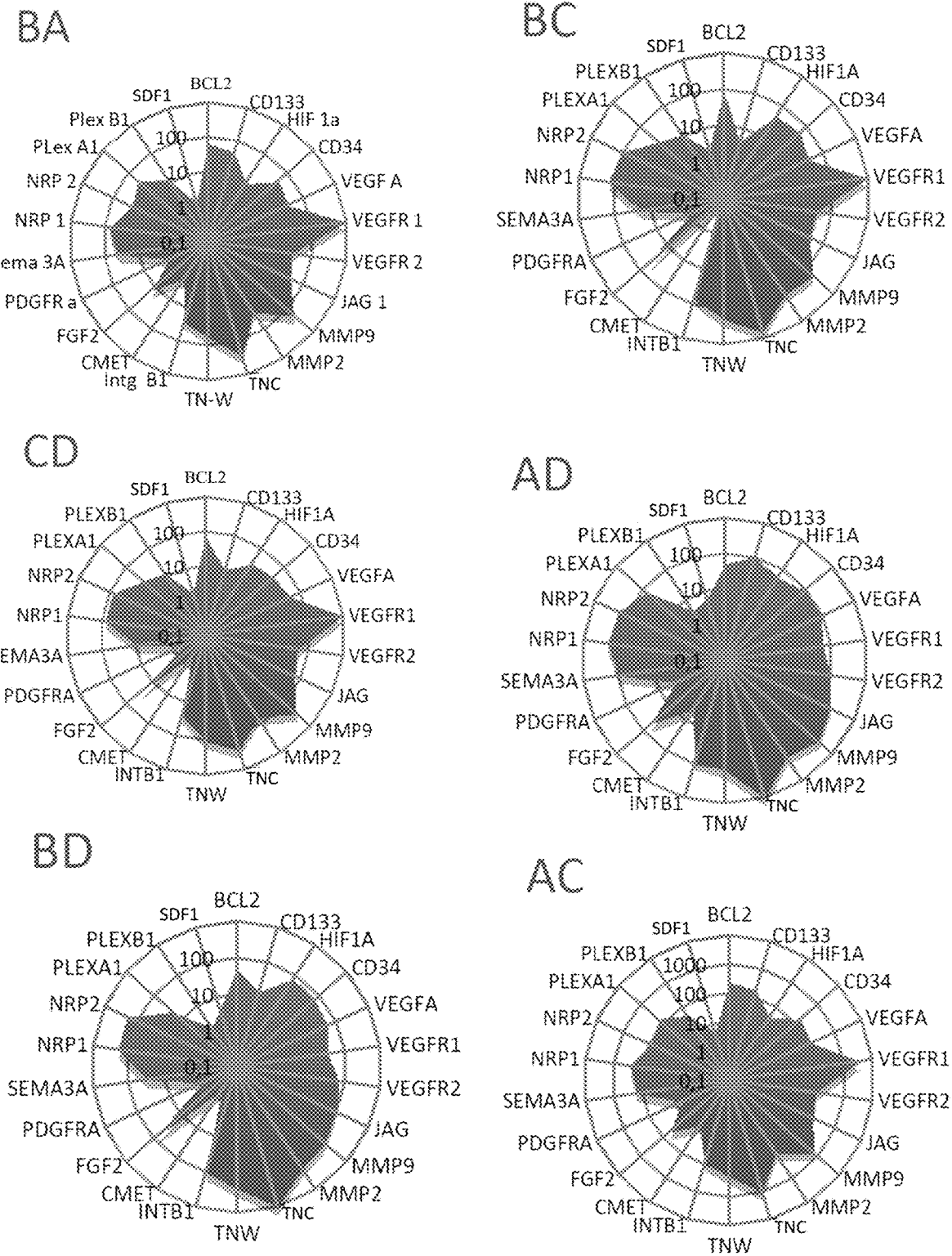
Figure 8D:
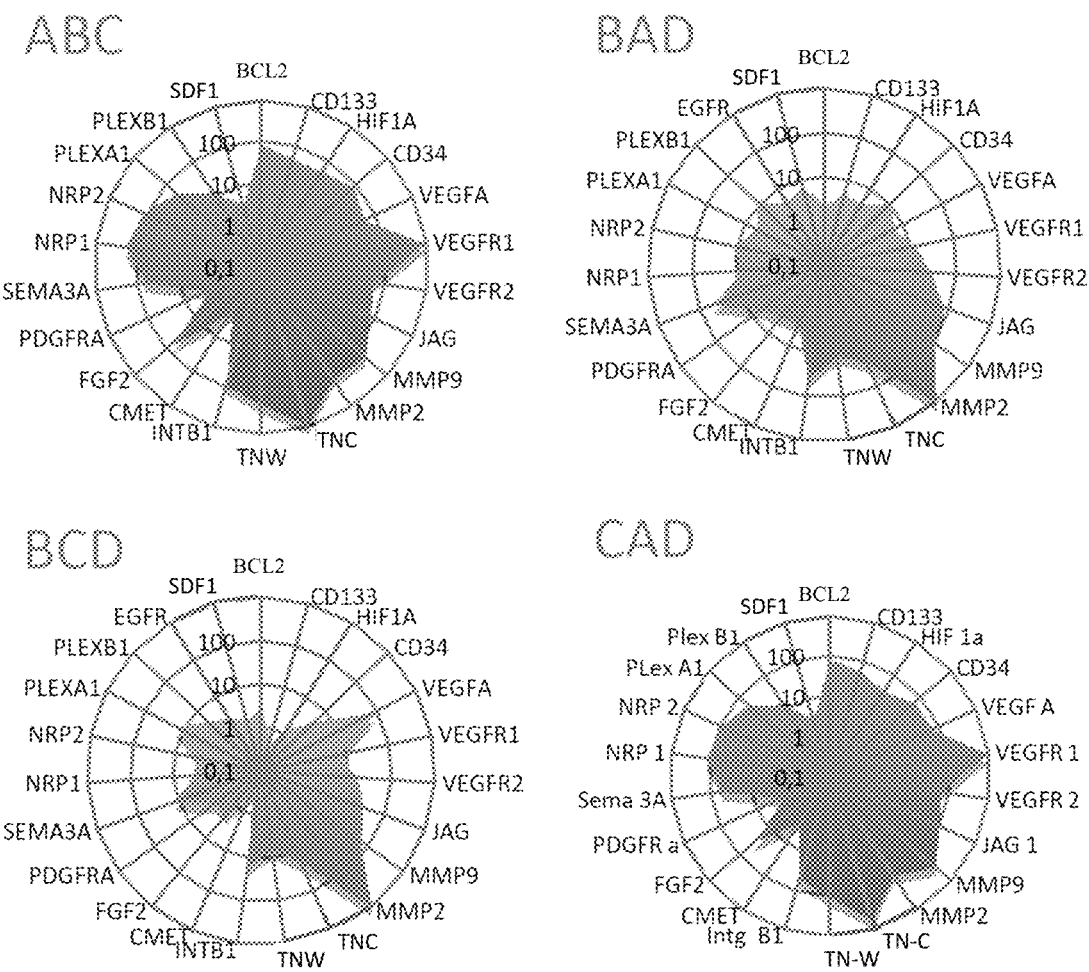
Figure 8E:
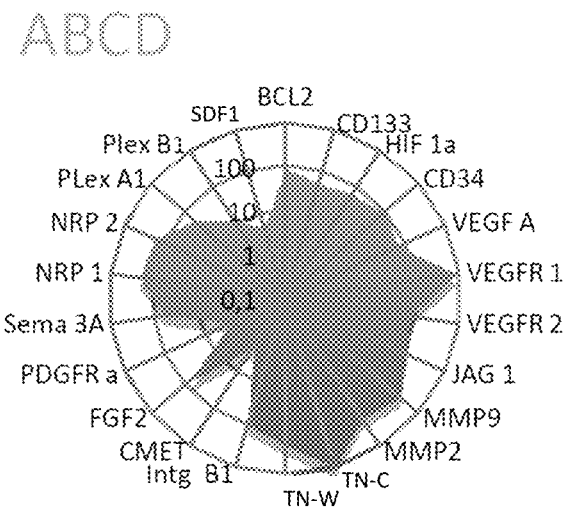
Figure 9A:
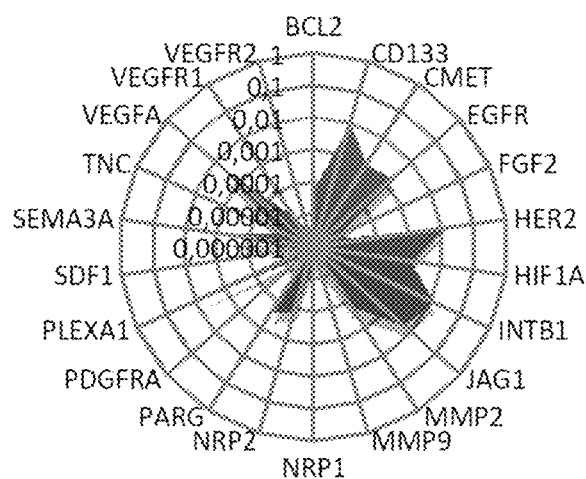
Figure 9B:
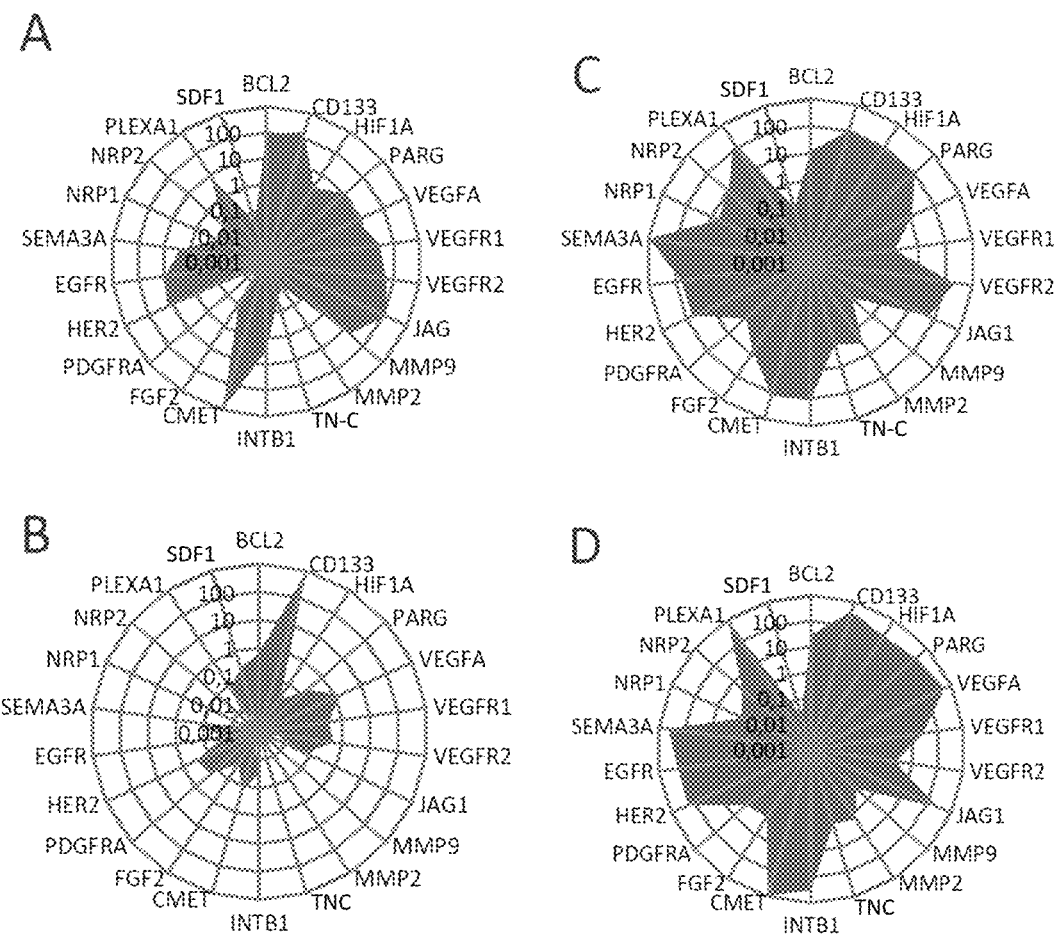
Figure 9C:
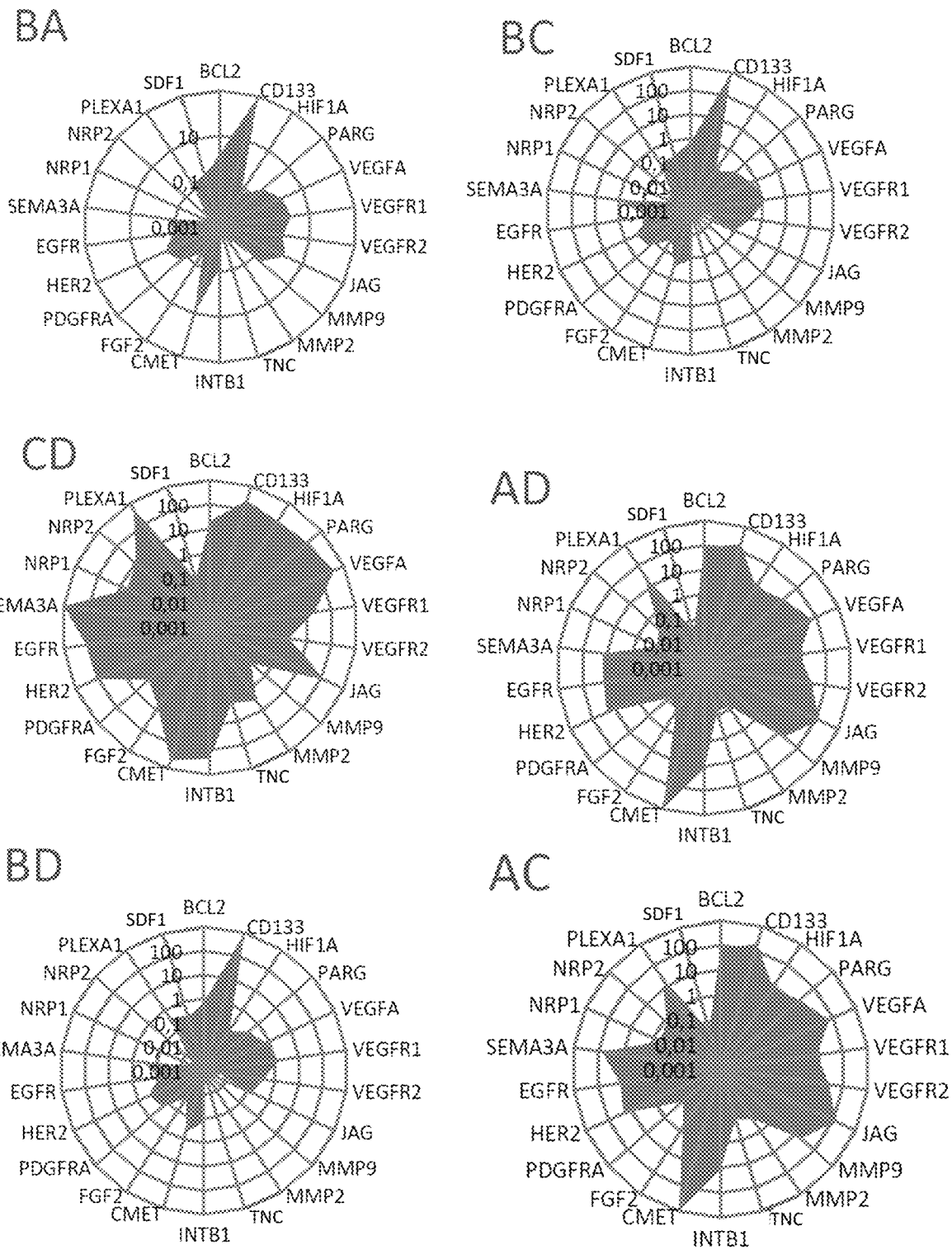
Figure 10A:
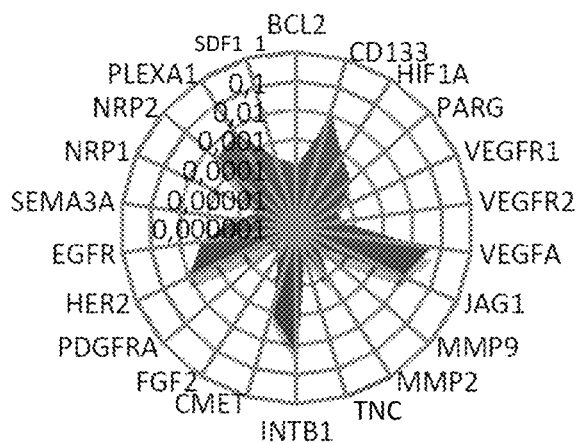
Figure 10B:
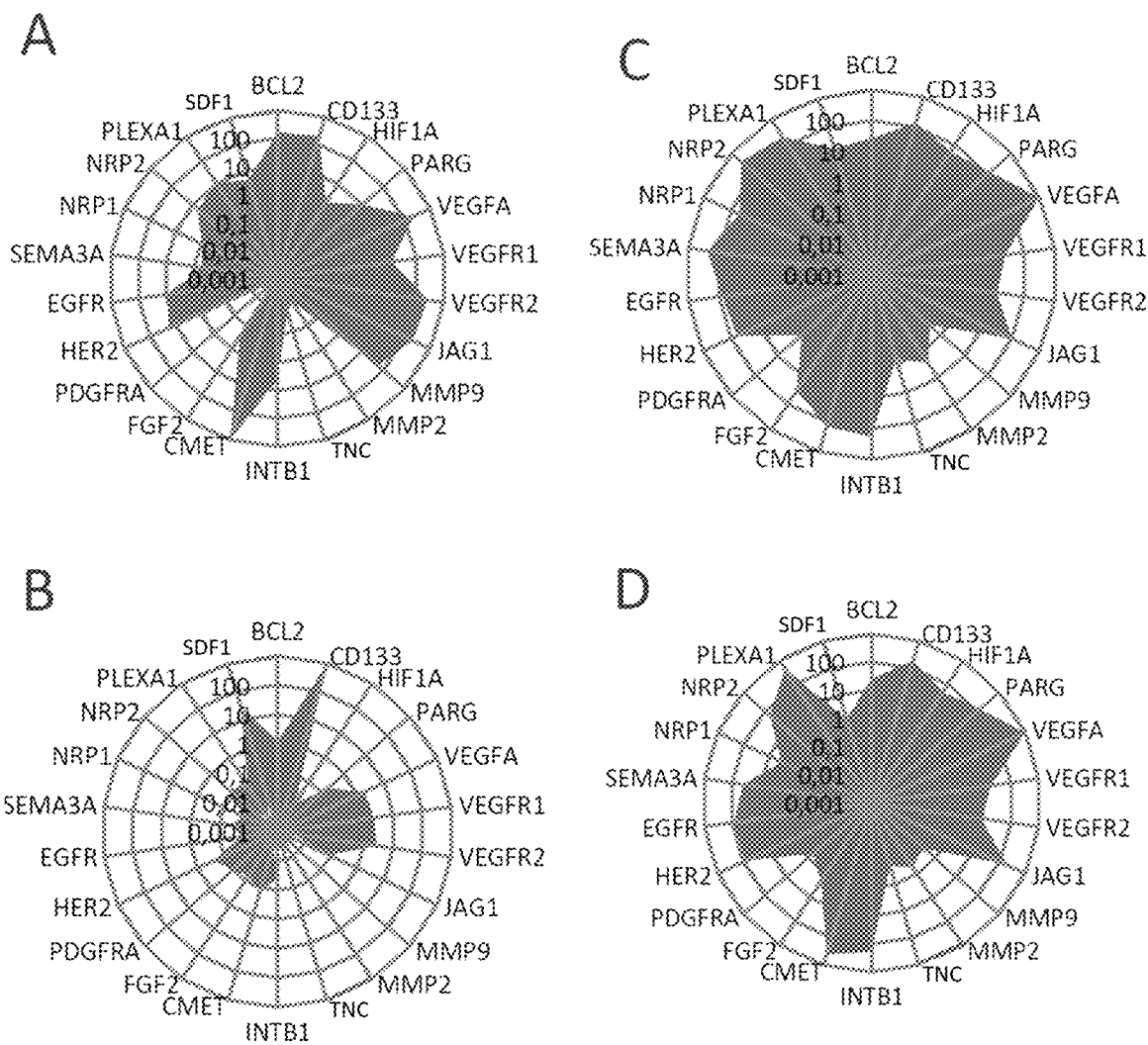
Figure 11A:
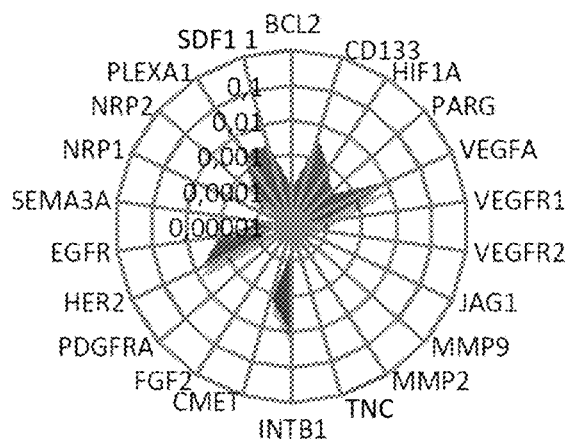
Figure 11B:
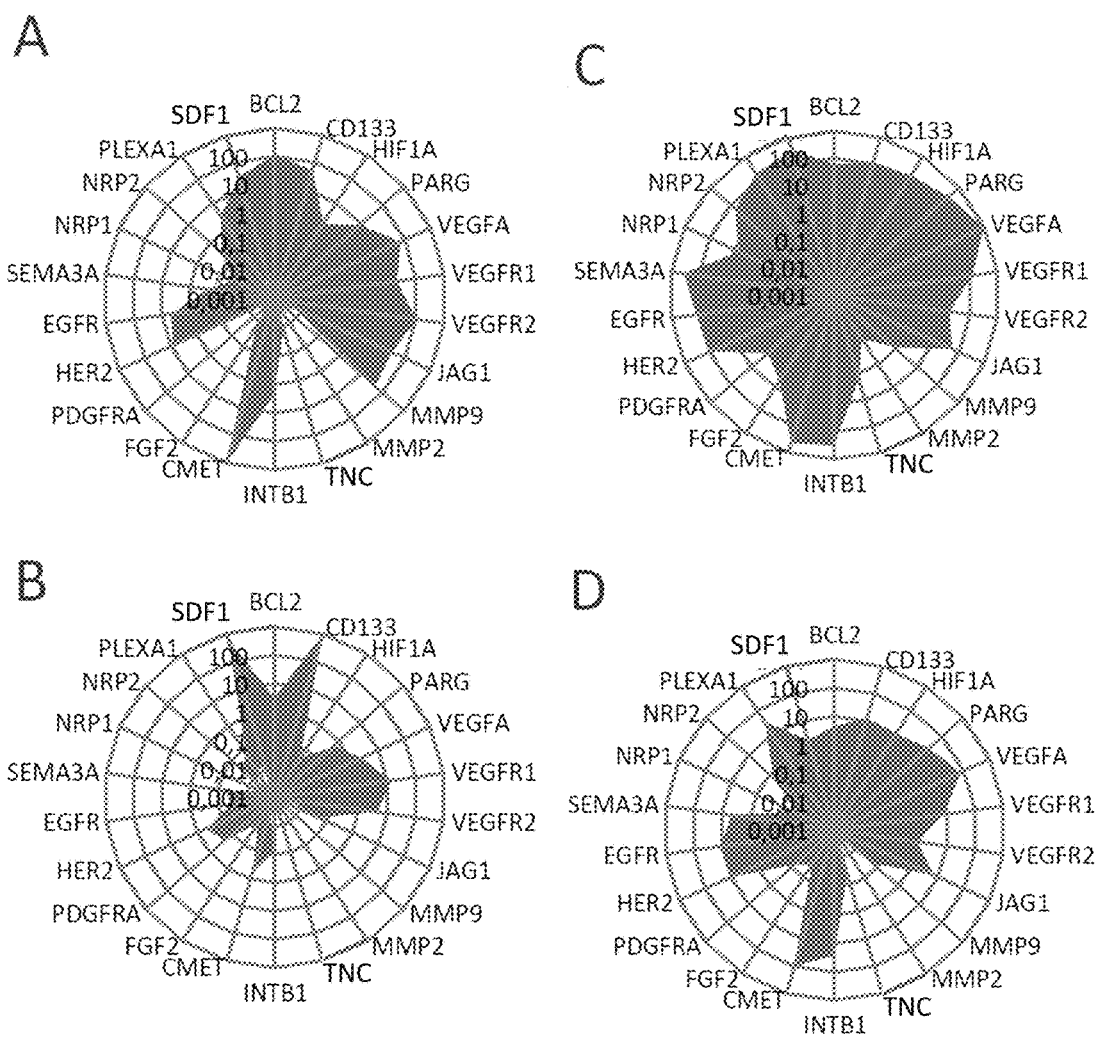
Figure 12A:
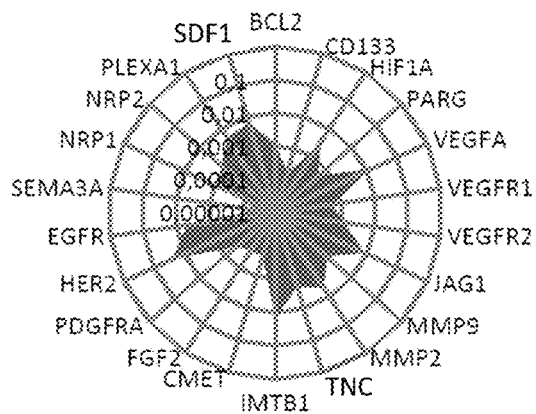
Figure 12B:
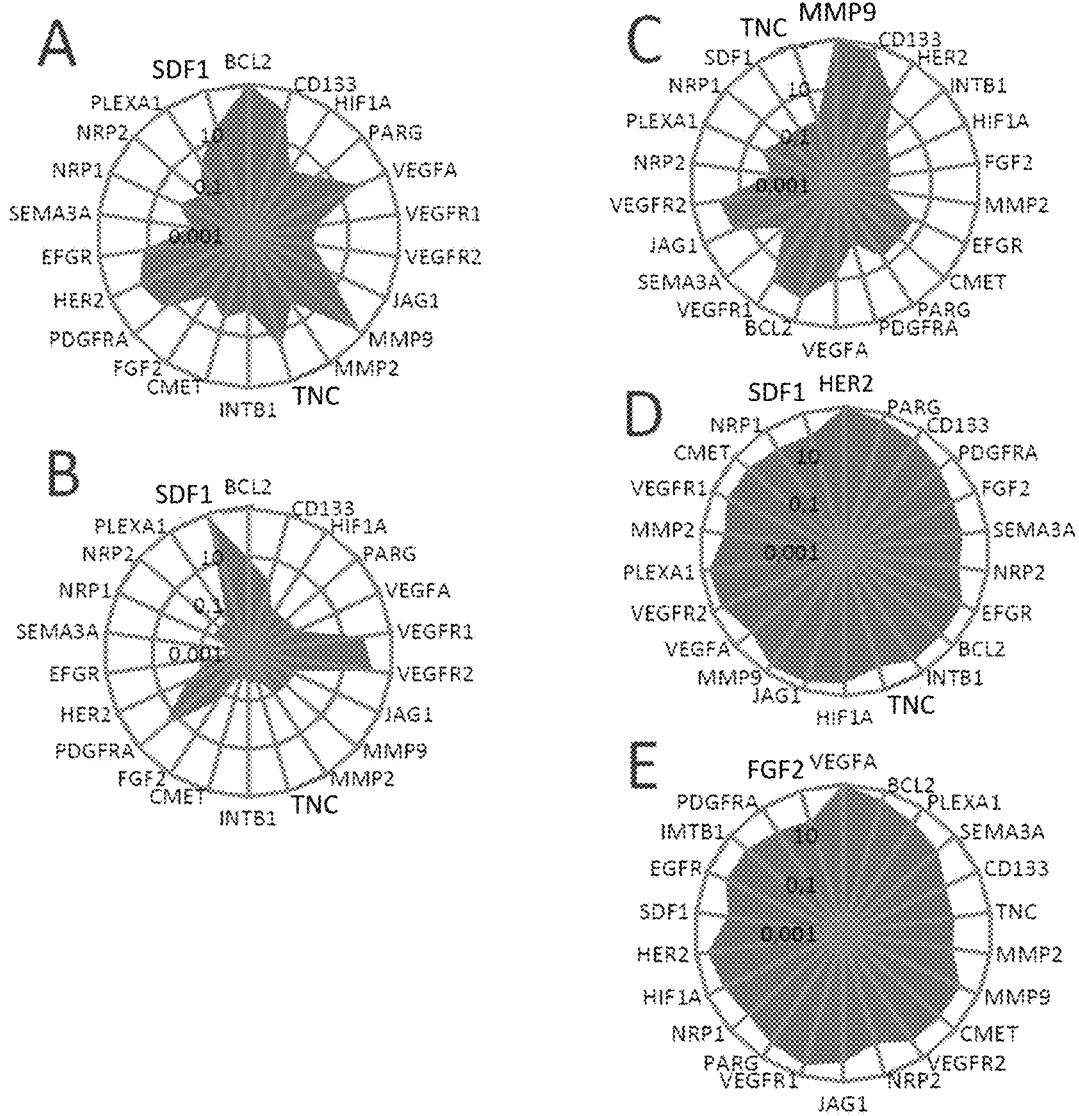
Figure 12C:
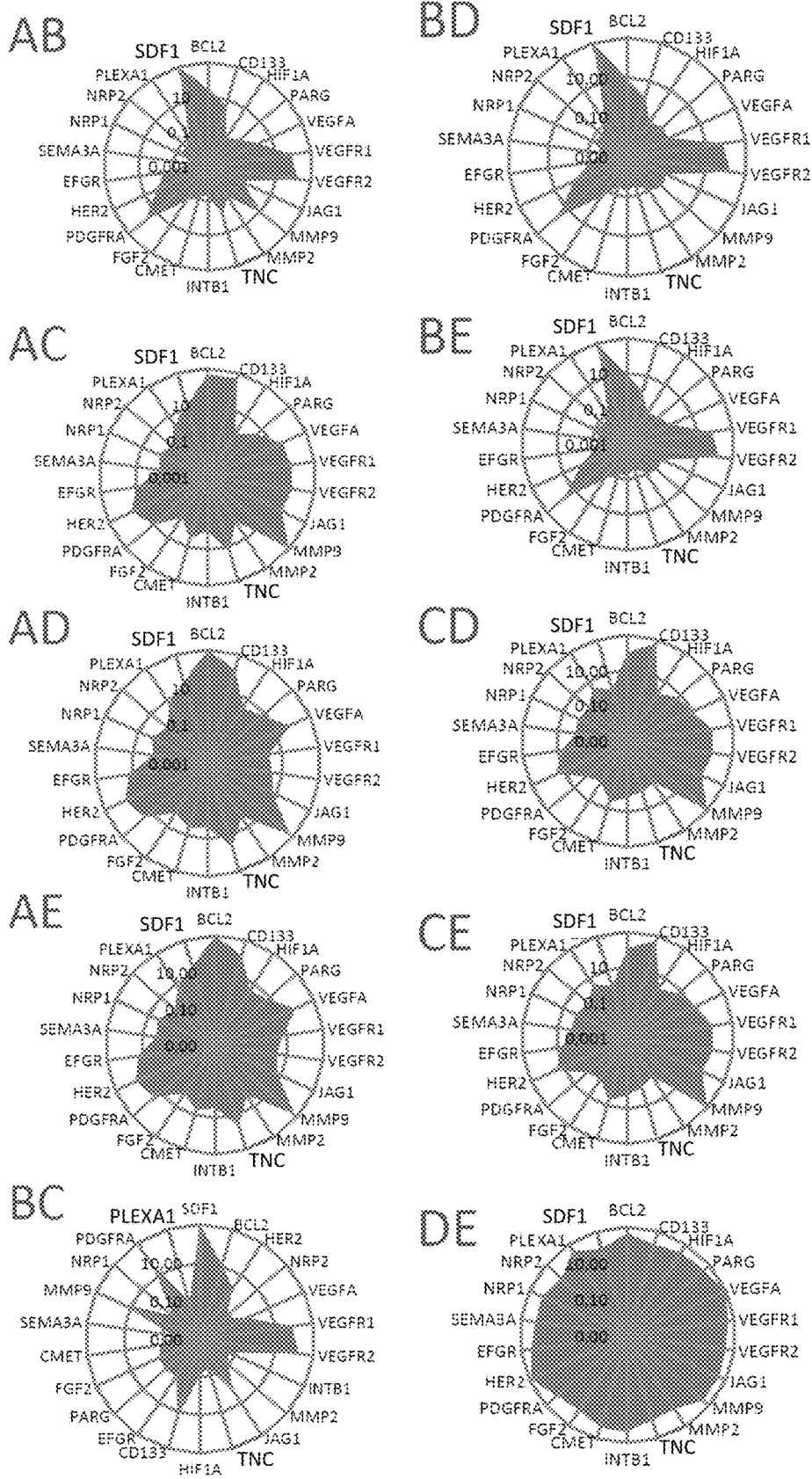
Figure 12E:
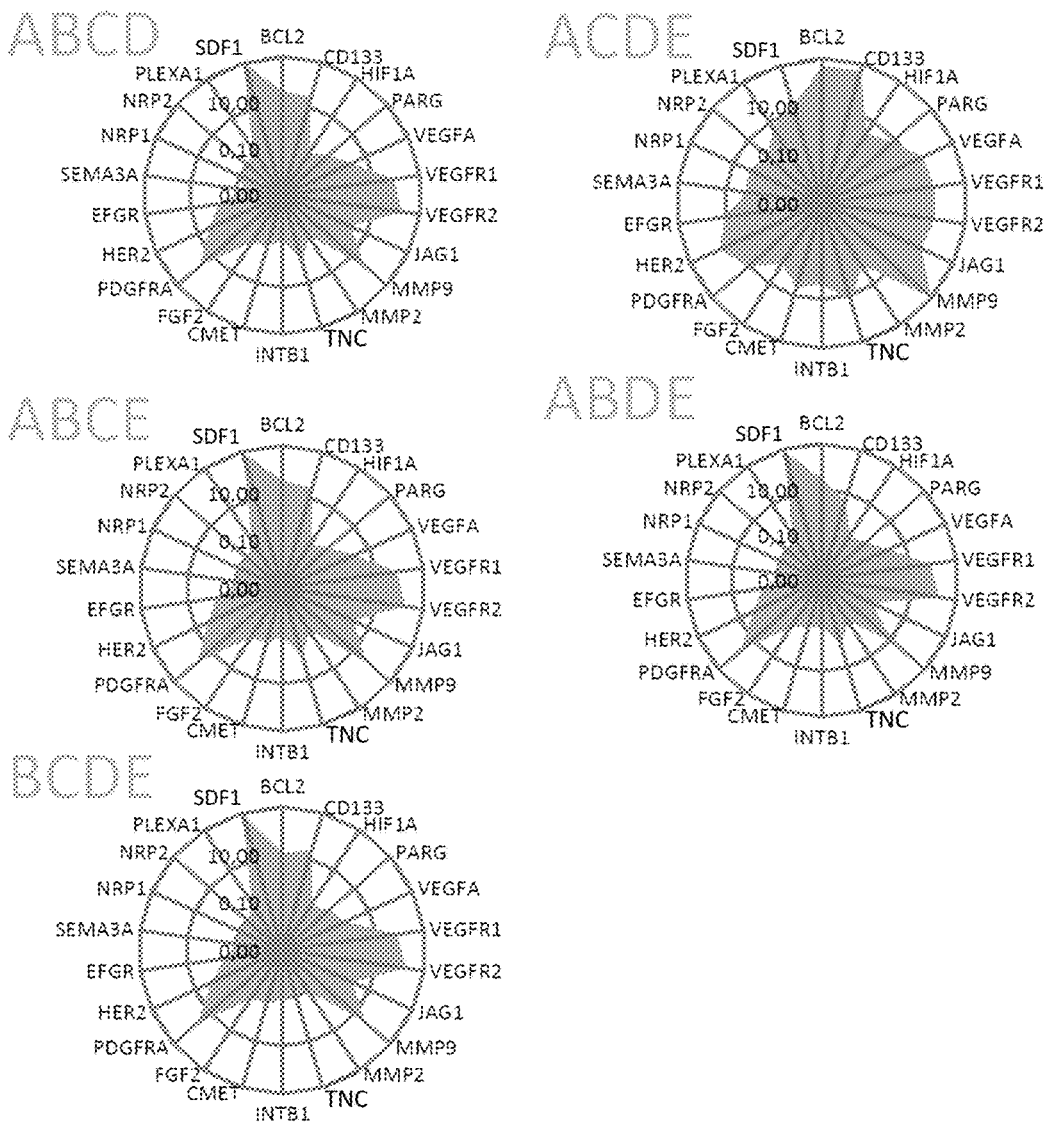
Figure 12F:
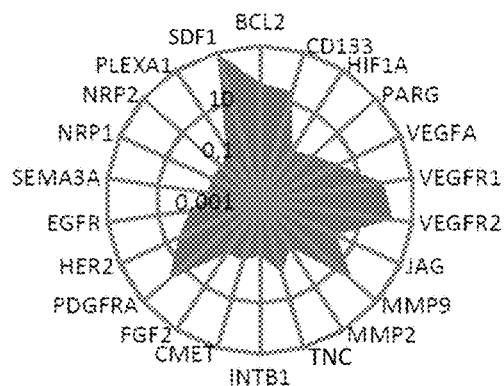
Figure 13A:
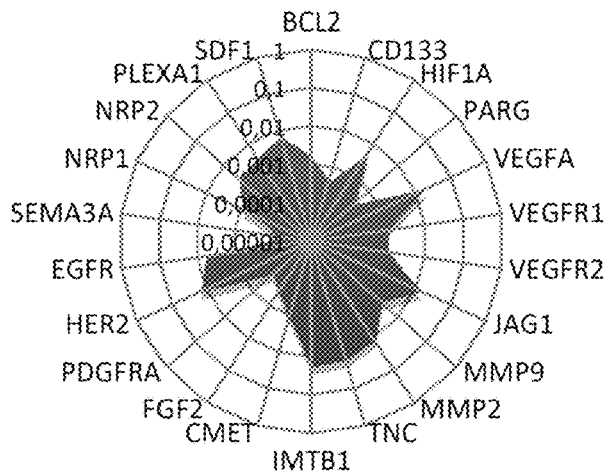
Figure 13B:
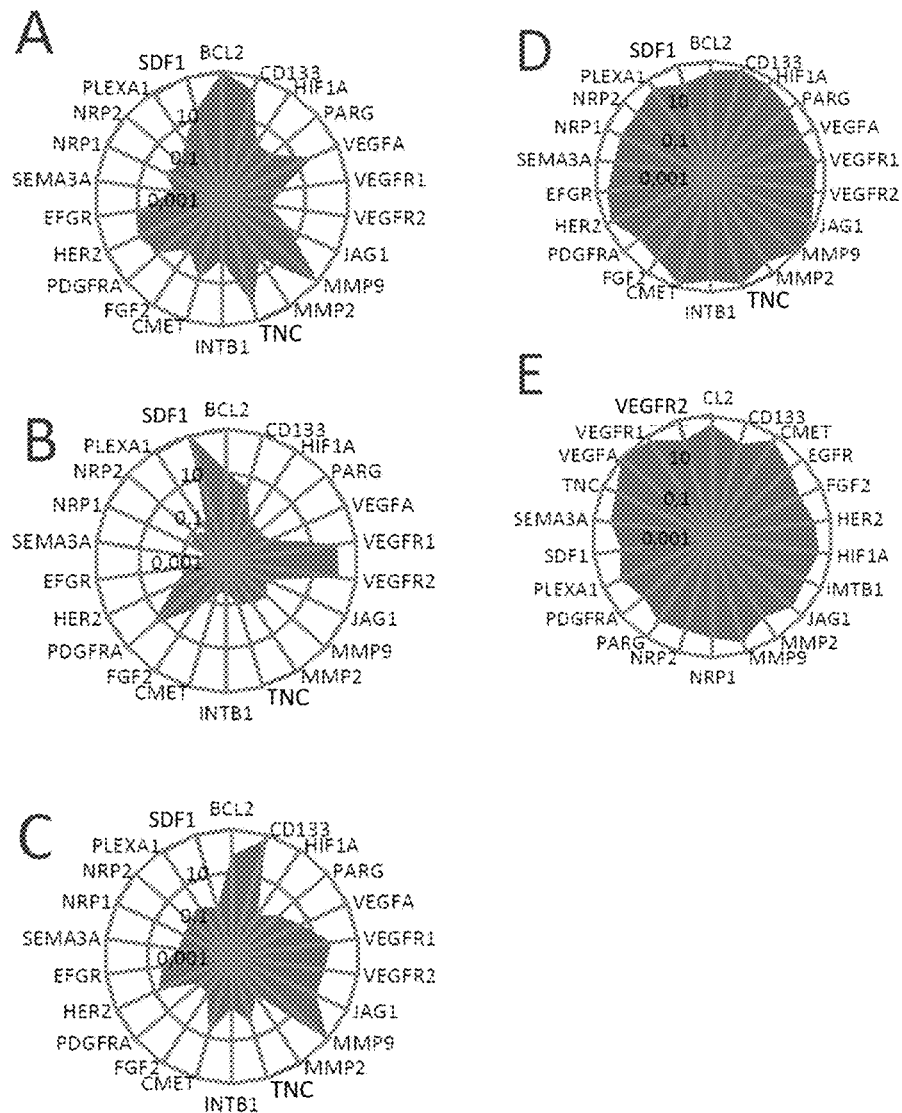
Figure 13C:
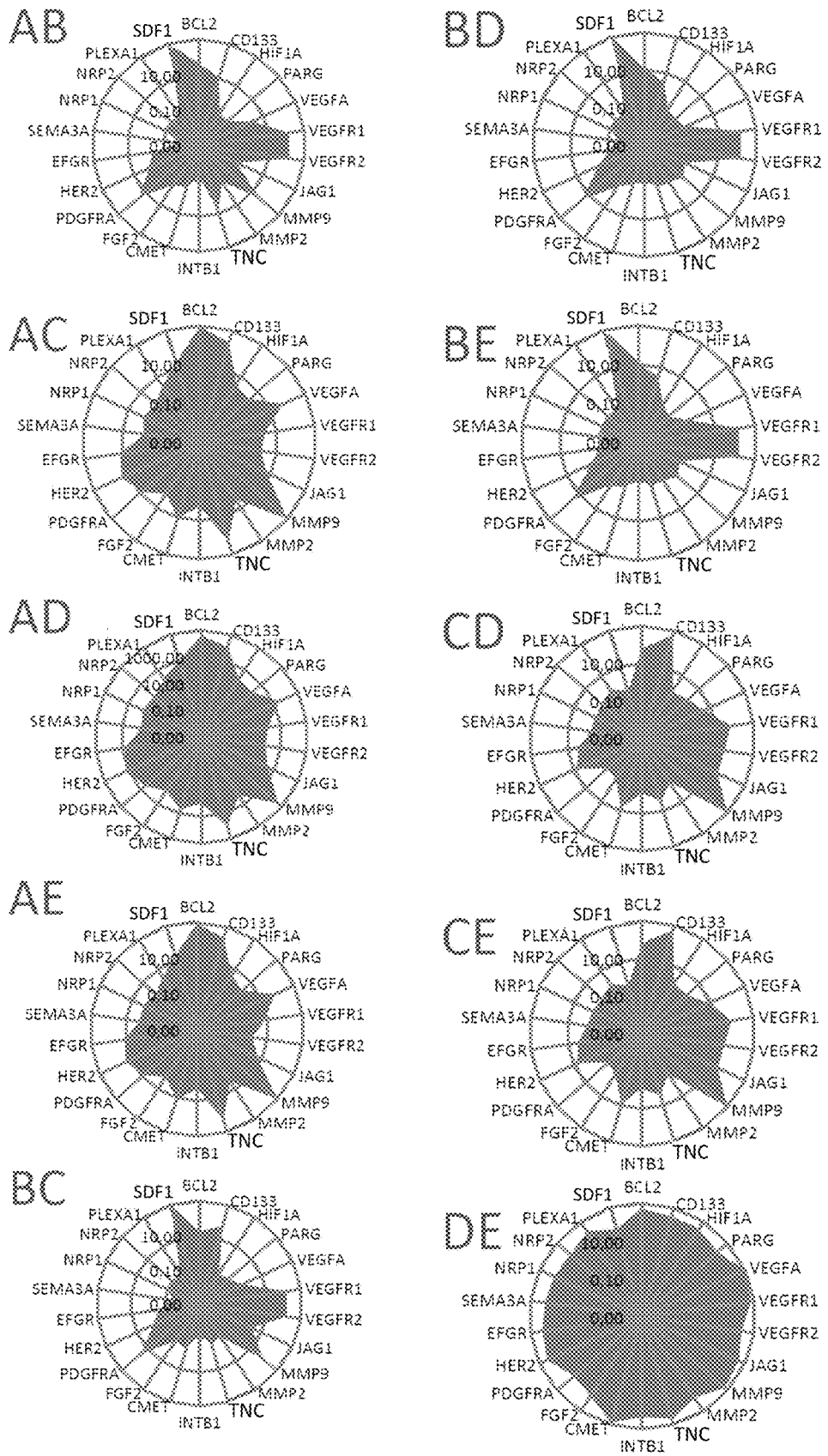
Figure 14A:
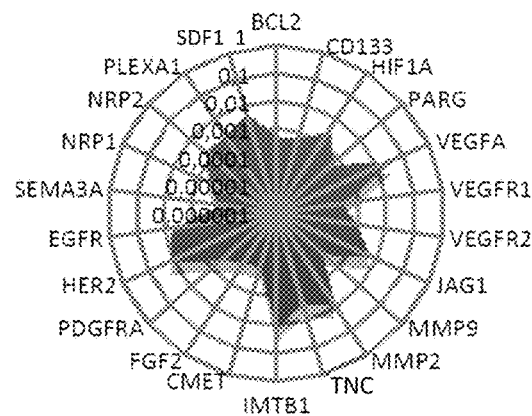
FIGS. 14A-14F: Personal signature obtained from a prostate adenocarcinoma biopsy (3). Radar mode of raw data (FIG. 14A), with one step of normalization (FIG. 14B), with two steps of normalization (FIG. 14C), with three steps of normalization (FIG. 14D), with four steps of normalization (FIG. 14E) and with five steps of normalization (FIG. 14F).
Figure 14B:
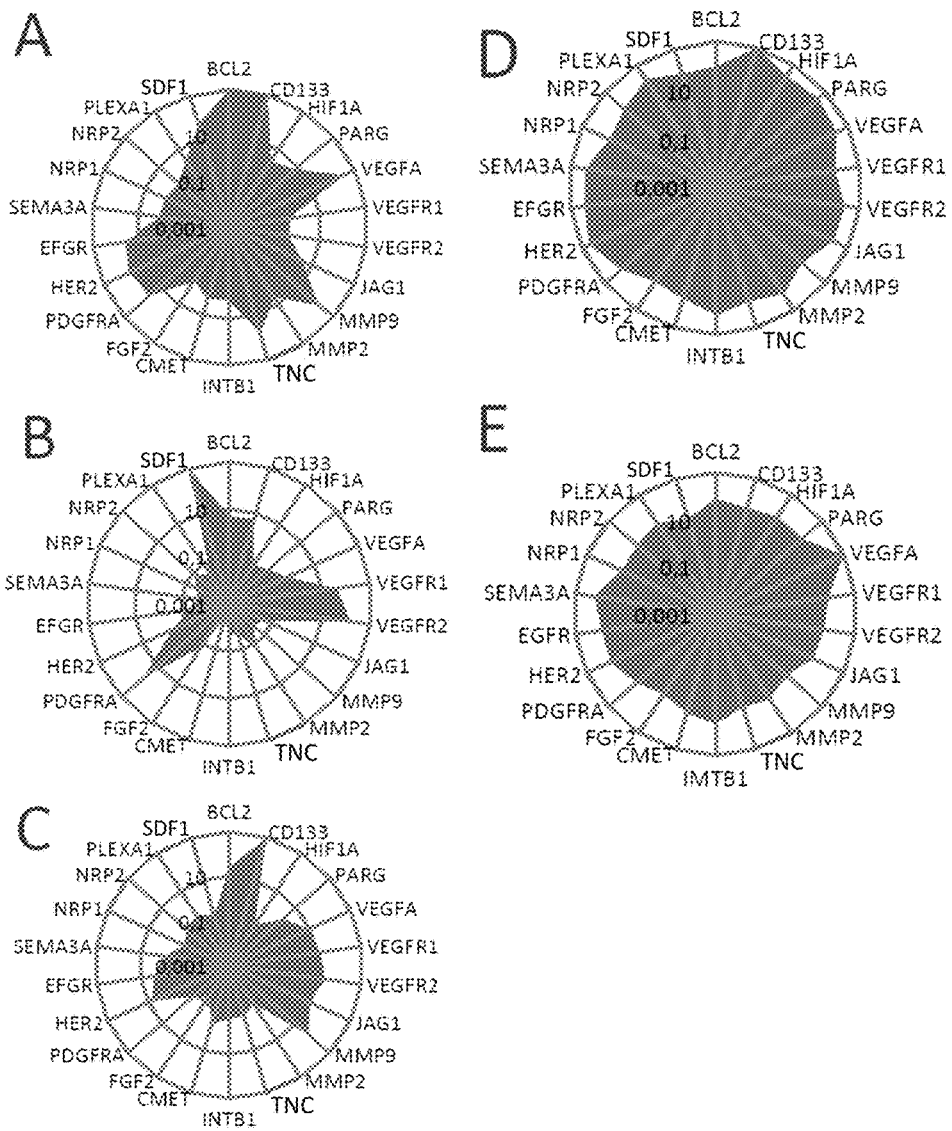
Figure 14C:
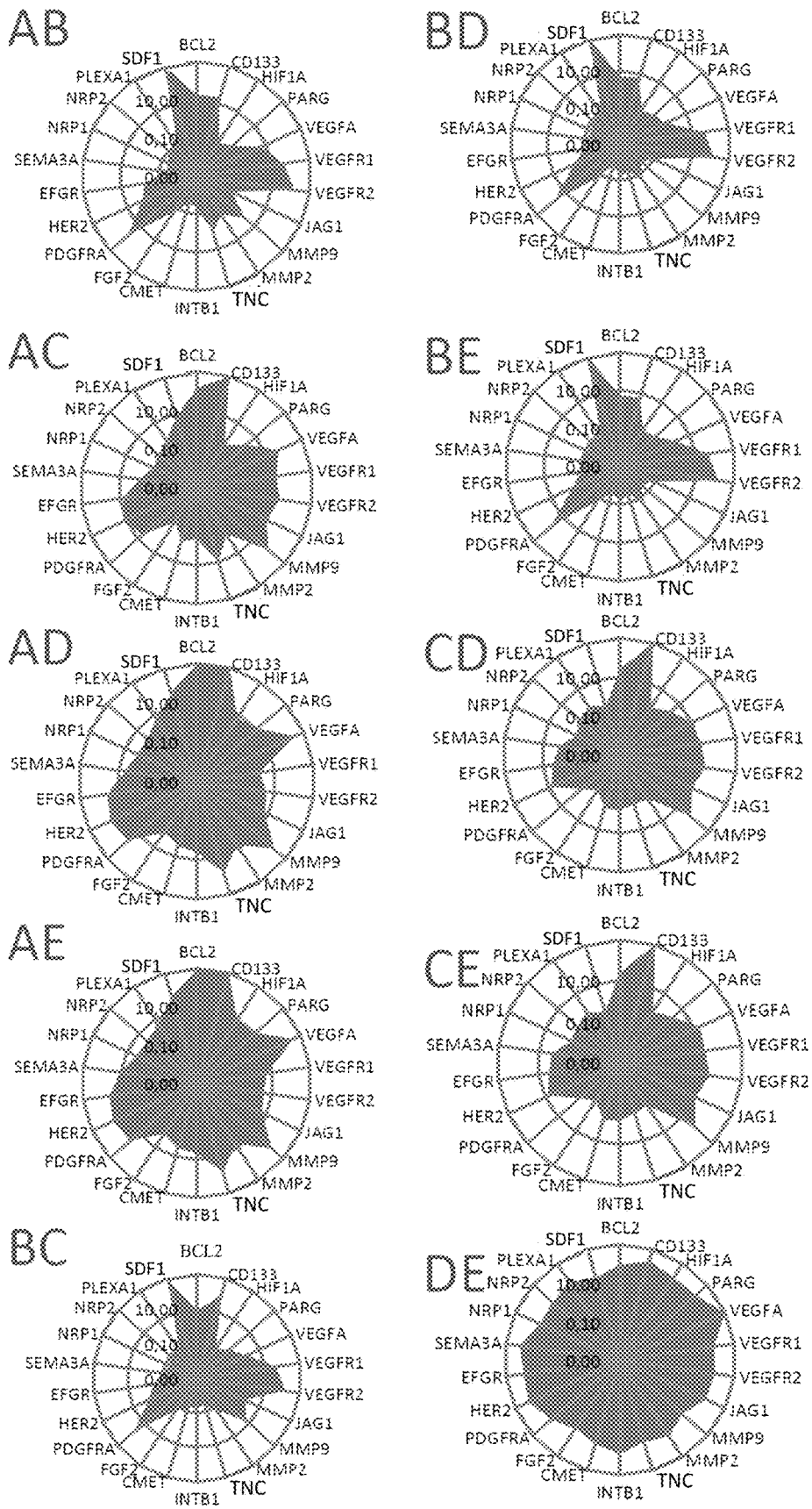
Figure 14D:
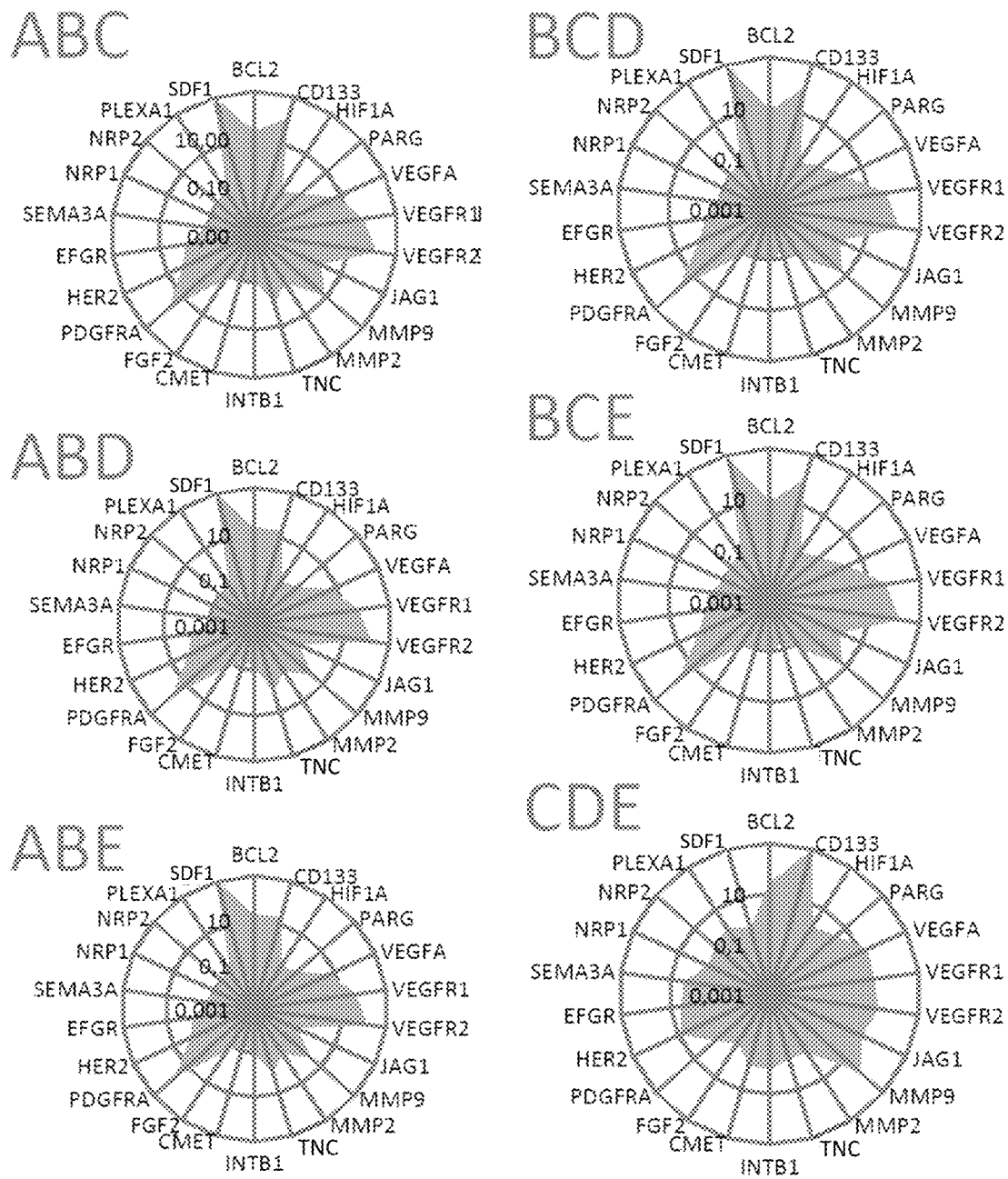
Figure 14E:
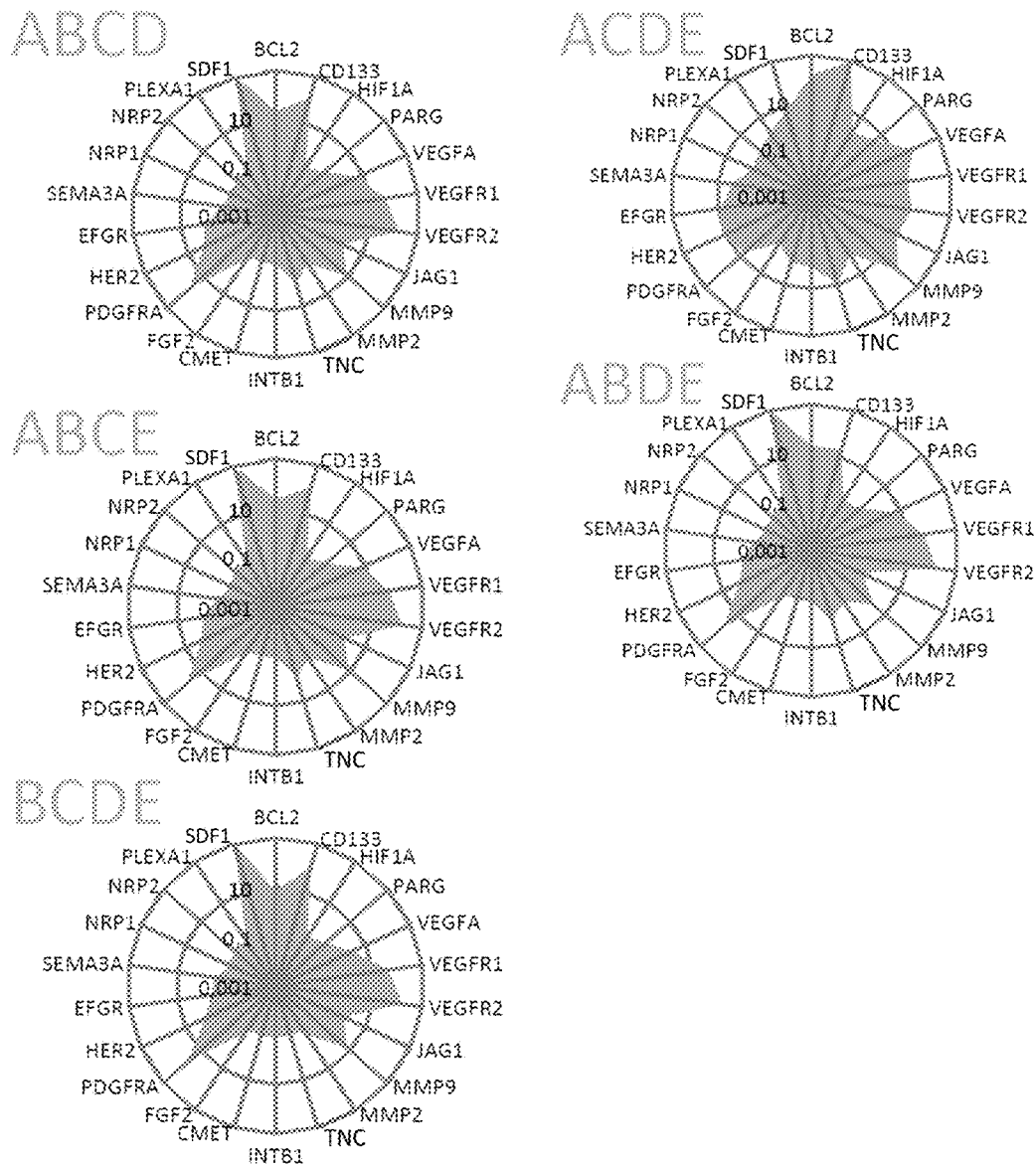
Figure 14F:
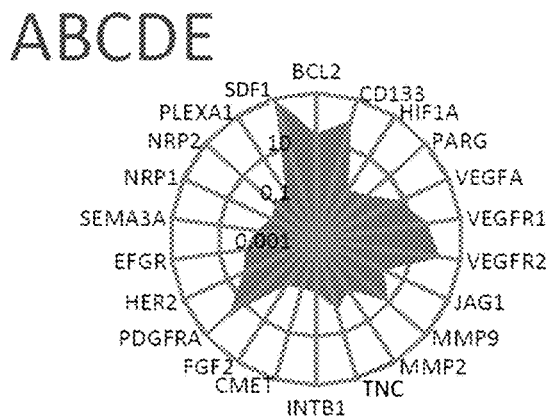

Validation of the Normalization Process:

Personal signatures are obtained using a normalization process comprising in the present examples 4-5 steps (4 steps for GBM and CC, 5 steps for PC). Each step corresponds to the comparison of the expression level of target genes with the expression level of this gene in reference samples defined as described herein. To validate the importance of the different steps of normalization, the signatures obtained with one step of normalization (being comparisons with reference A, B, C or D) or combinations of two steps (being comparisons with AD, AC, BC, BD, CD) or combinations of three steps (being comparisons with reference ABC, ABD, ADC, BCD) or full 4 steps normalization (ABCD) are presented in FIGS. 6 to 14. In the case of PC, the process contains 5 steps of normalization requiring more combinations (A, B, C, D, E) or (AB, AC, AD, AE, BC, BD, BE, CD, CE, DE) or (ABC, ABD, ABE, BCD, BCE, CDE) or (ABCD, ABCE, ABDE, ACDE, BCDE) or (ABCDE). Strikingly, the global analysis of intermediate signatures (with 1, 2, 3, 4 or 5 steps of normalization) reveals that the final signature (including all rounds of normalization) is different from all intermediate (partial) signatures (with only 1, 2 or 3 rounds of normalization or 1, 2, 3 and 4 rounds for PC). In all cases, it is important to note that the final signature is always different from the signature obtained with raw data, i.e. expression level of the genes without normalization. Rather, upon first round of normalization, whatever is the reference sample used the signature changes. This evolution is seen all along the process with target genes appearing either highly or poorly expressed as a function of the reference sample and/or round of normalization. In most of the cases, the signatures obtained from round 3 of normalization resemble the final ones but they always conserved some specific changes thereby demonstrating the importance of each step and each reference samples to get the final signatures with drug efficacy predictive value. This detailed and systematic analysis is presented here for 3 GBM (FIGS. 6-8), 3 CC (FIGS. 9-11) and 3 PC (FIGS. 12-14) but is applicable for all treated samples.

Validation of the Predictive Value of the Ranks

The normalization process allows ranking of target genes according to their expression level compared to various reference samples. The rank obtained for each target is from this point reflecting the hierarchy of signaling pathways activated in the tumors. Hence, this hierarchy is defining an objective criterion to select the best therapeutic option when considering that the highest ranks would correspond to the most important signaling pathways during tumor growth.

Challenging the Signature in Colon Cancer Patient CR-IC-028M:

To further validate this predictive value of the ranks we selected in our cohort a second patient derived biopsy which was also not responding to Cetuximab. In this assay, the signature was determined de novo from the patient derived xenograft grown in nude mice for amplification of the tumor sample and production of mice grafted with the tumor sample to perform the functional assay (40 mice). After RNA extraction and quality control of the samples the signature was determined for the set of genes meeting the criteria described above. Previous results showed that this CC model was resistant to standard of care Cetuximab (targeting EGFR). Indeed, as seen in FIG. 15, after normalization process, the rank for EGFR was only 7/9 of the potential therapeutic targets. However, we found that CMET, VEGFR1 and VEGFR2 were the targets with the highest scores. We decided to block VEGFR1 and VEGFR2 using a single drug (Cediranib). We decided to challenge the obtained signature by treating animals bearing the CC tumors with Cediranib (inhibiting VEGFR1 and VEGFR2 being ranked 2/9 and 3/9 respectively) compared to Cetuximab treated animals (ranked 7/9 and expected to be less or non-responsive). Hence, we also treated animals with Trastuzumab to block HER2, a target gene with an intermediate rank. As expected, tumor growth was not affected by treatment with Cetuximab. Similarly, Trastuzumab was not efficient in blocking tumor development. However, Cediranib exhibited in this model very significant anti-tumor activity. It reduces tumor volume (−50%, p=0.01, T-test at end point of the protocol) and the evolution of tumor growth (P<0.0001). This experiment confirmed that the method of the invention allows selecting the best therapeutic option among a selection of available drugs.

Challenging the Signature of Glioblastoma Patient HB21

In this assay, the signature was determined for a patient of 74 years old diagnosed for GBM. After RNA extraction and quality control of the samples the signature was determined for a set of genes meeting the criteria described above. A second part of the biopsy was used to graft 40 mice to reproduce the patient's tumor for a functional growth assay (orthotpic tumors implanted in the brain). As seen in FIG. 16, we found that MMP9 and VEGFR2 exhibited the highest ranks. We decided to generate 4 groups of tumor bearing mice (orthotopic grafting of the tumor cells in the striatum) treated with the standard of care (Temozolomide, an alkylating agent prodrug delivering a methyl group to purine bases of DNA), one group receiving MMP9 inhibitor (SB-3CT), one group receiving VEGFR2 inhibitor and one group receiving EGFR inhibitor (Erlotinib, a selective inhibitor of EGFR). Our results showed that inhibiting MMP9 or VEGFR2 induced a tumor growth inhibition identical to the one obtained with the standard of care (FIG. 16). This confirms that the normalization process is able to identify target genes important for tumor growth and that blocking these targets is reducing tumor growth. Strikingly, while not significantly different, the worse anti-tumor effect was obtained with the inhibitor of EGFR (−60% efficacy when compared to all other drugs), the target having a lower rank than MMP9 and VEGFR2. Thus, this functional assay confirmed that targeting the highest ranks post normalization is producing significant anti-tumor effect. Because Temozolomide is not a targeted therapy, it is not possible to integrate its target in the signature to calculate the corresponding score and compare it to the other targets.

Challenging the Signature in Prostate Cancer

To validate the predictive value of the ranks in prostate cancer, we selected in our cohort a patient-derived biopsy which was responding to Docetaxel, the current standard of care.

In this assay, the signature was determined de novo from the patient-derived xenograft grown in nude mice for amplification of the tumor sample and production of mice grafted with the tumor sample to perform the functional assay. After RNA extraction and quality control of the samples, the signature was determined for the set of genes meeting the criteria described above. We found that VEGFR2 was the target with the highest rank. We decided to challenge the obtained signature by treating animals bearing the PC tumors with Cediranib (inhibiting VEGFR2 being ranked 1/9) compared to Docetaxel treated animals (non-targeted therapy being standard of care and known to be effective on this PDX model). Hence, we also treated animals with Erlotinib to block EGFR, a target gene with a lower rank (ranked 4/9). As expected, tumor growth was inhibited by treatment with Docetaxel. Erlotinib was not efficient in blocking tumor development. However, Cediranib exhibited in this model very significant anti-tumor activity. It reduced tumor volume (−78% p=0.002, T-test at end point of the protocol) and the evolution of tumor growth (P<0.0001). This experiment confirmed that is the method of the invention allows selecting the best therapeutic option among a selection of available drugs in prostate cancer. (FIG. 17).

The inventors further demonstrated that the list of genes representative of therapeutically targetable signaling pathways, may be extended without modifying the relative ranking of preexisting genes.

A signature comprising 22 genes was obtained from a sample of brain tumor as described above. The list of genes was then enlarged by adding 8 and 14 new genes. As seen in FIG. 18, the relative hierarchy of the genes existing before the addition of these new genes was not altered, i.e., the new genes were intercalated in the ranking without modifying the relative position of preexisting genes.

This result demonstrate that the list of genes representative of therapeutically targetable signaling pathways may be easily extended in order to add therapeutical targets and/or signaling pathways.

The invention claimed is:

1. A method for selecting at least one therapeutically targetable dominant signaling pathway in a cancer sample from a subject affected with a solid cancer and treating the solid cancer comprising:

a) quantifying, by quantitative RT-PCR, expression levels in said cancer sample of a housekeeping gene and a set of genes representative of at least one therapeutically targetable signaling pathway, wherein the set of genes comprises at least 12 markers of tumor status selected from the group consisting of ABL1, ALK, CD276, BCL2, BRAF, PROM1, MET, CTLA4, EGFR, FGFR1, FGFR2, FGFR3, ERBB2, ERBB3, HIF1A, IGF1R, ITGA5, JAG1, MAP2K1, MAP2K2, MMP9, CD274, RET, CXCL12, VEGFA, KDR, FLT4, CEACAM1, CEACAM5, PIK3CA, AKT1, AR, HDAC1, HDAC2, RAF1, PDCD1, MDM2, CDK4, CDK6, IDO1, ABL2, FGFR4, ERBB4, KIT, EZH2, IDH1, IDH2, VHL, MTOR, TNFRSF10A, TNFRSF10B, ENTPD1, CREBBP, EP300, BRD4, GRB2, NOTCH1, NOTCH2, EPHA1, ANGPT1, TEK, RHOA, MMP2, DDR1, DDR2, KDM1A, FOXP3, CD27, ICOS, IL4, IL13, HMGB1, FPR1, TGFB1, TGFB2, CD40, IL6, CTNNB1, MYC, WNT2, WNT3, CXCR4, CXCL10, TLR4, IL2RB, PDCD1LG2, KIR2DL5A, NRP1, NRP2, PARG, FLT1, FGF2 and ITGB1, at least 9 markers of angiogenic and lymphangiogenic status selected from the group consisting of BRAF, EGFR, FGFR1, FGFR2, FGFR3, ERBB2, ERBB3, IGF1R, ITGA5, JAG1, MAP2K1, MAP2K2, MMP9, PDGFRA, PDGFRB, CXCL12, VEGFA, KDR, FLT4, CEACAM1, CEACAM5, PIK3CA, AKT1, RAF1, FGFR4, ERBB4, MTOR, NOTCH1, NOTCH2, EPHA1, ANGPT1, TEK, MMP2, CD34, CXCR4, TNC, NRP1, NRP2, PLXNA1, PLXNB1, FGF2, FLT1, TNN and ITGB1, at least 5 markers of tumor microenvironment selected from the group consisting of ABL1, ALK, MET, ITGA5, MAP2K1, MAP2K2, MMP9, RET, VEGFA, KDR, FLT4, CEACAM1, CEACAM5, ABL2, ERBB4, MTOR, NOTCH1, NOTCH2, EPHA1, ANGPT1, TEK, RHOA, ROCK1, ROCK2, MMP2, DDR1, DDR2, FLT1, FGF2, TNC, TNN, SEMA3A and ITGB1, and at least 9 markers of cell migration activity selected from the group consisting of ABL1, ALK, BRAF, MET, EGFR, FGFR1, FGFR2, FGFR3, IGF1R, ITGA5, JAG1, MAP2K1, MAP2K2, MMP9, PDGFRA, PDGFRB, RET, CXCL12, VEGFA, KDR, FLT4, CEACAM1, CEACAM5, PIK3CA, AKT1, RAF1, ABL2, FGFR4, ERBB4, KIT, MTOR, NOTCH1, NOTCH2, EPHA1, ANGPT1, TEK, RHOA, ROCK1, ROCK2, MMP2, DDR1, DDR2, HMGB1, TGFB1, TGFB2, MYC, WNT2, WNT3, CXCR4, CXCL10, FLT1, FGF2, TNC, TNN, SEMA3A, NRP1, NRP2, PLXNA1, PLXNB1 and ITGB1;

b) quantifying, by quantitative RT-PCR, the expression levels of the set of genes and the housekeeping gene from a sample from the organ from which said cancer originates, at least one low grade or benign tumor tissue corresponding to said cancer, and at least one normal cellular subtype of the organ from which said cancer originates;

c) calculating a score for each gene of the set of genes, wherein the score is calculated using the following formula:

$$\text{score} = 2^{-\Delta\Delta Ct}(\text{organ}) + \sum_{k=1}^{n}[2^{-\Delta\Delta Ct}(\text{low grade or benign tumor tissue})_k] + \sum_{i=1}^{m}[2^{-\Delta\Delta Ct}(\text{cellular subtype})_i]$$

wherein m and n are positive integers and are identical or different, and $$\Delta\Delta Ct(\text{organ, low grade or benign tumor tissue or cellular subtype}) = \Delta Ct(\text{cancer sample}) - \Delta Ct(\text{organ, low grade or benign tumor tissue or cellular subtype})$$

where ΔCt (cancer sample)=Ct (a gene of the set of genes in cancer sample)−Ct (housekeeping gene in cancer sample), and ΔCt (organ, low grade or benign tumor tissue or cellular subtype)=Ct (a gene of the set of genes in organ, low grade or benign tumor tissue or cellular subtype)−Ct (housekeeping gene in organ, low grade or benign tumor tissue or cellular subtype) thereby comparing the quantified expression levels provided in step a) to the expression levels provided in step b);

d) ranking each gene of the set of genes according to said calculated score for each gene of the set of genes, e) selecting the at least one therapeutically targetable dominant signaling pathway comprising the gene having the highest score; and f) administering a chemotherapeutic treatment to the subject that targets the selected at least one therapeutically targetable dominant signaling pathway or treating the subject with a treatment protocol that targets the selected at least one therapeutically targetable dominant signaling pathway, said chemotherapeutic treatment or treatment protocol comprising administering a chemical substance or a biochemical substance to the subject.

2. The method according to claim 1, wherein the cancer is selected from the group consisting of glioma, colon cancer, prostate cancer, skin cancer, lung cancer, pancreas cancer, liver cancer, kidney cancer, head and neck cancer and breast cancer.

3. The method according to claim 1, wherein the solid cancer is glioma and wherein in step b) the variations of the expression levels of each of said genes provided in step a) are determined compared to the expression levels of said genes in normal brain, in astrocytoma grade II, and in normal brain astrocytes and normal brain oligodendrocytes.

4. The method according to claim 1, wherein the solid cancer is colon cancer and the organ from which said cancer originates is a normal colon and/or in colonic smooth muscle cells, the at least one low grade or benign tumor tissue corresponding to said cancer is non-cancerous polyps or a low grade colon tumor, and the at least one normal cellular subtype of the organ from which said cancer originates is normal colonic epithelial cells.

5. The method according to claim 1, wherein the solid cancer is prostate cancer and wherein in step b) the variations of the expression levels of each of said genes provided in step a) are determined compared to the expression levels of said genes
- in normal prostate,
- in glandular hyperplasia of prostate, and
- in normal prostate epithelial cells, prostate microvascular endothelial cells and/or prostate fibroblasts.

6. The method according to claim 1, wherein the solid cancer is skin cancer and wherein in step b) the variations of the expression levels of each of said genes provided in step a) are determined compared to the expression levels of said genes
- in normal skin tissue,
- in at least a low grade melanoma (stage 0), and
- in at least normal epidermal epithelial cells, dermal epithelial cells, keratinocytes, melanocytes, Langerhans cells, Merkel cells and/or skin endothelial cells.

7. The method according to claim 1, wherein the solid cancer is lung cancer and wherein in step b) the variations of the expression levels of each of said genes provided in step a) are determined compared to the expression levels of said genes
- in normal lung,
- in at least a low grade lung tumor (grade I or II), and
- in at least normal lung smooth muscular cells, lung fibroblasts, alveolar epithelial cells, bronchial epithelial cells and/or tracheal epithelial cells.

8. The method according to claim 1, wherein the solid cancer is pancreas cancer and wherein in step b) the variations of the expression levels of each of said genes provided in step a) are determined compared to the expression levels of said genes
- in normal pancreas,
- in at least a low grade pancreas tumor (grade I or II), and
- in at least normal pancreas endothelial cells, acinar cells, centroacinar cells, duct cells, stellate cells and/or islets cells (Langerhans).

9. The method according to claim 1, wherein the solid cancer is liver cancer and wherein in step b) the variations of the expression levels of each of said genes provided in step a) are determined compared to the expression levels of said genes
- in normal liver,
- in at least a low grade liver tumor (grade I or II), and
- in at least normal hepatocytes, liver endothelial cells and/or Kupffer Cells.

10. The method according to claim 1, wherein the solid cancer is kidney cancer and wherein in step b) the variations of the expression levels of each of said genes provided in step a) are determined compared to the expression levels of said genes
- in normal kidney,
- in at least a low grade kidney tumor (grade I or II), and
- in at least normal mesangial cells, stroma cells, glomerular endothelial cells, podocytes, epithelial cells, cortical epithelial cells and/or tubular cells.

11. The method according to claim 1, wherein the solid cancer is a head and neck cancer and wherein in step b) the variations of the expression levels of each of said genes provided in step a) are determined compared to the expression levels of said genes
- in the normal organ or tissue,
- in at least a low grade head and neck tumor (grade I or II), and
- in at least normal cells from the oral cavity, from oropharynx and/or from hypopharynx.

12. The method according to claim 1, wherein the solid cancer is breast cancer and wherein in step b) the variations of the expression levels of each of said genes provided in step a) are determined compared to the expression levels of said genes
- in normal breast,
- in at least a low grade breast tumor (grade I or II), and
- in at least normal breast fibroblasts and/or epithelial cells.

13. The method according to claim 1, wherein the method comprises administering a chemical substance or biochemical substance to the subject, said chemical substance or biochemical substance being selected from the group consisting of:
- plerixafor or NOX-A12 to target DSF1;
- ABT-199 (Venetoclax), genasense (G3139), ABT-737, ABT-263, venetoclax, or SPC2996 to target BCL2;
- XAV-939 to target CD133;
- digoxin, bortezomib, R070701790, or EZN-2968 to target HIF1A;
- GPI 16552 to target PARG;
- bevacizumab or aflibercept to target VEGFA;
- vandatenib, pasopanib, sunitinib, axitinib, or regorafenib to target VEGFR1;
- cediranib, ponatinib, regorafenib, ramucirumab, BR55, or ZD6474 to target VEGFR2;
- synthetic peptide PCK3145, marimastat, or GS-5745 to target MMP9;
- incyclidine or marimastat to target MMP2;
- Cilengitide to target ITGB1;
- crizotinib, SU11274, cabozantinib, tivantinib, capmatinib (INC280), AMG 337, or tepotinib (MSC2156119J) to target CMET;
- vargatef or AZD4547 to target FGF2;
- imatinib, axitinib, olaratumab (LY3012207, IMC-3G3), MEDI-575, crenolanib, or DCC-2618 to target PDGFRA;
- trastuzumab, lapatinib, afatinib, pertuzumab, or MM-111 to target HER2;
- lapatinib, afatinib, cetuximab, erlotinib, osimertinib (AZD9291), or gefitinib (ZD-1839) to target EGFR;
- NRP1 peptidic antagonist ILITIIAMSALGVLLGAVCGWL;
- NRP2 peptidic antagonist ILITIIAMSSLGVLLGATCAGLLLY;
- PLEXA1 peptidic antagonist LLTLPAIVGIGGGGGLLLLVIVAVLIA;
- RO4929097 or LY3039478 to target JAG;
- neuradiab to target TNC;
- alpha GSK2636771, wortmannin, XL147, or alpelisib (BYL719) to target PI3K;
- ARQ 751, AZD5363, or BAY1125976 to target AKT1;
- atezolizumab (MPDL3280A), avelumab, durvalumab, or pembrolizumab to target PDL1 (CD274);
- axitinib, famitinib, or AG-013736 to target VEGFR3 (FLT4);
- bicalutamide or flutamide to target androgen receptor (AR);
- BMS-936564, BKT140, BL-8040, USL311, plerixafor, LY2510924, or MSX-122 to target CXCR4;
- CEA inhibitors or SAR408701 to target CEACAM-5;
- cixutumumab, figitumumab (CP-751871), linsitinib (OSI-906), B11B022, AVE1642, IMC-A12, or RG1507 to target IGF1R;
- crizotinib, ceritinib, or alectinib to target ALK;
- dabrafenib or trametinib to target C-RAF (RAF1);

dasatinib, bosutinib, imatinib, or nilotinib to target ABL1;
dasatinib or BP1001 to target GRB2;
DCR-MYC to target MYC;
epacadostat (INCB024360), GDC-0919, or indoximod to target IDO1;
everolimus, temsirolimus, SAR245409, or MLN0128 to target mTOR;
fasudil, Y39983, or BA-210 to target RHOA;
fasudil, Y39983, or BA-210 to target ROCK 1;
fasudil, Y39983, or BA-210 to target ROCK 2;
GSK1795091 or GLA-SE to target TLR4;
GSK3359609 or MEDI-570 to target ICOS (CD278);
IDH1 peptide vaccine, AG120, AG221, AG881, azacitidine, or BAY1436032 to target IDH1;
imatinib to target ABL2;
IPH2101, lirilumab, or anti-KIR (1-7F9) to target KIR2DL5A;
IPH52 or PSB 069 to target CD39 (ENTPD1);
ipilimumab, tremelimumab, MDX-010, or AGEN 1884 to target CTLA4;
JQ1, PFI1, or OTX015 to target BRD4;
KBP-5209 or ASLAN001 to target HER4 (ERBB4);
lenvatinib, nintedanib (BIBF 1120), or GSK3052230 to target FGFR1;
lenvatinib, nintedanib, or BAY1187982 to target FGFR2;
lenvatinib, nintedanib, FGF401, BLU-554, or U3-1784 to target FGFR4;
lenvatinib, nintedanib, LY3076226, or B-701 to target FGFR3;
LY3039478 or MK0752 to target NOTCH 1;
LY3039478 or MK0752 to target NOTCH 2;
mapatumumab to target TRAIL-R1 (TNFRSF10A);
mapatumumab to target TRAIL-R2 (TNFRSF10B);
mepolizumab to target IL6;
MGA271 to target B7-H3 (CD276);
MM-121, GSK2849330, U3-1287 (AMG888), or MM-111 to target ERBB3;
nivolumab, pembrolizumab, or pidilizumab (CT-011) to target PD1;
nutlin, DS-3032, or RO5503781 to target MDM2;
OG-L002, GSK2879552, IMG-7289, or INCB059872 to target KDM1A (LSD1);
palbociclib (PD0332991), ribociclib (LEE011), G1T28, or abemaciclib to target CDK4;
panobinostat (LBH 589), vorinostat, or romidepsin (FR901228) to target HDAC1;
anobinostat (LBH 589), vorinostat, or romidepsin (FR901228) to target HDAC2;
panobinostat, vorinostat, or romidepsin to target CREBBP;
panobinostat, vorinostat, romidepsin, ep300i, or BRD4i to target EP300;
PF-04605412 to target IntαV (ITGA5);
PRI-724 to target CTNNB1;
QBX258, IL-13-PE, or IL13-PE38QQR to target IL13;
QBX258 or recombinant interleukin-4 to target IL4;
R06867461 or CEP-11981 to target Tie2 (TEK);
selectikine, ALT-801, or recombinant human interleukin-2 to target IL2RB;
sunitinib or imatinib to target KIT;
sunitinib, crenolanib, axitinib, or sorafenib to target PDGFRB;
tazemetostat (EPZ-6438), GSK126, or azacitidine to target EZH2;
trametinib, mekinist, or binimetinib (MEK162) to target MEK 1 (MAP2K1);
vandetanib or RXDX-105 to target RET;
vandetanib, regorafenib, trebananib, or CVX-241 to target ANGPT1;
varlilumab (CDX-1127) to target CD27;
vemurafenib, dabrafenib (GSK2118436), or encorafenib (LGX818) to target BRAF;
WNT974 to target WNT 2; and
WNT974 to target WNT 3.

* * * * *

UNITED STATES PATENT AND TRADEMARK OFFICE
CERTIFICATE OF CORRECTION

PATENT NO. : 11,823,799 B2
APPLICATION NO. : 15/777234
DATED : November 21, 2023
INVENTOR(S) : Dominique Bagnard et al.

It is certified that error appears in the above-identified patent and that said Letters Patent is hereby corrected as shown below:

In the Specification

Column 13,
Line 16, "Wnt/0-catenin" should read --Wnt/β-catenin--.

Column 21,
Line 1, "NCBJ:" should read --NCBI:--.

Column 25,
Line 55, "MILK 1" should read --MEK 1--.

Column 37,
Line 67, "taking $2^{-\Delta Ct}$" should read --taking $2^{-\Delta\Delta Ct}$--.

Column 52,
Line 22, "[(a×b$^2$) 2]," should read --[(a×b$^2$) / 2],--.
Line 51, "[(a×b$^2$) 2]," should read --[(a×b$^2$) / 2],--.

Signed and Sealed this
Sixteenth Day of July, 2024

Katherine Kelly Vidal
*Director of the United States Patent and Trademark Office*